US012708259B1

(12) United States Patent
Reynard

(10) Patent No.: US 12,708,259 B1
(45) Date of Patent: Aug. 18, 2026

(54) SYSTEMS AND METHODS FOR AI-GATING PHOTOMODULATION

(71) Applicant: Michael Reynard, Santa Monica, CA (US)

(72) Inventor: Michael Reynard, Santa Monica, CA (US)

( * ) Notice: Subject to any disclaimer, the term of this patent is extended or adjusted under 35 U.S.C. 154(b) by 0 days.

(21) Appl. No.: 19/421,567

(22) Filed: Dec. 16, 2025

(51) Int. Cl.
*A61B 3/00* (2006.01)
*G01N 21/47* (2006.01)

(52) U.S. Cl.
CPC .......... *A61B 3/0008* (2013.01); *A61B 3/0025* (2013.01); *G01N 21/4795* (2013.01); *G01N 2021/4797* (2013.01)

(58) Field of Classification Search
CPC .......................... A61B 3/0008; A61B 3/0025; G01N 21/4795; G01N 2021/4797
USPC .......................................................... 351/221
See application file for complete search history.

(56) References Cited

U.S. PATENT DOCUMENTS 5,237,173 A 8/1993 Stark et al.
7,848,035 B2 12/2010 DeLapp et al.
8,149,526 B2 4/2012 DeLapp et al.
9,017,391 B2 4/2015 McDaniel
9,192,780 B2 11/2015 McDaniel
10,171,259 B2 1/2019 Kuwata et al.
10,252,078 B2 4/2019 Dotson
10,596,037 B2 3/2020 Tedford et al.
10,881,550 B2 1/2021 Tedford et al.
11,009,707 B2 5/2021 Peng et al.
11,285,335 B2 3/2022 Asprey et al.
11,360,557 B2 6/2022 Berkner-Cieslicki et al.
11,467,407 B2 10/2022 DeLapp et al.
11,740,467 B2 8/2023 Peng et al.
11,829,528 B2 11/2023 Berkner-Cieslicki et al.
11,852,816 B1 12/2023 DeLapp et al.
11,986,666 B2 5/2024 Cockrell et al.
12,011,611 B2 6/2024 Hunter et al.
12,085,724 B1 9/2024 DeLapp et al.
12,157,011 B2 12/2024 Huang
12,336,937 B2 6/2025 Tedford et al.
12,390,657 B2 8/2025 Cockrell et al.
12,390,658 B2 8/2025 Tedford et al.
(Continued)

OTHER PUBLICATIONS

Shu et al. (CN 110537124); Light Detector Measures of Accuracy for LIDAR (Year: 2019).*
(Continued)

*Primary Examiner* — Bumsuk Won
*Assistant Examiner* — Rahman Abdur
(74) *Attorney, Agent, or Firm* — Richard A Baker, Jr.

(57) ABSTRACT

An AI-controlled photonic system that performs therapeutic photomodulation and reflective optical diagnostics, including OCT, OCTA, near-infrared reflectance, and fundus auto-fluorescence, is described here. The system incorporates an AI-Predictive Gating module that identifies optimal temporal windows for energy delivery or data acquisition based on reflectance dynamics, retinal motion, physiologic parameters, mitochondrial biomarkers, and image-quality metrics. By synchronizing photonic emission and diagnostic capture to predicted physiologic states, the system improves diagnostic fidelity, enhances therapeutic precision, and enables earlier detection of degenerative, inflammatory, and pharmacologic retinal injury.

29 Claims, 10 Drawing Sheets

(56) References Cited

U.S. PATENT DOCUMENTS

| | | | | |
|---|---|---|---|---|
| 2003/0158587 | A1* | 8/2003 | Esteller | G16H 50/30 607/45 |
| 2006/0035883 | A1 | 2/2006 | Tedford et al. | |
| 2010/0067128 | A1 | 3/2010 | DeLapp et al. | |
| 2010/0211136 | A1 | 8/2010 | Taboada et al. | |
| 2011/0102916 | A1 | 5/2011 | DeLapp et al. | |
| 2011/0161047 | A1 | 6/2011 | Sazuka et al. | |
| 2016/0067086 | A1 | 3/2016 | Tedford et al. | |
| 2017/0027444 | A1* | 2/2017 | Rege | A61B 3/0041 |
| 2017/0225012 | A1 | 8/2017 | Dotson et al. | |
| 2018/0368679 | A1* | 12/2018 | An | A61B 3/0025 |
| 2019/0142636 | A1 | 5/2019 | Tedford et al. | |
| 2020/0004020 | A1 | 1/2020 | Bhakta et al. | |
| 2020/0049996 | A1 | 2/2020 | Yan et al. | |
| 2020/0159020 | A1 | 5/2020 | Peng et al. | |
| 2020/0315844 | A1 | 10/2020 | Tedford et al. | |
| 2021/0041948 | A1 | 2/2021 | Berkner-Cieslicki et al. | |
| 2021/0178178 | A1 | 6/2021 | Tedford et al. | |
| 2021/0231960 | A1 | 7/2021 | Peng et al. | |
| 2021/0315736 | A1 | 10/2021 | Tedford et al. | |
| 2022/0011496 | A1 | 1/2022 | Bhakta et al. | |
| 2022/0207729 | A1 | 6/2022 | Boyd et al. | |
| 2022/0236799 | A1 | 7/2022 | Berkner-Cieslicki et al. | |
| 2023/0194550 | A1 | 6/2023 | Louie et al. | |
| 2023/0314810 | A1 | 10/2023 | DeLapp et al. | |
| 2024/0024699 | A1 | 1/2024 | Emerson | |
| 2024/0053823 | A1 | 2/2024 | Berkner-Cieslicki et al. | |
| 2024/0075312 | A1 | 3/2024 | Cockrell et al. | |
| 2024/0184117 | A1 | 6/2024 | DeLapp et al. | |
| 2024/0293681 | A1 | 9/2024 | Hunter et al. | |
| 2024/0393591 | A1 | 11/2024 | DeLapp et al. | |
| 2025/0241793 | A1 | 7/2025 | Sigal et al. | |

OTHER PUBLICATIONS

Reynard M, Hanscom TA. Neodymium:yttrium-aluminum-garnet laser arteriotomy with embolectomy for central retinal artery occlusion. Am J Ophthalmol. Jan. 2004;137(1):196-8. doi: 10.1016s0002-9394(03)00817-1. PMID: 14700675.

* cited by examiner

SYSTEMS AND METHODS FOR AI-GATING PHOTOMODULATION

CROSS-REFERENCE TO RELATED APPLICATIONS

This is a priority patent document.

FIELD OF THE INVENTIONS

The present disclosure relates to systems and methods for controlling photonic emission and optical diagnostic acquisition using artificial intelligence. More specifically, the inventions concern an adaptive platform in which an AI-based predictive engine analyzes physiologic, optical, and environmental signals to determine optimal temporal conditions for delivering light or capturing diagnostic data from biological tissue. The technology integrates photomodulation, reflectance-based imaging, physiologic monitoring, and predictive control algorithms to create a unified system capable of dynamic, data-driven interaction with retinal and other tissues. The field encompasses medical imaging, therapeutic photobiomodulation, physiologic monitoring, machine-learning-guided diagnostics, and real-time closed-loop photonic control

BRIEF SUMMARY

In one aspect, a system for AI-Gated photonic interaction with ocular tissue, includes at least one optical modality configured to acquire data from ocular tissue, a processor configured to receive real-time and historical physiologic or optical input signals, a predictive model executed by the processor to forecast a future interval of physiologic stability of the ocular tissue based on temporal patterns in the real-time and historical physiologic or optical input signals, and a gating module configured to generate a control signal that regulates acquisition only during the future interval, where the control signal optimizes timing of imaging or light delivery without modifying intrinsic hardware resolution of the at least one optical modality.

In one aspect, a system for controlling ophthalmic imaging, includes at least one optical modality configured to acquire data from ocular tissue, a processor configured to receive real-time and historical physiologic or optical input signals, a predictive model executed by the processor to forecast a future interval of physiologic stability of the ocular tissue, and a gating module configured to generate a control signal that regulates acquisition only during the future interval, where the control signal optimizes timing of imaging or light delivery without modifying intrinsic hardware resolution of the at least one optical modality.

In one aspect, a system for AI-Gated photonic interaction with ocular tissue, includes at least one optical modality that acquires real-time input signals from the ocular tissue, one or more processors that receive the real-time input signals and store the real-time input signals as historical input signals, a predictive model executed by the one or more processors that forecasts a future interval of physiologic stability of the ocular tissue based on temporal patterns in the real-time input signals and the historical input signals, and a gating module executed by the one or more processors that generates a control signal that regulates acquisition only during the future interval, where the control signal optimizes operation of the at least one optical modality.

In one aspect, a system for AI-Gated control of photonic delivery, includes at least one optical modality that acquires real-time input signals from ocular tissue, one or more processors that receive the real-time input signals and store the real-time input signals as historical input signals, a predictive model executed by the one or more processors to forecast a future interval of physiologic stability of the ocular tissue based on temporal patterns in the real-time input signals and the historical input signals, and a gating module executed by the one or more processors that generates a control signal that regulates photonic output only during the future interval, where the control signal optimizes biologic receptivity or safety of the photonic delivery.

The gating module may be an external supervisory controller connected to the at least one optical modality through a digital trigger line. The real-time and historical physiologic or optical input signals may include reflectance signals. The predictive model may analyze temporal patterns to identify a stability interval defined by reflectance coherence plateau behavior. The gating module may suppress acquisition during predicted instability intervals. The post-acquisition outcomes may update the predictive model over time. The control signal may control the delivery of photomodulation energy. The prediction may be based on stabilization of autofluorescence intensity. The system may also include where at least one modality is directly gated and at least one modality is passively synchronized. The gating module may receive preview data without full-resolution imaging transfer. The ocular tissue may include a retina. The gating module may also be configured to generate a second control signal that regulates photonic output.

In one aspect, a system for controlling photonic delivery, includes at least one optical modality configured to acquire data from ocular tissue, a processor configured to receive real-time and historical physiologic input signals, a predictive model executed by the processor to forecast a future interval of physiologic stability of the ocular tissue, and a gating module configured to generate a control signal that regulates photonic output only during the future interval, where the control signal optimizes timing of imaging or light delivery without modifying intrinsic hardware resolution of the at least one optical modality.

In one aspect, a system for AI-Gated control of photonic delivery, includes at least one optical modality configured to acquire data from ocular tissue, a processor configured to receive real-time and historical physiologic input signals, a predictive model executed by the processor to forecast a future interval of physiologic stability of the ocular tissue based on temporal patterns in the real-time and historical physiologic input signals, and a gating module configured to generate a control signal that regulates photonic output only during the future interval, where the control signal optimizes biologic receptivity or safety of photonic delivery.

The real-time and historical physiologic input signals may include fixation stability. The system may also include two or more optical modalities, where the gating module synchronizes activation of the two or more optical modalities within the future interval. The two or more optical modalities include at least two of optical coherence tomography, optical coherence tomography angiography, fundus autofluorescence, hyperspectral imaging, near-infrared reflectance, or Raman spectroscopy. The photonic delivery may include pulsed light output. The predictive model may analyze temporal patterns to identify a stability interval defined by metabolic quieting. The gating module may also be configured to generate a second control signal that regulates acquisition.

In one aspect, a method for operating an ophthalmic imaging system, includes receiving real-time optical signals from ocular tissue, analyzing the real-time optical signals together with historical data to predict a future temporal interval of physiologic stability, generating a gating command based on the temporal interval, and regulating delivery only during the temporal interval to improve effective diagnostic performance.

The regulating may include delaying imaging acquisition. The regulating may include modulating imaging acquisition. The gating command may coordinate multimodal acquisition within a shared stability window. The method may also include where closed-loop refinement occurs across multiple clinical sessions. The method may also include where a proportion of diagnostically usable frames is increased by restricting acquisition to the temporal interval. The method may also include where forecasting is based on physiologic signals exhibiting transient plateau behavior. The method may also include where passive synchronization aligns ungated modalities to a timing of a gated modality. The ophthalmic imaging system may be applied to diagnosis or monitoring of inflammatory ophthalmic disease. The ophthalmic imaging system may be applied for diagnosis and monitoring of a disease and physiologic condition characterized by time-dependent variability in ophthalmic biomarkers, including optical, metabolic, vascular, inflammatory, neurodegenerative, and biomechanical biomarkers, the ophthalmic imaging system configured to detect inflammatory, metabolic, vascular, neurodegenerative, toxic, degenerative, and neoplastic conditions, including diabetes, glaucoma, keratoconus, macular degeneration, geographic atrophy, central serous chorioretinopathy, uveitis, optic neuropathy, retinal vascular disease, inherited retinal disease, retinal dystrophy, ocular tumors, intraocular neoplasia, toxic maculopathy, mitochondrial disorders, Alzheimer's disease, and Parkinson's disease. Other technical features may be readily apparent to one skilled in the art from the following figures, descriptions, and claims.

In one aspect, a non-transitory computer-readable medium storing instructions that, when executed by one or more processors, cause the instructions to receive physiologic inputs, forecast a future interval of stability using a predictive model, and issue a gating signal that controls photonic activation only during the future interval.

The photonic activation may be permitted only during predicted metabolic receptivity. Other technical features may be readily apparent to one skilled in the art from the following figures, descriptions, and claims.

BRIEF DESCRIPTION OF THE DRAWINGS

To easily identify the discussion of any particular element or act, the most significant digit or digits in a reference number refer to the figure number in which that element is first introduced.

TERMS AND DEFINITIONS

Figure 1:
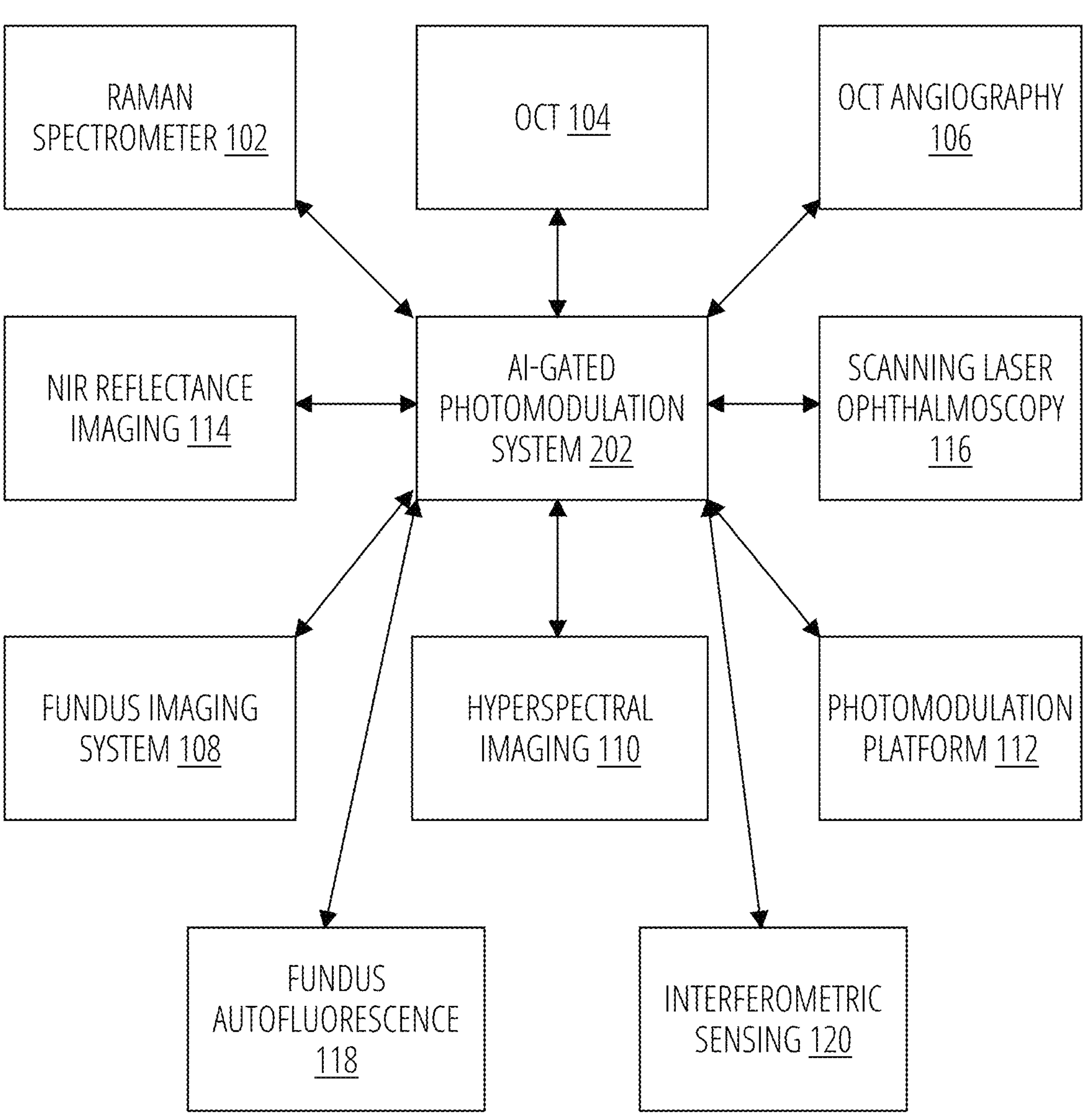
FIG. 1 illustrates the AI-Gated photomodulation system with some possible ophthalmic devices attached.

The following definitions are provided to clarify key concepts used throughout this document. These terms are intended to be interpreted broadly and are non-limiting unless explicitly limited by the claims. Where appropriate, definitions include functional and structural aspects to support multiple hardware, software, and physiologic embodiments.

AI-Gated Photomodulation. AI-Gated Photomodulation refers to the controlled delivery of therapeutic light, such as LED, laser, near-infrared, multispectral, or other photonic stimuli, during temporal intervals identified by an artificial intelligence model as optimal for tissue responsiveness, metabolic receptivity, or therapeutic effect. Unlike traditional continuous or technician-triggered illumination, AI-Gated Photomodulation is activated, suppressed, or modulated based on predictive assessments of physiologic coherence, mitochondrial stability, perfusion regularity, or optical clarity. This gated approach enhances safety, improves therapeutic efficiency, and allows photomodulation to be synchronized with dynamic tissue states, including retinal, neural, or systemic targets. Emission parameters may be dynamically adjusted by the predictive AI-Gating engine 210 based on feedback from the target tissue.

AI-Gating. AI-Gating refers to a temporal control system in which an artificial intelligence model analyzes real-time and historical physiologic, optical, or environmental data to determine when photonic energy should be delivered or when diagnostic acquisition should occur. The model evaluates continuously updated signals, such as reflectance stability, autofluorescence behavior, motion characteristics, and other biomarkers, to forecast short intervals in which tissue is predicted to be most receptive, stable, or diagnostically informative.

The AI-Gating engine 210 receives inputs through an acquisition layer, processes them through a predictive inference model, and generates a gating command that permits, delays, modulates, or suppresses system activity. The output may be binary or multi-level and may control timing, exposure structure, wavelength selection, or acquisition sequencing. The system operates within a dynamic feedback loop, updating predictions based on physiologic responses following each actuation.

As used throughout this specification, "AI-Gating" refers to the predictive control architecture disclosed herein in which an artificial intelligence model analyzes real-time and historical physiologic, optical, or device-state inputs to forecast a future interval during which imaging or photonic output is permitted, suppressed, delayed, or modulated.

For clarity, the terms "AI-Predictive System," "AI-Gated Predictive", "AI-Predictive," "AI-Gated," "AI-Gating," "AI-Gating engine," "AI-Gated Photomodulation," and "AI-Gated System" are used interchangeably in this application and refer to the same control architecture, unless explicitly stated otherwise. These terms are not intended to denote separate inventions or distinct embodiments, but merely linguistic variations describing the same system and method.

The definition is intended to encompass current and future implementations, including machine-learning, deep-learning, hybrid inferential, or rules-based models, whether deployed as integrated firmware, standalone hardware, or external supervisory modules.

Plural or descriptive variations of the foregoing terms (including "AI-Gated," "AI-Predictive," and "AI-Gating system") should be interpreted consistently with the definition of AI-Gating and are not intended to imply distinct structural or functional limitations.

Dynamic Feedback Loop. A dynamic feedback loop refers to the continuous cycle in which system outputs (e.g., light emission or imaging) generate new physiologic or optical responses, which are immediately analyzed and reintegrated into the AI-Gating model. This loop allows the system to continuously update predictions and adjust operation in real time. The feedback loop enables adaptive and responsive optimization of both therapeutic and diagnostic procedures.

Fundus Autofluorescence (FAF). Fundus Autofluorescence refers to an imaging modality that detects the naturally occurring fluorescent emission from retinal fluorophores, principally lipofuscin and related bisretinoid compounds in the retinal pigment epithelium (RPE), following excitation with visible or near-infrared light. FAF provides a spatial map of metabolic load, oxidative stress, and RPE health by quantifying emission intensity and distribution patterns. In the context of the AI-Gated photomodulation system 202, FAF serves as a dynamic metabolic biomarker whose short-term fluctuations and long-term trajectories can be incorporated into gating predictions to identify physiologically optimal windows for imaging or photomodulation and to detect early signs of retinal disease or toxic maculopathy.

Gating Signal. A gating signal refers to the output generated by the AI-Gating engine 210 that governs whether an action is executed, suppressed, delayed, or modified. The gating signal may be binary (on/off) or may operate over multiple levels or continuous values to control parameters such as emission intensity, wavelength, pulse segmentation, exposure timing, or frame capture. The gating output governs temporal control of illumination, frame capture, exposure duration, pulse segmentation, and inter-frame dark intervals, and may operate at millisecond-scale resolution. The gating signal coordinates system behavior with predicted optimal temporal windows.

Hyperspectral Reflectance. Hyperspectral Reflectance refers to the acquisition of tissue reflectance across a wide range of discrete wavelengths, generating a spectral profile that encodes information about oxygenation, chromophore concentration, scattering properties, biochemical composition, and mitochondrial metabolic state. Hyperspectral reflectance enables optical discrimination of biomolecules such as lipofuscin, melanin, carotenoids, hemoglobin derivatives, and amyloid species. Within the AI-Gated photomodulation system 202, hyperspectral reflectance contributes high-granularity spectral biomarkers whose temporal variability and pattern transitions are analyzed to predict optimal imaging windows and detect disease-related biochemical changes.

Imaging Modality. An imaging modality refers to any optical or photonic system used to acquire diagnostic information from tissue. This includes but is not limited to fundus reflectance imaging, near-infrared imaging, fundus autofluorescence, OCT, OCT angiography, scanning laser ophthalmoscopy, hyperspectral imaging, fluorescence imaging, interferometry, or confocal imaging. These modalities may operate independently, sequentially, or concurrently and may provide data for both diagnostic interpretation and AI-Gating control.

Loop Control. Loop control can be Closed or Open. Closed-Loop Control refers to a system architecture in which outputs (e.g., illumination, acquisition timing) are continuously adjusted based on feedback from measured physiologic or optical responses. The system updates predictions in real time to refine subsequent gating commands. Open-Loop Control refers to a system architecture in which outputs are issued without regard to real-time physiologic feedback, typically relying on fixed timing, standard acquisition schedules, or technician-triggered operation.

Mitochondrial Optical Biomarkers. Mitochondrial Optical Biomarkers refer to measurable optical signatures arising from mitochondrial structure, function, or metabolic state, detectable through modalities such as near-infrared reflectance, hyperspectral imaging, autofluorescence derivatives, or Raman spectroscopy. These biomarkers include changes in reflectance intensity, scattering uniformity, spectral shifts related to redox balance, chromophore absorption patterns, and Raman vibrational features associated with ATP production, oxidative stress, and membrane potential. In the context of the AI-Gated photomodulation system 202, mitochondrial optical biomarkers provide real-time and trend-level insight into cellular energetics and metabolic readiness, enabling the system to forecast physiologic intervals optimal for imaging or photomodulation.

Multimodel Fusion. Multimodal Fusion refers to the integration of data from two or more imaging or sensing modalities, such as OCT, OCT angiography, reflectance imaging, Raman spectroscopy, autofluorescence, hyperspectral reflectance, interferometry, or physiologic sensors, to generate a combined or higher-order signal used by the AI-Gated photomodulation system 202.

Optical Coherence Tomography (OCT). The term "Optical Coherence Tomography" or "OCT," as used in this specification and claims, means any present or future imaging technique that generates two-dimensional or three-dimensional images of a sample (including biological tissue) by detecting the interference between a reference optical path and light backscattered or reflected from the sample using coherent or partially coherent light. The term expressly includes, without limitation:

- all time-domain, frequency-domain (including spectral-domain and swept-source), and optical frequency-domain imaging (OFDI) systems;
- full-field OCT, line-field OCT, parallel OCT, and any non-scanning or partially scanning OCT architectures;
- high-resolution OCT, ultra-high-resolution OCT (UHR-OCT), high-resolution extended-source OCT (HRes-OCT), and any OCT system providing an axial resolution in tissue of 10 μm or better;
- visible-light OCT (vis-OCT), Doppler OCT, polarization-sensitive OCT (PS-OCT), spectroscopic OCT, phase-sensitive OCT, angiographic OCT (OCTA), and any functional or contrast-enhanced OCT variants;
- adaptive-optics OCT (AO-OCT), computational-adaptive-optics OCT, holographic OCT, and synthetic-aperture OCT;
- OCT systems using any interferometer topology (Michelson, Mach-Zehnder, common-path, self-referenced, or others), any light source (superluminescent diode, supercontinuum, femtosecond laser, swept laser, tunable laser, thermal light source, or future sources), and any detection scheme (balanced, single, dual, direct, or heterodyne); and
- any future optical coherence tomography modality, whether currently known or developed hereafter, that operates on the fundamental principle of measuring the echo time delay and/or magnitude of backscattered or reflected light through interferometry, regardless of wavelength, scanning mechanism, acquisition geometry, or data-processing method.

Optimal Temporal Window. An optimal temporal window refers to any period of time, ranging from milliseconds to several seconds, during which the system predicts that tissue or the environment is in a state most favorable for energy delivery or diagnostic capture. This window may correspond to retinal metabolic readiness, mitochondrial polarization, structural coherence, perfusion stability, motion quiescence, or optical clarity. The AI-Gating engine 210 identifies these windows by analyzing biomarkers and physiologic signals.

Photomodulation. Photomodulation refers to the interaction between delivered photonic energy and tissue in a way that alters cellular, biochemical, metabolic, or structural processes. Photomodulation may involve red or near-infrared light, low-level laser emission, multispectral patterns, or other forms of illumination that influence mitochondrial function, redox state, ATP production, perfusion, or cellular signaling. Photomodulation may be controlled or timed by the AI-Gating engine.

Photonic Emission Module. The photonic emission module refers to any collection of components configured to emit light or photonic energy for therapeutic, diagnostic, or monitoring purposes. This may include LEDs, low-level lasers, near-infrared emitters, multispectral arrays, structured illumination systems, pulse delivery architectures, or any combination thereof. The module may deliver continuous, pulsed, spectrally tuned, intensity-modulated, or spatially patterned emission. Its operational parameters may be controlled directly by the AI-Gating engine 210.

Predictive Model. A predictive model refers to any artificial intelligence, machine learning, statistical, or algorithmic system that analyzes current and historical data to forecast a future physiologic or optical event. This may include neural networks, temporal pattern-recognition systems, Bayesian inference, Kalman filtering, regression models, or hybrid computational architectures. The predictive model evaluates multi-dimensional inputs and generates forecasts that inform gating decisions.

Reflective Optical Biomarker. A reflective optical biomarker refers to any signal, feature, or measurable property derived from light that has interacted with tissue through reflection, scattering, absorption, emission, or interference. Examples include OCT backscatter, near-infrared reflectance, fundus reflectance, fundus autofluorescence texture, hyperspectral signatures, scattering coherence, and interferometric phase stability. These biomarkers may indicate tissue structure, metabolic state, mitochondrial behavior, perfusion dynamics, or microstructural integrity, and may be used by the AI-Gating engine as predictive indicators.

Tissue State or Physiologic State. A tissue state or physiologic state refers to the structural, metabolic, biochemical, or mechanical condition of the tissue at a given moment. Examples include mitochondrial activity level, redox balance, perfusion status, membrane integrity, fluid distribution, inflammatory activity, optical clarity, or motion stability. Tissue state may be inferred directly or indirectly from optical biomarkers and physiologic monitoring signals.

DETAILED DESCRIPTION

Optical imaging and photonic diagnostic technologies play a central role in the evaluation of biological tissue. In ophthalmology in particular, modalities such as fundus reflectance imaging, near-infrared reflectance, fundus autofluorescence, optical coherence tomography (OCT), OCT angiography (OCTA), scanning laser ophthalmoscopy (SLO), hyperspectral reflectance, and Raman spectroscopy provide complementary information about retinal structure, metabolism, perfusion, and biochemical composition. These modalities have transformed clinical diagnostics, yet they share a fundamental limitation: the quality and diagnostic value of acquired data depends strongly on transient physiologic states that fluctuate from moment to moment.

Physiologic variability, including fixation instability, tear-film oscillation, choriocapillaris micro-pulsatility, mitochondrial redox fluctuations, autofluorescence variance, and Raman spectral instability, can degrade the signal-to-noise ratio of optical acquisitions. Conventional systems operate in an open-loop manner, capturing images or spectra as soon as the device is activated, regardless of whether the tissue is optically coherent, metabolically stable, or in a physiologic state conducive to high-quality data acquisition. As a result, early or subtle biomarkers of disease may be obscured by noise, leading to inconsistent results across sessions and reduced sensitivity for detecting progression.

These limitations are particularly pronounced in retinal diseases such as age-related macular degeneration, drusen evolution, inherited retinal degeneration, toxic maculopathies, inflammatory disorders, and perfusion-related abnormalities. Many of the earliest pathophysiologic changes, mitochondrial stress, lipofuscin accumulation, oxidative load fluctuations, spectral shifts in drusen composition, perfusion irregularity, and microstructural changes near the ellipsoid zone, occur on time scales that are significantly shorter than the typical imaging session. Because conventional acquisition methods do not account for these physiologic rhythms, diagnostic sensitivity and reproducibility remain suboptimal.

Similar constraints affect photomodulation and other optical therapeutic interventions. Tissue responsiveness to photonic energy varies with mitochondrial potential, redox balance, metabolic readiness, and perfusion patterns. Yet current systems typically rely on technician timing or fixed illumination schedules, without consideration of whether tissue is receptive to treatment at a given moment. This can diminish therapeutic efficiency and introduce unnecessary exposure.

Despite advances in machine learning for image interpretation, classification, or segmentation, no existing system predicts when tissue will be in an optimal state for imaging or optical therapy. These systems do not forecast physiologic windows of stability or use such predictions to control the timing of light delivery or data acquisition. As a result, the underlying limitations of open-loop operation remain unaddressed.

Accordingly, there exists a need for a system that analyzes multimodal optical and physiologic inputs in real time; identifies patterns, trajectories, or cycles associated with physiologic readiness; predicts short intervals when imaging, spectroscopy, or photomodulation will be most effective; and controls acquisition timing or therapeutic delivery based on these predictions.

The present document addresses these needs by providing an AI-driven predictive gating architecture that synchronizes optical interrogation with physiologic coherence, thereby improving diagnostic sensitivity, reproducibility, and therapeutic precision across a wide range of biological tissues.

Definition of AI-Gating

As used throughout this document, AI-Gating refers to a predictive control architecture in which an artificial intelligence model analyzes real-time and historical physiologic, optical, and device-state inputs to forecast a future interval during which diagnostic imaging or therapeutic light delivery is expected to be most effective, safe, or physiologically coherent. Based on this prediction, the system generates a gating signal, a binary, multi-level, or continuously variable command, that permits, suppresses, delays, or modulates the operation of one or more system outputs, including imaging acquisition, spectral sampling, or photomodulation delivery.

The term AI-Gating is intended broadly to encompass present and future implementations, including machine-learning, deep-learning, hybrid inferential, rules-based, or adaptive predictive models, and applies equally to single-modality and multimodal configurations. The concept is not limited to a particular hardware platform, light source, wavelength, or device class, and extends to any system in which temporal control is based on physiologic readiness rather than fixed or technician-triggered timing.

For clarity, the AI-Gated photomodulation system 202 is not a denoising or post-processing algorithm. The system does not alter acquired image or spectral data. Instead, it improves effective diagnostic quality by preventing acquisition during predicted physiologic instability and permitting acquisition only during physiologic coherence intervals.

Standalone and Modular Configurations

AI-Gating may be implemented in several architectural forms, each relying on the same predictive control framework while differing only in physical configuration and the number of participating modalities. The AI-Gated photomodulation system 202 therefore encompasses integrated, standalone, modular, and hybrid embodiments, all of which apply the same gating logic to achieve physiologically synchronized diagnostic or therapeutic operation.

As shown in FIG. 1, the AI-Gated photomodulation system 202 can receive input from and send control instructions to one or more ophthalmic instruments. The ophthalmic instruments may include OCT 104, OCT angiography 106, fundus imaging systems 108, Raman spectrometers 102, hyperspectral imagings 110, NIR reflectance imaging 114, scanning laser ophthalmoscopy 116, fundus autofluorescence 118, interferometric sensing 120, or static photomodulation platforms 112.

Integrated/Native Platform Embodiments. In certain embodiments, AI-Gating is embedded directly into the core software or firmware of a newly designed multimodal ophthalmic system. In this configuration, the AI-Gating engine functions as a native supervisory layer that governs the structural, vascular, biochemical, and photomodulation subsystems through unified timing logic. The AI-Gated photomodulation system 202 continuously receives optical or physiologic inputs from its internal sensors, evaluates temporal biomarkers, generates predictive models of physiologic readiness, and uses these predictions to control the timing and characteristics of acquisition or light delivery. Because the gating algorithm is implemented within the native control architecture, no additional hardware modules are required, and the system behaves as a fully integrated platform.

Standalone AI-Gating Device Embodiments. In other embodiments, the AI-Gated photomodulation system 202 is implemented as a complete standalone AI-Gating device. This embodiment includes an integrated photonic emission module, a physiologic sensing subsystem, a predictive AI-Gating engine 210, and a control interface configured to deliver diagnostic or therapeutic output through an integrated optical port or handpiece. The standalone system receives optical or physiologic input from its own sensors, extracts temporal biomarkers, forecasts upcoming windows of physiologic stability, and determines exactly when acquisition or illumination should be permitted, delayed, modulated, or suppressed.

Because all sensing, computation, and light delivery components may be housed within the same enclosure, the standalone device requires no external hardware to operate. It may function independently for photomodulation or diagnostic tasks, or it may serve as a supervisory controller when optionally connected to compatible ophthalmic instruments.

External Modular AI-Gating Controller Embodiments. Another class of embodiments provides AI-Gating as an external supervisory module that can be connected to existing clinical devices. In this configuration, the AI-Gating engine 210 communicates with one or more ophthalmic instruments, such as OCT 104, OCT angiography 106, fundus imaging systems 108, Raman spectrometers 102, hyperspectral imagings 110, NIR reflectance imaging 114, scanning laser ophthalmoscopy 116, fundus autofluorescence 118, interferometric sensing 120, or static photomodulation platforms 112, using digital trigger lines, wired or wireless data pathways, or manufacturer-supplied application programming interfaces.

This modular arrangement allows legacy instruments to participate in predictive physiologic synchronization without refurbishment or modification. The external controller receives preview signals or physiologic indicators from the connected devices, computes predicted stability intervals, and issues gating commands that control the timing of imaging or photonic output. The modular unit may be deployed as a tabletop console, a slit-lamp-mounted accessory, a portable plug-in module, or any comparable external interface capable of supervisory control.

Hybrid Embodiments. Hybrid embodiments are also contemplated. In these configurations, one or more devices may receive direct gating commands from the AI-Gating engine, while additional devices are passively synchronized using shared timing predictions, preview frames, or periodic synchronization signals. For example, OCT and Raman spectroscopy may be actively gated, while fundus autofluorescence or reflectance imaging may operate during the same predicted intervals without requiring a dedicated gating connection. This approach allows the system to accommodate a wide range of device capabilities and integration levels, enabling seamless participation even for partially compatible instruments.

Unified AI-Gating Engine Across All Embodiments. All embodiments, integrated, standalone, modular, and hybrid, utilize the same AI-Gating engine 210. The underlying algorithm does not change; the distinction lies only in the number and type of modalities providing input signals and the number and type of outputs regulated by the gating signal. This consistency allows OEMs, clinics, and future device generations to adopt the AI-Gated photomodulation system 202 without requiring changes to the predictive architecture or its operational logic.

Safety and Exposure Compliance Across Embodiments. Regardless of the physical embodiment, the AI-Gated photomodulation system 202 does not exceed or bypass device-specific safety limits. All photonic delivery remains constrained by the wavelength, fluence, irradiance, duty cycle, pulse structure, cumulative exposure, and session duration permitted by the corresponding hardware platform in accordance with ANSI and IEC safety standards. The system optimizes when energy is delivered, not how much energy a device is allowed to generate. This ensures compatibility with existing emission safety boundaries while enhancing therapeutic and diagnostic precision.

Benefits Provided by AI-Gating

The disclosed architecture improves performance through temporal optimization rather than hardware modification.

By synchronizing system activity to predicted intervals of physiologic stability, AI-Gating increases the proportion of diagnostically usable frames and reduces motion artifact, segmentation variability, and spectral noise. Effective diagnostic resolution is enhanced even though the intrinsic axial or transverse resolution of the device remains unchanged.

Physiologically synchronized acquisition also increases biomarker sensitivity, allowing detection of subtle structural, metabolic, and biochemical signatures that may be obscured when imaging occurs during random instability. Longitudinal reproducibility improves because data are captured under consistent physiologic conditions, supporting more reliable disease monitoring and treatment assessment.

In therapeutic applications, AI-Gating restricts photomodulation to intervals of predicted metabolic receptivity and suppresses delivery during physiologic vulnerability, reducing unnecessary exposure while maintaining or enhancing therapeutic effect. These benefits apply equally to current systems and to future high-resolution or extended-source platforms without requiring redesign of the underlying hardware.

Unlike existing methods, the disclosed architecture suppresses or modulates acquisition during predicted instability and permits operation only during biologically advantageous intervals. Cross-modal synchronization allows two or more modalities to operate within the same predicted window, generating coherent multimodal datasets that are not achievable with open-loop systems.

A closed-loop adaptive component further distinguishes the system: discrepancies between predicted and observed responses are re-incorporated into the model across minutes, sessions, or longitudinal visits, enabling progressive refinement and patient-specific adaptation.

No existing ophthalmic imaging or photomodulation systems perform prediction-based temporal control, nor do they suppress or delay acquisition based on anticipated physiologic instability, nor synchronize multiple modalities to operate within the same forecasted physiologic window.

This document provides detailed descriptions of input acquisition, feature extraction, temporal biomarker reconstruction, predictive inference, gating decision logic, output actuation, and closed-loop feedback. The system may be implemented using commercially available processors, machine-learning frameworks, and device-communication interfaces.

The system is supported by multiple embodiments, including single-modality systems in which only one device receives gating control, multimodal platforms in which several devices are synchronized within the same physiologic window, and hybrid configurations in which certain instruments contribute data without being directly controlled. The system does not require a specific model architecture; any machine-learning, deep-learning, Bayesian, or rules-based predictor capable of forecasting physiologic stability may be used.

In certain embodiments, the AI-Gated photomodulation system 202 operates without requiring real-time spectral reconstruction and without the use of any invasive sensors. The AI-Gating engine 210 relies on readily obtainable optical or physiologic signals, such as reflectance stability, autofluorescence uniformity, motion quiescence, or perfusion regularity, as predictive inputs rather than reconstructed biochemical spectra. Because gating decisions are based on temporal pattern analysis rather than full spectral decomposition, the system avoids the computational burden, latency, and hardware complexity associated with real-time spectral processing.

Similarly, no intraocular, implantable, or contact-based sensors are required. All physiologic indicators used for prediction may be derived from non-invasive measurements obtained through existing ophthalmic imaging pathways, including OCT, fundus imaging, OCT angiography, or external eye-tracking streams. This configuration preserves clinical workflow, eliminates procedural risk, and allows the system to be implemented with current diagnostic instruments without modification of the patient interface.

Applications for Ophthalmic Use

AI-Gating is particularly well-suited for ophthalmic disorders in which physiologic conditions fluctuate over milliseconds to minutes. In retinal disease, transient windows of motion stillness, metabolic quieting, spectral stabilization, and perfusion regularity determine the clarity and diagnostic value of imaging. AI-Gated acquisition enables improved assessment of conditions, including age-related macular degeneration, inherited retinal degenerations, toxic maculopathies, uveitis, optic neuropathies, and glaucoma-associated structural and vascular changes.

When integrated with photomodulation systems, AI-Gating delivers therapeutic light only during intervals of predicted metabolic receptivity, improving precision relative to static dosing while reducing unnecessary exposure. As a standalone analytic layer, AI-Gating may interpret temporal biomarkers without controlling imaging hardware, providing predictive insight for risk stratification, treatment timing, or disease progression monitoring.

1.0 AI-Gating and Dynamic Retinal Physiology

Nearly every aspect of retinal structure and metabolism leaves a measurable imprint on reflected or emitted light. Whether arising from photoreceptor outer segments, mitochondrial redox oscillations, RPE lipofuscin load, melanin distribution, drusen biochemistry, or choriocapillaris perfusion, these reflectance-encoded signals collectively provide a dynamic optical portrait of tissue health. Importantly, they also fluctuate over short time scales, creating transient intervals in which structural coherence, metabolic steadiness, or vascular regularity are momentarily optimized.

Traditional ophthalmic instruments already rely on these reflectance behaviors, but they do so in a passive, static manner: OCT measures interferometric backscatter, OCTA detects decorrelation in reflected signals, FAF interprets fluorescence shaped by reflectance geometry, NIR imaging captures deep reflectance from melanin and mitochondria, and hyperspectral imaging parses wavelength-dependent reflectance to infer biochemical states. Each of these devices provides a distinct, modality-specific window into the retina, yet all share a common foundational mechanism, the analysis of photons that have interacted with tissue. Examples of instruments in common use that rely of reflected to analyze ocular tissue are shown in the following table.

TABLE 1

Comparative Analysis of Reflectance-Based Ophthalmic Technologies

| Instrument/ System | How the Device Uses Reflectance | Type of Light/ Signal Detected | Primary Clinical or Physiologic Information Obtained | Why It Is Fundamentally Reflectance-Based | Unique Features Compared to Others |
|---|---|---|---|---|---|
| AI-Gating | Continuously monitors reflectance, scattering, autofluorescence, and related physiologic optical signals in real time; interprets and predicts the optimal temporal window for photomodulation or diagnostic capture | Inputs derived from OCT, NIR, SLO, FAF, hyperspectral sensors, or native optical channels; output consists of timed, gated photonic pulses | Predictive evaluation of mitochondrial readiness, structural coherence, vascular stability, and optimal conditions for high-clarity imaging | All gating decisions arise from temporal patterns in reflected or emitted photons, making the system a reflectance-driven predictive engine | Converts reflectance from a passive measurement into a dynamic control variable, timing light delivery and imaging according to physiologic optical cues |
| Spectral-Domain OCT | Uses interferometric detection of backscattered light to create depth-resolved reflectance profiles | Near-infrared broadband illumination (~800-900 nm); low-coherence interferometric return | Photoreceptor layer integrity, ellipsoid zone structure, RPE status, drusen, subretinal fluid | Every voxel represents a reflectance amplitude at a specific depth; OCT is fluidessentially a 3D reflectometer | Provides micron-scale depth sectioning (“optical biopsy”) |
| OCT Angiography | Detects frame-to-frame variations in reflectance caused by moving erythrocytes | Same NIR OCT source; measures decorrelation of backscattered light | Capillary plexus integrity, choriocapillaris perfusion, ischemia | Flow is inferred entirely from temporal reflectance fluctuations | Adds functional (flow) information to structural OCT using reflectance dynamics |
| Fundus Photography | Captures broadband visible-light reflectance from retinal and choroidal surfaces | White or RGB illumination; reflected visible spectrum | Pigment changes, drusen, hemorrhages, vessels, optic nerve | The photograph is a direct two-dimensional reflectance map | Provides intuitive macroscopic surface anatomy |
| Near-Infrared Reflectance (NIR) | Detects deep-penetrating NIR reflectance from melanin, mitochondria, and choroidal structures | 820-870 nm near-infrared light | Early atrophic changes, subtle photoreceptor disruptions, melanin patterns | Penetration depth and melanin—mitochondria interaction are reflectance-driven | Reveals changes invisible to visible-spectrum imaging |
| Fundus Autofluorescence (FAF) | Captures emission from lipofuscin and bisretinoids but depends on reflectance for alignment, illumination, and spatial registration | Blue or green excitation; emission captured as autofluorescence | RPE stress, lipofuscin burden, zones of atrophy | Even fluorescence-based imaging requires stable reflectance for accurate formation | Provides metabolic, rather than structural, information |
| Scanning Laser Ophthalmoscopy (SLO) | Measures point-by-point reflectance of a raster-scanned laser beam | Single-wavelength coherent laser light | Nerve fiber layer contrast, pigment patterns, synchronous functional mapping | Fundamentally coherent reflectance sampling | Enables confocal imaging and integration with microperimetry |
| Multispectral/ Hyperspectral Imaging | Measures reflectance across many discrete wavelengths | Broadband or tunable illumination; wavelength-resolved reflectance | Oxygenation, metabolic gradients, early degenerative signatures | Each spectral band reflects a unique tissue-photon interaction | Converts reflectance into biochemical or metabolic fingerprints |
| Adaptive Optics Retinal Imaging | Applies wavefront correction to measure high- | Usually NIR reflectance with corrected | Photoreceptor mosaics, microvascular | Reflectance captured with near-cellular | Highest-resolution reflectance |

TABLE 1-continued

Comparative Analysis of Reflectance-Based Ophthalmic Technologies

| Instrument/ System | How the Device Uses Reflectance | Type of Light/ Signal Detected | Primary Clinical or Physiologic Information Obtained | Why It Is Fundamentally Reflectance-Based | Unique Features Compared to Others |
|---|---|---|---|---|---|
| | resolution reflectance from individual cones and fine microvasculature | aberrations | anomalies | spatial fidelity | modality available in vivo |

Table 1 presents a comparative overview of the principal ophthalmic technologies that acquire structural, metabolic, or physiologic information through reflectance or emission of light. Although each instrument employs distinct illumination sources, wavelengths, and detection strategies, they all rely on the same fundamental principle: retinal tissue conveys its biologic state through the behavior of returning photons.

Each of these modalities provides data that is useful both diagnostically and as a temporal biomarker, a real-time indicator of physiologic coherence, stability, or readiness for imaging or therapy.

The distinguishing feature of AI-Gating is its ability to interpret the temporal dynamics of reflectance in real time and to use these patterns as a physiologic guide for the timing of photomodulation and diagnostic acquisition.

AI-Gating extends this principle further by transforming reflectance from a purely diagnostic phenomenon into a dynamic control variable. Instead of simply recording reflectance or fluorescence, the AI-Gated photomodulation system 202 evaluates their temporal patterns, extracts physiologic meaning, forecasts impending stability intervals, and uses those forecasts to govern the timing of imaging or photomodulation itself. In this framework, reflectance is not merely a signal to be captured; it becomes the predictive substrate upon which the entire system operates.

To contextualize how AI-Gating builds upon, integrates, and transcends conventional reflectance-based technologies. Table 1 compares the major ophthalmic imaging modalities in terms of their reliance on reflectance, the type of information they yield, and the unique role that AI-Gating plays within this shared optical ecosystem.

2. Retinal Temporal Biomarkers and their Significance for AI-Gating and Photomodulation 2.1. Overview of Dynamic Retinal Physiology The retina is an optically and metabolically active tissue whose physiologic state is continuously revealed through the way it reflects, scatters, absorbs, and emits light. Every modality that interacts with retinal tissue, whether OCT, near-infrared reflectance, fundus autofluorescence, Raman spectroscopy, hyperspectral imaging, or confocal scanning ophthalmoscopy, captures real-time variations in these optical behaviors. These fluctuations are not random; they encode the moment-to-moment metabolic, structural, and vascular conditions of the retina. Because these optical signatures evolve rapidly, they form a class of temporal biomarkers capable of signaling when tissue is transiently more stable, more coherent, or more metabolically receptive to imaging or photomodulation.

2.2. Reflectance as a Dynamic Physiologic Signature

Reflectance imaging is often treated as though it produces a steady, repeatable signal, yet the retinal photon field is inherently dynamic. Reflected light varies with subtle alterations in outer-segment geometry, tear-film behavior, eye motion, mitochondrial scattering, RPE lipofuscin activity, and melanin-driven absorption or backscatter. As these factors oscillate, the optical field alternates between moments of stability and moments of noise. These fluctuations reveal when tissue enters brief physiologic states that are more favorable for precise imaging or more responsive to red and near-infrared photomodulation.

2.3. Temporal Biomarkers as the Basis for AI-Gating

AI-Gating for ophthalmic applications is founded on the principle that retinal biomarkers are most informative in their temporal behavior rather than in isolated measurements. Instead of interpreting single reflectance values or single-frame images, the AI-Gated photomodulation system 202 processes how optical signatures evolve across spans of seconds or subseconds. By analyzing temporal trends in structural coherence, metabolic quieting, perfusion regularity, motion reduction, scattering uniformity, autofluorescence stability, and biochemical plateau states, the AI-Gated photomodulation system 202 identifies short intervals during which the tissue itself becomes an optimal substrate for imaging or therapy.

Because these temporal biomarkers arise from many different modalities, each instrument contributes a distinct dimension of physiologic information. Reflectance-based modalities reveal optical clarity, scattering behavior, and layer integrity. Autofluorescence imaging reveals fluctuations in RPE metabolic stress. OCT highlights microstructural coherence and outer-retinal stability. OCTA captures variations in capillary flow and perfusion regularity.

Raman spectroscopy measures biochemical oscillations, including those related to mitochondria, lipids, and amyloid. Hyperspectral imaging maps shifts in oxygenation and chromophore distribution. Motion sensors characterize fixation stability and blink cycles, while environmental sensors provide context for ambient illumination and noise sources. When these data streams are combined, they form a multilayered temporal landscape that the AI interprets to determine when the tissue is entering a physiologically receptive interval.

2.4. Biologic Interpretation of Temporal Biomarker Fluctuations

In a healthy retina, the temporal evolution of biomarkers tends to follow orderly patterns: mitochondria maintain regular metabolic cycles, the RPE shows predictable phagocytic rhythms, photoreceptors maintain stable outer-segment geometry, and perfusion patterns remain synchronized with metabolic demand. In states of disease or stress, these ordered patterns fragment.

Mitochondria demonstrate periods of dysregulation, outer-retinal morphology becomes unstable, oxidative stress causes shifts in autofluorescence signatures, vascular supply fluctuates, and deeper layers exhibit increased scattering noise. Importantly, none of these signatures are static. They oscillate because the underlying biology oscillates, membrane potentials rise and fall, metabolic load changes, mitochondrial redox states shift, and the RPE's phagocytic activity waxes and wanes.

AI-Gating interprets these oscillations and uses them to discriminate between intervals during which the retina is likely to produce high-fidelity data and intervals when noise, instability, or metabolic stress would degrade measurement quality. In doing so, the AI-Gated photomodulation system 202 converts ordinary biomarkers into predictive signals that govern when the device interacts with tissue.

2.5. AI-Gating and Photomodulation of the Retina

Photobiomodulation acts primarily on mitochondrial chromophores, especially cytochrome c oxidase, whose responsiveness varies according to the instantaneous redox state, membrane potential, and intracellular environment. A therapeutic pulse delivered at a moment of mitochondrial polarization or metabolic readiness can meaningfully enhance ATP generation and oxidative balance. The same pulse delivered during a period of stress or instability may produce a diminished response or add unnecessary noise to ongoing diagnostic acquisition.

AI-Gating identifies these physiologic windows by monitoring the temporal signatures that correlate with mitochondrial quieting, RPE metabolic stabilization, and improved structural or perfusion coherence. It recognizes when the ellipsoid zone shows increased reflectance stability, when autofluorescence patterns become less granular, when OCT scattering noise diminishes, or when Raman spectra enter biochemical plateau states. By predicting these near-future intervals of receptivity, the system can time photomodulation in a way that matches the retina's intrinsic biological rhythms.

2.6. Transition From Descriptive Biomarkers to Predictive Control

Conventional instruments treat retinal biomarkers as static descriptors. AI-Gating transforms them into actionable temporal predictors. Instead of reporting "what the retina looks like," the biomarkers in this AI-Gated photomodulation system 202 help determine when imaging or therapy should occur. This shift enables the device to function as a closed-loop architecture in which photonic energy, exposure parameters, and acquisition timing are governed by the real-time physiologic state of the tissue rather than by technician-driven timing or fixed acquisition schedules.

This adaptive approach improves the consistency, clarity, and biologic impact of both imaging and photomodulation. It also ensures that device interactions are anchored in physiologic relevance rather than operational convenience.

3.0. Universality Across Retinal Conditions

The temporal biomarker framework is inherently generalizable. Retinal tissue, whether healthy, stressed, inflamed, degenerating, or affected by toxic or metabolic injury, continuously expresses its physiologic state through variations in reflected and emitted light. These patterns remain interpretable regardless of the underlying disease process. As a result, the AI-Gating approach is broadly applicable across disorders including age-related macular degeneration, inherited retinal disease, inflammatory conditions, ischemic retinopathies, and drug-induced toxicities.

Subsequent sections of this document map these general principles onto specific disease entities, but the unifying concept remains constant: the retina reveals its biology through light, and closed-loop processing with AI-Gating elevates this information from a descriptive signal to a predictive control mechanism that directs imaging and photomodulation with unprecedented precision.

3.1 Closed-Loop Biomarker Analysis and Photomodulation

Conventional systems operate in an open-loop manner, capturing images or spectra as soon as the device is activated, regardless of whether the tissue is optically coherent, metabolically stable, or in a physiologic state conducive to high-quality data acquisition. As a result, early or subtle biomarkers of disease may be obscured by noise, leading to inconsistent results across sessions and reduced sensitivity for detecting progression.

These limitations are particularly pronounced in retinal diseases such as age-related macular degeneration, drusen evolution, inherited retinal degeneration, toxic maculopathies, inflammatory disorders, and perfusion-related abnormalities. Many of the earliest pathophysiologic changes, mitochondrial stress, lipofuscin accumulation, oxidative load fluctuations, spectral shifts in drusen composition, perfusion irregularity, and microstructural changes near the ellipsoid zone, occur on time scales that are significantly shorter than the typical imaging session. Because conventional acquisition methods do not account for these physiologic rhythms, diagnostic sensitivity and reproducibility remain suboptimal.

Similar constraints affect photomodulation and other optical therapeutic interventions. Tissue responsiveness to photonic energy varies with mitochondrial potential, redox balance, metabolic readiness, and perfusion patterns.

3.2 System Architecture

The AI-Gated photomodulation system 202 is constructed as an integrated photonic and diagnostic platform composed of coordinated hardware and software subsystems that operate within a unified predictive control framework. Rather than functioning as an open-loop instrument that assumes tissue stability, the AI-Gated photomodulation system 202 behaves as an intelligent temporal control network that continuously acquires, analyzes, and acts upon physiologic information to determine when imaging, spectroscopy, or photomodulation should occur.

Figure 2:
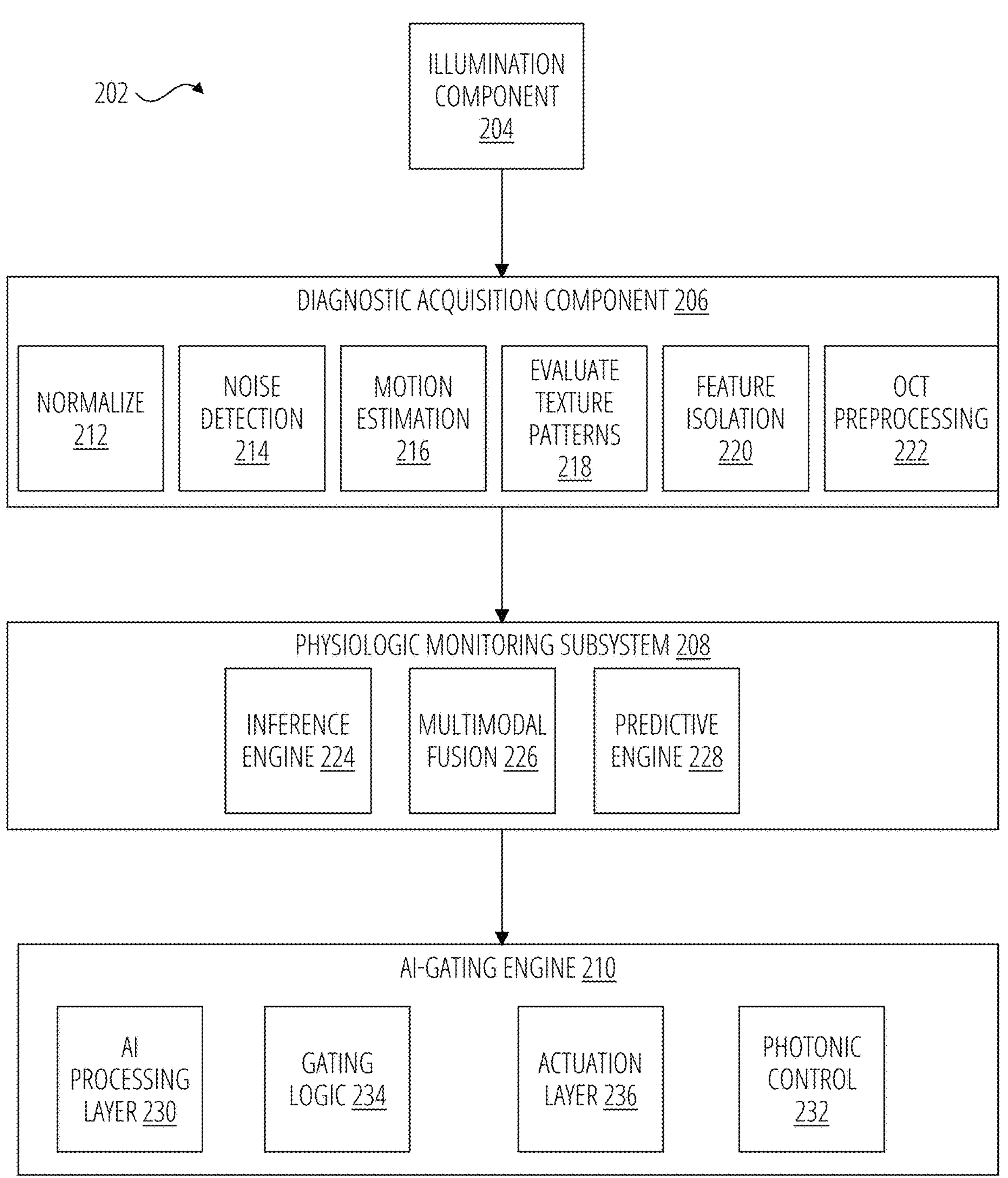
FIG. 2 shows a flowchart of the AI-Gated ophthalmic photomodulation system.

As seen in FIG. 2, at the highest level, the architecture includes a photonic emission module 204, an optical imaging and sensing module 206, a physiologic monitoring subsystem 208, and an AI-Gating engine 210 that governs the timing and characteristics of all diagnostic and therapeutic activity. These components are connected through a closed-loop feedback pathway in which each photonic or imaging event generates new optical and physiologic data, allowing the AI-Gated photomodulation system 202 to refine its internal predictions in real time.

The photonic emission module (or illumination component 204) contains one or more light sources capable of delivering energy in continuous, pulsed, or temporally modulated formats. Suitable emitters may include LEDs, laser diodes, multispectral arrays, near-infrared sources, or other photonic devices configured for illumination of biological tissue. Parameters such as wavelength, intensity, duty cycle, pulse structure, and temporal segmentation may be dynamically adjusted according to commands issued by the AI-Gating engine 210, permitting the system to synchronize light delivery with predicted periods of metabolic receptivity or motion stillness.

In various embodiments, the photonic emission module of the AI-Gated photomodulation system 202 may employ one or more light sources 204 emitting in the visible and/or near-infrared spectrum, for example, within a range of approximately 400 nm to 1,100 nm, subject to applicable maximum permissible exposure (MPE) limits. Exemplary implementations may include narrow-band or multi-band emitters centered near commonly used photobiomodulation wavelengths such as 590 nm, 660 nm, and 850 nm, as well as other wavelengths or combinations thereof selected to achieve desired retinal or choroidal irradiance profiles.

The use of specific numerical wavelengths in this document, including 590 nm, 660 nm, and 850 nm, is illustrative and non-limiting, and does not imply any particular regulatory status, therapeutic claim, or clinical indication. Selection of wavelength, power, fluence, duty cycle, and exposure duration in the disclosed system is independent of regulatory indication and is intended to be constrained in practice by applicable safety standards (e.g., ANSI MPE limits) and any labeling restrictions of the host device.

The optical imaging and sensing module (or diagnostic acquisition component 206) acquires reflected, scattered, or emissive optical signals from the target tissue. This module may incorporate fundus reflectance or near-infrared imaging, fundus autofluorescence, optical coherence tomography, OCT angiography, scanning laser ophthalmoscopy, hyperspectral imaging, Raman spectroscopy, interferometric sensing, or any combination thereof. Each modality supplies conventional diagnostic information, such as structural boundaries, biochemical signatures, or perfusion maps, while simultaneously generating time-varying optical biomarkers that reflect the physiologic state of the tissue.

A physiologic monitoring subsystem 208 provides continuous assessment of mechanical and temporal stability. Measurements may include eye tracking, blink and microsaccade detection, fixation and tremor analysis, and retinal displacement mapping. These data ensure that diagnostic capture and photonic exposure occur only under conditions that support accurate measurement and safe delivery.

At the center of the architecture is the AI-Gating engine 210, which receives optical and physiologic inputs and applies machine-learning models, temporal pattern recognition, or computational inference techniques to forecast short-range physiologic futures. The AI-Gating engine 210 identifies intervals in which the tissue is predicted to demonstrate structural coherence, spectral stability, perfusion regularity, or motion quiescence, and generates a gating signal that may permit, delay, modulate, or suppress acquisition or photonic output. This predictive control transforms fixed-timing ophthalmic systems into adaptive platforms that align their operation with the native physiologic behavior of living tissue.

The architecture may operate as a continuously updating closed-loop system. Each imaging or photomodulation event produces new responses that are captured by the sensing modules and re-incorporated into the AI-Gating engine 210, refining subsequent predictions over seconds, sessions, or longitudinal visits. As a result, the AI-Gated photomodulation system 202 becomes progressively tailored to individual patient physiology.

The optical imaging and sensing module 206 is responsible for acquiring reflective or emissive optical signals from the target tissue. This module may include signals from a fundus imaging system 108, NIR reflectance imaging 114 (near-infrared), fundus autofluorescence 118 (FAF), optical coherence tomography (OCT) 104, OCT angiography (OCTA) 106, scanning laser ophthalmoscopy 116 (SLO), hyperspectral imaging 110, Raman spectrometer 102, interferometric sensing 120, or any combination thereof. Each modality provides raw or processed optical data that support two functions: (1) conventional diagnostic assessment based on structural, metabolic, vascular, or biochemical features, and (2) generation of reflective or emissive optical biomarkers that characterize the tissue's physiologic, metabolic, or perfusion state in real time.

The modular design permits deployment as a fully integrated platform, as an external supervisory controller interfacing with existing devices, or as a hybrid configuration in which certain modalities are directly gated while others are passively synchronized. The AI-Gated photomodulation system 202 may not require replacement or refurbishment of participating devices; any instrument capable of transmitting or receiving timing or status information may be incorporated. The architecture is adaptable to future sensors, upgraded light sources, or enhanced AI models without alteration of the core design.

Accordingly, the AI-Gated photomodulation system 202 enables adaptive, data-driven control of photonic interaction with tissue, improving precision, safety, and physiologic specificity across diagnostic and therapeutic applications.

The AI-Gated photomodulation system 202 provides a unified photonic and diagnostic platform that uses artificial intelligence to determine optimal temporal conditions for delivering light to biological tissue or acquiring diagnostic data, as seen in FIG. 2. The AI-Gated photomodulation system 202 integrates one or more illumination sources 204, one or more optical sensing modalities 206, and a physiologic monitoring subsystem 208, all coordinated by a predictive AI-Gating engine 210 that interprets real-time tissue-derived signals to control when and how the system emits light or captures images.

The illumination component 204 may include light-emitting diodes, laser sources, near-infrared emitters, multispectral arrays, or any device configured to deliver photonic energy. The diagnostic acquisition component 206 may include reflectance-based imaging, fluorescence-based imaging, tomographic imaging, interferometric sensing, or any optical technique that measures light after its interaction with tissue. These imaging and sensing modalities not only generate diagnostic information but also produce optical biomarkers, such as reflectance stability, scattering behavior, spectral signatures, vascular-flow dynamics, or fluorescence patterns, that characterize the physiologic condition of the tissue in real time.

The diagnostic acquisition component 206 may incorporate eye tracking, motion analysis, blink detection, fixation assessment, or related sensors that determine whether the tissue environment is sufficiently stable for precise energy delivery or measurement. Any combination of these modalities may operate independently or simultaneously, and the platform accommodates interchangeable hardware configurations.

At the center of the system is the AI-Gating engine 210, which processes raw and derived signals from the optical and physiologic inputs. Using temporal modeling, pattern recognition, machine learning, or other computational methods, the AI-Gating engine 210 forecasts short intervals during which tissue is predicted to be in a state most favorable for photonic interaction or diagnostic capture. These predictions may correspond to changes in mitochondrial activity, structural coherence, perfusion behavior, metabolic status, motion stability, or any other physiologic variable manifested through optical signatures. Based on these forecasts, the AI-Gated photomodulation system 202 selectively opens or closes a photonic gate, modulates emission parameters, or triggers high-fidelity imaging sequences.

By linking energy delivery and diagnostic acquisition to predicted physiologic readiness, the AI-Gated photomodulation system 202 enhances precision, reduces noise, minimizes exposure outside optimal conditions, and improves the reliability and interpretability of resulting data. The system may function as a diagnostic tool, a therapeutic photomodulation device, a monitoring instrument, or a combination thereof. It may be configured for retinal applications and a variety of other non-ophthalmic applications that comprise neurologic tissue assessment, dermatologic phototherapy, or any context in which tissue-derived optical signals inform photonic interaction.

The architecture may be modular and extensible, supporting the integration of future sensors, additional light sources, and alternative AI models. The AI-Gated photomodulation system 202 may accommodate a wide range of wavelengths, pulse structures, sensor types, and computational approaches. Its components may be implemented in hardware, software, firmware, or any combination thereof, and may be deployed in clinical, research, or consumer settings.

3.3 Input Acquisition Layer as a Standalone and Integrative Platform

The diagnostic acquisition component 206 operates as the sensory foundation of the AI-Gated photomodulation system 202 and is capable of functioning as a fully autonomous predictive engine or as an embedded module within existing ophthalmic platforms. In its standalone embodiment, the diagnostic acquisition component 206 gathers native optical signals, such as variations in reflected light, low-level scattering patterns, or passive ambient signatures, and interprets these temporal fluctuations without relying on any external imaging infrastructure. In this configuration, the AI-Gated photomodulation system 202 functions as a self-contained physiologic monitor, detecting dynamic changes in tissue coherence, mitochondrial fluctuation, and microstructural stability exclusively through its own optical and sensing channels.

However, the diagnostic acquisition component 206*r* may also operate in integrated embodiments in which it receives incoming data from familiar clinical instruments. Reflectance-based modalities such as fundus imaging, near-infrared reflectance, and scanning laser ophthalmoscopy can supply moment-to-moment variations in backscattered light. Autofluorescence imaging contributes metabolic information from lipofuscin and bisretinoid emissions. OCT provides depth-resolved structural signatures that fluctuate subtly with photoreceptor alignment and outer-retinal geometry, while OCT angiography contributes perfusion-sensitive information through decorrelation patterns generated by erythrocyte motion. Raman spectroscopy offers biochemical specificity through its molecular fingerprints, and hyperspectral instruments provide wavelength-resolved insights into oxygenation and chromophore distribution.

In all embodiments, whether standalone or integrated, the diagnostic acquisition component 206 continuously collects optical, physiologic, and environmental signals that serve dual functions: conventional diagnostic data and temporal biomarkers of physiologic stability. Even minute fluctuations in reflectance, autofluorescence, interferometric coherence, vascular regularity, Raman biochemical signatures, or hyperspectral gradients provide real-time indicators of metabolic order, structural quieting, perfusion steadiness, or optical clarity.

These signals need not originate from any particular modality. A minimal hardware configuration can function as a predictive gate by analyzing simple reflectance and motion channels. A more complex configuration can fuse multi-instrument streams into a unified temporal signature. The architecture is therefore inherently modular, permitting a range of embodiments from compact, portable, low-cost predictive devices to integrated platforms embedded in OCT consoles, Raman systems, or multiwavelength imaging instruments.

What remains constant across all configurations is the role of time-varying optical behavior. Regardless of whether the data arise from the system's own reflectance sensors or from advanced clinical instruments, the acquisition layer treats these signals as temporal biomarkers that reveal the physiologic readiness of the tissue. These biomarkers fluctuate over short intervals as mitochondria adjust their redox state, outer segments shift alignment, perfusion modulates, or the RPE changes its metabolic output. The diagnostic acquisition component 206 captures these oscillations, enabling the AI-Gating engine 210 to forecast brief windows in which imaging or photomodulation will yield superior signal quality, safety, and therapeutic effect.

Thus, the system does not depend on OCT, OCTA, or any other modality to function. Rather, it operates on a continuum: fully capable of independent physiologic prediction in its simplest form, yet able to incorporate, or retrofit onto, existing ophthalmic equipment to enhance its precision. This dual capacity strengthens the enablement of the AI-Gated photomodulation system 202, broadens its clinical adaptability, and ensures that the physiologic principles underlying AI-Gating are preserved across all embodiments.

TABLE 2

Standalone vs. Integrated Embodiments of the AI-Gating System

| Embodiment Type | Description | Input Sources Utilized | Operational Scope | Clinical/ Engineering Advantages |
|---|---|---|---|---|
| Standalone AI-Gating Unit | Functions as an autonomous predictive device capable of operating without any external imaging system. Uses its own optical sensors to monitor reflectance, scattering, motion, and basic biochemical signatures. | Native reflectance sensors, NIR diodes, basic autofluorescence channels, motion detectors, ambient sensors. | Performs predictive gating, photomodulation timing, physiologic readiness assessment, or baseline imaging capture. | Low-cost, portable, retrofittable; provides predictive value even in resource-limited environments; introduces AI-driven physiologic synchronization without requiring OCT or advanced imaging. |

TABLE 2-continued

Standalone vs. Integrated Embodiments of the AI-Gating System

| Embodiment Type | Description | Input Sources Utilized | Operational Scope | Clinical/ Engineering Advantages |
|---|---|---|---|---|
| Standalone AI-Gating + Photomodulation Unit | Adds integrated photonic emitters for therapeutic light delivery (e.g., red/NIR for photobiomodulation). The AI engine independently determines when tissue is metabolically receptive. | Same as standalone + internal PBM LEDs/lasers. | Physiologic gating for therapeutic illumination; dynamic modulation of pulse timing, duty cycle, or wavelength. | Provides controlled PBM delivered only during mitochondrial readiness; improves safety and therapeutic efficiency; device can be compact or handheld. |
| Integrated with OCT | Receives structural and scattering-based inputs from OCT; uses coherence stability and outer-retinal reflectance as temporal biomarkers. | OCT reflectance profiles, ellipsoid zone stability, outer-retina scattering, motion correction data. | High-precision timing of OCT volume capture; improved delineation of EZ, RPE, and micro-architectural features. | Sharper boundaries, fewer motion artefacts, improved improved reproducibility; enhances existing OCT platforms without changing hardware fundamentals. |
| Integrated with OCTA | Adds microvascular information such as flow regularity, capillary pulsatility, and perfusion stability. | OCTA decorrelation signals, flow void patterns, microvascular pulsatility. | Uses perfusion stability as a predictor for imaging windows or therapeutic timing. | Greater sensitivity for early ischemia or AMD progression; improved interpretation of choriocapillaris behavior. |
| Integrated with FAF | Utilizes autofluorescence intensity, texture, and granularity as metabolic biomarkers. | Lipofuscin and bisretinoid captured via FAF. emission patterns | Detects RPE metabolic transitions; of metabolic quieting for imaging or PBM. predicts intervals | Enhances sensitivity to oxidative stress, Advantages subtle atrophy. RPE instability, |
| Integrated with NIR Reflectance | Measures melanin scattering and photoreceptor variations in NIR spectrum. | integrityreflectance 820-870 nm NIR channels. | Predicts optical clarity and outer-retinal stability; beneficial for early AMD detection. | Deep scanning capability; useful for subtle atrophic or pre-atrophic conditions. |
| Integrated with Raman Spectroscopy | Uses biochemical signatures such as amyloid, oxidized lipids, bisretinoids, and mitochondrial redox states. | Raman spectral peaks for lipids, protein secondary structure, amyloid, A2E/A2F, cytochrome signatures. | Identifies biochemical plateau phases and molecular readiness for capture. | Enables amyloid-guided AMD assessment; optimizes Raman SNR; allows combined structural + biochemical gating. |
| Integrated with Hyperspectral Imaging | Adds wavelength-resolved reflectance and oxygenation gradients. | Hyperspectral reflectance cubes; chromophore maps; O2-related spectral trends. | Detects metabolic plateau states; identifies retinal oxygenation transitions. | Supports AMD monitoring, toxic maculopathy signals, and ischemia mapping. |
| Integrated with SLO/ Fixation Control | Incorporates precise reflectance and eye-tracking signals. | Raster-scanned reflectance profiles; fixation data; microperimetry channels. | Enhances detection of motion quieting and fixation stability. | Improved spatial mapping; useful for microperimetry-gated imaging. |
| Multi-Device Distributed Network | Multiple devices provide synchronized signals to a central AI-Gating engine. | Any combination of OCT, OCTA, FAF, Raman, NIR, hyperspectral, and standalone sensors. | System-wide synchronization of imaging and photomodulation across devices. | Enables research-level multimodal analysis; future-proofs integration paths. |

The AI-Gated photomodulation system 202 is designed with a dual architectural flexibility that significantly enhances its clinical adaptability. At its foundation, the AI-Gated photomodulation system 202 can function as a self-contained predictive engine that does not rely on any external imaging modality. In this standalone form, the AI-Gated photomodulation system 202 uses its own optical and motion-sensing hardware to monitor moment-to-moment changes in reflectance, scattering, fixation stability, and metabolic fluorescence. These native signals, although simpler than those derived from advanced imaging platforms, still contain rich temporal information about tissue coherence and metabolic readiness. This enables the device to perform physiologic forecasting and gated photomodulation independently, making it suitable for portable, low-resource, or entry-level applications where OCT or Raman systems may not be available.

In other embodiments, the AI-Gated photomodulation system 202 integrates directly with widely used ophthalmic instruments such as OCT, OCTA, fundus autofluorescence, hyperspectral imaging, Raman spectroscopy, and near-infrared reflectance cameras. Each of these instruments provides physiologic and structural signals that vary subtly over time, and these variations serve as powerful temporal biomarkers. The AI-Gated photomodulation system 202 analyzes these multimodal signals, either individually or in fused combinations, to refine its predictions about when tissue will be most stable, most metabolically coherent, or most optically receptive.

The modular design allows the AI-Gated photomodulation system 202 to augment existing diagnostic platforms without altering their internal hardware. When paired with OCT, the system can time image acquisition to moments of peak reflectance coherence, improving delineation of the ellipsoid zone or early drusen changes. When paired with Raman or hyperspectral imaging, it identifies biochemical plateau phases that maximize signal-to-noise ratios. With OCTA integration, it identifies brief intervals of perfusion stability that enhance vascular interpretability. Even fixation and motion data from SLO or eye trackers can be used to identify motion quieting intervals ideal for imaging.

This flexibility creates a continuum of embodiments, from a compact device with its own reflectance sensor to an advanced multimodal platform coordinating inputs from several imaging technologies simultaneously. The underlying AI-Gating framework remains constant across all embodiments. What changes is the richness and specificity of the physiologic signals available to the predictive engine.

As a result, the AI-Gated photomodulation system 202 is not confined to any particular instrument, wavelength, or technology. Instead, it provides a generalizable method of physiologic prediction that can be applied to almost any optical system.

3.4 Preprocessing and Feature Extraction Layer

Once optical and physiologic signals are collected by the diagnostic acquisition component 206, they enter the preprocessing and feature extraction stage, where raw data is converted into structured information that the AI uses to interpret tissue physiology. Because each modality generates signals with distinct noise properties, temporal dynamics, and optical behavior, the preprocessing layer is designed to transform these heterogeneous streams into a coherent set of physiologic descriptors.

The first function of this layer is to stabilize and normalize 212 the incoming data. Variability in illumination, frame-to-frame reflectance, or wavelength-dependent brightness can obscure the underlying physiologic patterns that AI-Gating depends on. To address this, the AI-Gated photomodulation system 202 performs intensity normalization across time or wavelength bands, ensuring that subsequent analysis reflects genuine physiology rather than differences in lighting or acquisition conditions.

The AI-Gated photomodulation system 202 then examines each signal for noise and instability 214. Many optical modalities, particularly those influenced by eye motion, tear-film fluctuation, or mitochondrial scattering, benefit from adaptive temporal filtering, which distinguishes true physiologic changes from random noise. These filters operate dynamically, adjusting their behavior in response to signal volatility so that subtle retinal signatures are preserved rather than smoothed away.

Motion estimation 216 is another component of the preprocessing layer. Retinal imaging is uniquely susceptible to micro-saccades, tremor, drift, and blink-induced disruptions. The AI-Gated photomodulation system 202 applies optical-flow-based motion tracking to characterize how the retina moves over time. Rather than simply discarding motion-affected frames, the system uses the motion vectors themselves as temporal biomarkers, recognizing that intervals of motion quieting often coincide with periods of structural and metabolic coherence.

For modalities such as fundus autofluorescence, the preprocessing stage evaluates fine-grained texture patterns 218, measuring local fluctuations in fluorescence intensity and granularity. These variations correlate with oxidative load, bisretinoid accumulation, and RPE metabolic stress, making them powerful inputs into the physiologic model. By quantifying these textures dynamically, the system transforms autofluorescence from a static imaging technique into a real-time indicator of retinal metabolic behavior.

When Raman or hyperspectral data are present, the preprocessing layer performs spectral unmixing and feature isolation 220. This involves separating overlapping biochemical signatures into their constituent molecular components and tracking how these components fluctuate over time. Changes in Raman peaks associated with amyloid, oxidized lipids, or mitochondrial redox states become part of the continuous physiologic timeline that the AI-Gated photomodulation system 202 uses for prediction.

OCT-based signals undergo their own specialized OCT preprocessing 222. For structural OCT, the system extracts the coherence envelope of the returning interferometric field, which reflects layer definition, scattering uniformity, and photoreceptor organization. For OCT angiography, the preprocessing step quantifies flow regularity, decorrelation stability, and microvascular pulsatility. These measures capture the moment-to-moment consistency of perfusion and vascular support.

Across all modalities, the diagnostic acquisition component 206 produces a stream of feature vectors, compact mathematical representations of physiologic state that update continuously and in real time. These vectors serve as the substrate for AI-Gating's predictive engine 210. They encapsulate critical patterns such as reflectance coherence, metabolic quieting, perfusion stability, motion suppression, spectral plateau phases, and biochemical fingerprints. By transforming raw optical data into structured physiologic information, the preprocessing and feature extraction layer enables the AI-Gated photomodulation system 202 to forecast optimal timing intervals for imaging and photomodulation with unprecedented precision.

As the diagnostic acquisition component 206 transforms raw multimodal inputs into structured representations of the tissue's physiologic state, the AI-Gated photomodulation system 202 reaches a natural transition point: the hand-off from data preparation 206 to active physiologic interpretation 208. The continuous feature vectors produced by preprocessing do not merely summarize optical signals; they form a time-ordered physiologic signature that captures subtle fluctuations in structure, metabolism, perfusion, and motion.

These signatures provide the substrate upon which the predictive AI-Gated photomodulation system 202 operates. By assimilating these temporally resolved patterns, the inference layer can recognize trends, detect emerging coherence or instability, and forecast brief intervals in which the tissue is poised to yield the highest diagnostic value or therapeutic responsiveness. This transition, from refined optical features to predictive physiologic insight, marks the conceptual shift from observation to anticipation that defines the core innovation of AI-Gating.

3.5 AI-Gating Predictive Inference Layer

Once the AI-Gated photomodulation system 202 has distilled the raw optical and physiologic signals into structured feature vectors, the physiologic monitoring subsystem 208 assumes the task of interpreting their temporal behavior. This layer functions as the analytical core of AI-Gating, transforming streams of reflectance, fluorescence, scattering, biochemical, vascular, motion, and environmental signatures into forecasts of when the tissue is most likely to enter a state of physiologic stability or metabolic receptivity. Whereas conventional imaging devices react to the state of the tissue at the moment of measurement, the inference engine 224 enables the AI-Gated photomodulation system 202 to anticipate what the tissue will be doing in the near future.

The physiologic monitoring subsystem 208 analyzes short-range temporal fluctuations in the processed signals and identifies patterns that often precede moments of optical or metabolic coherence. This may involve recognizing emerging regularity in reflectance from the photoreceptor layers, detecting stabilization in autofluorescence texture, identifying a plateau in Raman biochemical signatures, or sensing a reduction in microvascular pulsatility on OCT angiography. These changes unfold over timescales measured in milliseconds, and the inference engine 224 continuously tracks these dynamics to determine how they evolve over time.

To perform this type of temporal modeling, the inference engine 224 may incorporate one or more artificial intelligence architectures capable of extracting subtle physiologic trends. Neural networks can learn the multidimensional relationships among optical modalities, while recurrent models, such as LSTM or GRU networks, allow the AI-Gated photomodulation system 202 to interpret sequences of data in context, detecting when a transient fluctuation represents noise or when it signals the onset of a physiologic quieting interval. Probabilistic inference methods, including Bayesian estimation, contribute additional layers of uncertainty quantification, allowing the system to weight its predictions based on the confidence of the underlying physiologic indicators.

The inference engine 224 may also operate as a hybrid model that fuses data from multiple sources, OCT structural coherence, reflectance stability, Raman biochemical peaks, autofluorescence behavior, motion vectors, and environmental parameters, into a single time-aligned predictive horizon. This multimodal fusion 226 produces a dynamic, continuously evolving representation of tissue physiology, enabling the AI-Gated photomodulation system 202 to detect microcycles in mitochondrial redox behavior, fluctuations in scattering uniformity, or short-lived perfusion equilibria.

The output of this layer is a time-indexed estimate of physiologic readiness. Rather than issuing a static classification or threshold, the predictive engine 228 generates a probability curve that updates in real time, reflecting the likelihood that an imminent interval will be optimal for high-value imaging or photomodulation. Because these predictions are refreshed on millisecond to sub-second timescales, the system remains tightly synchronized with the natural rhythms of the tissue.

Through this predictive modeling framework, the inference engine 224 converts optical biomarkers from descriptive indicators into actionable temporal intelligence. It determines not only how the tissue is behaving at the present moment but also when the tissue is most likely to reach a state of coherence that maximizes diagnostic clarity and enhances therapeutic impact. In this sense, the physiologic monitoring subsystem 208 is the conceptual bridge between physiologic observation and physiologic control, the engine that allows AI-Gating to operate proactively rather than reactively, and to deliver light or acquire data at the moments when the tissue is most receptive.

As the physiologic monitoring subsystem 208 continuously refines its understanding of how physiologic signals are evolving over time, the AI-Gated photomodulation system 202 reaches the point at which prediction must be translated into action. The output of the inference engine 224, a dynamic, time-indexed estimate of tissue readiness, forms the basis for the gating logic that governs when the system will deliver light or capture diagnostic information.

In this stage, the probabilistic forecasts generated by the AI are converted into operational decisions: moments of anticipated stability are permitted to trigger photonic output or initiate imaging, while predicted intervals of instability lead to temporary suppression or modulation. This transition from physiologic prediction to controlled actuation is the defining feature of AI-Gating and is what enables the AI-Gated photomodulation system 202 to engage with tissue at precisely the times when diagnostic yield or photomodulation efficacy is highest.

3.6 AI-Processing for AI-Gating

The AI processing layer 230 serves as the decision-making core of the system. While the physiologic monitoring subsystem 208 identifies temporal patterns and forecasts optimal physiologic intervals, the AI processing layer 230 determines how these forecasts will be operationalized. It is here that multimodal optical data, physiologic indicators, and environmental signals are evaluated, weighted, and transformed into gated commands that ultimately regulate photomodulation or diagnostic acquisition. This AI processing layer 230 ensures that AI-Gating functions as a closed-loop, physiologically responsive control system rather than a passive analytic tool.

The AI processing layer 230 receives an uninterrupted stream of feature vectors from the diagnostic acquisition component 206 and physiologic monitoring subsystem 208. Each vector represents the instantaneous physiologic status of the tissue, including reflectance coherence, autofluorescence stability, Raman biochemical plateaus, microvascular regularity, spectral signatures of oxygenation, mitochondrial scattering states, and motion-derived indicators of fixation quieting. These inputs may originate from the system's standalone optical sensors or from integrated modalities such as OCT 104, OCT angiography 106, SLO, fundus imaging systems 108, hyperspectral imagings 110, or Raman spectrometers 102. Environmental parameters, such as illumination, device scatter, or temperature, enter the same processing stream.

Once these inputs are aggregated, the AI processing layer 230 applies a hierarchy of analytic methods to determine whether the predicted physiologic state is sufficiently stable or metabolically receptive to justify opening the photonic gate. The system may utilize weighted neural architectures that assign relative significance to different physiologic predictors; state-space models that track how the retina evolves across time; Bayesian estimators that quantify uncertainty; or hybrid networks that fuse structural, biochemical, and motion-derived features. These algorithms allow the AI processing layer 230 to function as a physiologic adjudicator, deciding whether the current or imminent state of the tissue meets the threshold for high-value imaging or effective photomodulation.

Because the predictive engine 228 updates at millisecond to sub-second intervals, the AI processing layer 230 continually reassesses tissue stability. It computes a readiness score, a scalar or vector quantity that represents the likelihood that upcoming intervals will produce optimal light-tissue interaction. This readiness score is then compared against adjustable control thresholds that may be defined by clinical parameters, safety requirements, or manufacturer-specified performance metrics. If the readiness score exceeds the threshold, the AI-Gated photomodulation system 202 issues a gating command that initiates illumination, spectroscopy, or image capture. If not, the system delays emission or acquisition until physiologic conditions improve.

Importantly, the AI processing layer 230 incorporates feedback. After each gated emission or acquisition event, the system re-evaluates the tissue's response, feeding these data back into the predictive model. This creates an adaptive loop in which the system continually learns from the physiologic consequences of its own output. Over time, this feedback improves predictive accuracy, reduces false-positive gating events, and tailors the system's performance to the specific retinal characteristics of individual patients.

Through this process, the AI processing layer 230 establishes the functionality that differentiates AI-Gating from static image acquisition: the AI-Gated photomodulation system 202 no longer observes tissue passively but interacts with it responsively, intelligently, and at precisely the moments when physiologic conditions are most favorable. It is this transformation, from prediction to actionable control, that elevates AI-Gating into a novel class of medical optics that bridges real-time physiology and photonic engineering.

TABLE 3

AI Processing Elements and Their Role in Predictive Gating

| AI Processing Component | Type of Input Processed | Technical Function | Contribution to AI-Gating Control Logic |
|---|---|---|---|
| Multimodal Feature Aggregator | Reflectance, OCT, OCTA, FAF, Raman, hyperspectral, motion | Combines disparate optical and physiologic streams into a unified feature space | Provides integrated physiologic context for prediction and gating |
| Weighted Neural Networks | Processed feature vectors from all modalities | Assigns modality-dependent weights to physiologic indicators | Emphasizes high-value biomarkers while suppressing noise-affected channels |
| Recurrent Temporal Models (LSTM/GRU) | Time-ordered sequences of optical/biochemical features | Detects short-interval oscillations in coherence, scattering, flow, and fluorescence | Identifies micro-cycles that precede optimal imaging or therapy windows |
| Bayesian State Estimators | Prediction outputs and uncertainty metrics | Computes probabilistic readiness estimates and confidence intervals | Prevents gating during physiologic instability; ensures safety and robustness |
| Spectral and Biochemical Classifiers | Raman and hyperspectral signatures | Detects biochemical plateau phases, redox oscillations, and amyloid signatures | Triggers Raman-based or hyperspectral-based decision pathways |
| Motion-Stability Analyzer | Microsaccades, drift, blink cycles | Evaluates fixation quieting intervals | Prevents gating during motion artifacts; increases spatial resolution |
| Perfusion and Vascular Regularity Model | OCTA flow signals, decorrelation stability | Detects microvascular steadiness | Ensures imaging and photomodulation occur during stable perfusion phases |
| Environmental Condition Monitor | Ambient illumination, scatter, temperature | Assesses external noise-risk conditions | Avoids gating during environmental instability |
| Readiness Score Generator | Output from all models | Synthesizes physiologic predictions into a single decision metric | Converts physiologic insight into threshold-based gating decisions |
| Closed-Loop Feedback Engine | Post-emission optical and physiologic responses | Re-trains or updates inference weights in real time | Improves accuracy and personalization over repeated use |

As the AI processing layer 230 synthesizes multimodal inputs into a continuously updated readiness score, the AI-Gated photomodulation system 202 arrives at the stage where predictive analysis must be translated into photonic control 232. The readiness score, together with its associated confidence values, serves as the operational bridge between physiologic prediction and system action. At this point the device no longer functions as a passive observer but as an adaptive agent capable of responding to moment-to-moment changes in tissue physiology.

When the predicted interval meets or exceeds the defined thresholds, the AI-Gated photomodulation system 202 issues a gating command that instructs the photomodulation module or imaging subsystem 204 to proceed. Conversely, when physiologic instability is detected, the system automatically delays or suppresses output. This transition from insight to actuation enables AI-Gating to function as a closed-loop physiologic controller, synchronizing the delivery of light or acquisition of diagnostic data with the tissue's most favorable states.

3.7 AI-Gating Gating Logic Layer

After generating a readiness score and its associated confidence values, the AI-Gated photomodulation system 202 enters the gating logic 234*e*, where physiologic prediction is translated into operational control. This is the stage in which the AI-Gated photomodulation system 202 determines whether the device should deliver photonic energy, initiate image capture, adjust its output parameters, or temporarily withhold activity until a more favorable physiologic state arises. The gating logic 234 evaluates the predictions from the physiologic monitoring subsystem 208 and applies them to a flexible decision framework that adapts in real time to changing tissue conditions.

In its simplest form, the gating logic 234 may operate as a binary gate, authorizing or blocking illumination or acquisition depending on whether the readiness score surpasses a predetermined threshold. In more sophisticated embodiments, the system modulates the intensity, duration, or wavelength of photonic output based on the predicted level of metabolic receptivity. When the AI-Gated photomodulation system 202 anticipates particularly stable intervals, those characterized by mitochondrial quieting, scattering coherence, or perfusion steadiness, the AI-Gated photomodulation system 202 may initiate a burst of pulses or a rapid sequence of imaging frames to maximize diagnostic yield. Conversely, if the AI-Gated photomodulation system 202 predicts transient instability or metabolic vulnerability, the gating logic 234 may withhold output entirely or reduce its amplitude to prevent unnecessary exposure.

The AI-Gated photomodulation system 202 can also prioritize among multiple imaging modalities. When Raman plateau phases are detected, the device may preferentially activate its Raman channel; during periods of structural quieting, OCT capture may take precedence; and when autofluorescence stabilizes, the system may trigger FAF acquisition. These modality-selection decisions are based on the predicted physiologic value of each modality in the upcoming interval.

Safety considerations are woven into the AI-Gating engine 210 as well. The AI-Gated photomodulation system 202 is designed to suppress photomodulation when the tissue appears vulnerable, whether because of transient metabolic stress, excessive scattering, irregular perfusion, or unstable fixation. By continuously tracking these signals, the AI-Gated photomodulation system 202 ensures that therapeutic pulses are delivered only when biologic response is likely to be favorable.

Clinician-defined thresholds and adaptive operating criteria may also be incorporated, allowing users to customize the aggressiveness or conservativeness of gating behavior. Over repeated use, feedback from prior illumination or imaging events can recalibrate these thresholds through machine-learning updates, allowing the system to tailor its performance to the individual physiologic characteristics of each patient.

Through these mechanisms, the gating logic 234 layer acts as the operational center of the system, converting physiologic prediction into real-time control decisions that optimize both imaging and therapeutic efficacy.

3.8 AI-Gating Output and Actuation Layer

The actuation layer 236 and the photonic control 232 are the final stage of the AI-Gating architecture, where predictive physiologic insight is converted into precise optical or diagnostic action. Once the gating logic 234 determines that an upcoming interval represents a period of structural coherence or metabolic receptivity, the actuation layer 236 and the photonic control 232 execute the appropriate command with millisecond-level timing. This actuation layer 236 and the photonic control 232 serve as the physical interface between the AI-Gating engine 210 and the hardware responsible for imaging, spectroscopy, or photomodulation.

In imaging embodiments, the actuation layer 236 may initiate the capture of OCT volumes, reflectance frames, or autofluorescence sequences during predicted windows of optical stability. By limiting acquisition to the brief intervals when fixation is quiet and scattering noise is minimized, the AI-Gated photomodulation system 202 produces sharper boundaries, improved repeatability, and higher diagnostic yield. In biochemical embodiments, such as Raman spectroscopy, the actuation layer 236 triggers spectral acquisition precisely when the predictive engine 228 identifies biochemical plateau phases, moments in which Raman peaks for lipids, bisretinoids, or amyloid become most stable and least contaminated by physiologic noise.

In therapeutic configurations, the actuation layer 236 controls the delivery of photomodulation pulses. Because the efficacy of red and near-infrared photobiomodulation depends strongly on the instantaneous mitochondrial redox state, membrane potential, and intracellular oxygen availability, the actuation layer 236 ensures that illumination is delivered only during predicted intervals of metabolic readiness. The AI-Gated photomodulation system 202 may adjust pulse timing, duration, or wavelength in direct response to physiologic forecasts, ensuring that therapy is not only delivered safely but also at the moments when the tissue is most responsive.

In multimodal configurations, the actuation layer 236 can coordinate several devices simultaneously. For example, it may trigger OCT imaging during intervals of structural stability while instructing a Raman spectrometer to capture biochemical information during the same predicted window. This level of temporal synchronization has not been achievable with conventional open-loop systems and represents a major advantage of the AI-Gating architecture.

The actuation layer 236 may also refine future predictions by recording the exact timestamps at which each emission or acquisition event occurs. By comparing these events with subsequent physiologic responses, the actuation layer 236 can improve its predictive accuracy over time through adaptive learning. This feedback creates an intelligent closed-loop behavior in which the device becomes increasingly personalized to the tissue characteristics of the individual patient.

Taken together, this layer transforms AI-Gating from a predictive analytic tool into a physiologically responsive optical system capable of delivering imaging or therapy with high precision.

Figure 3:
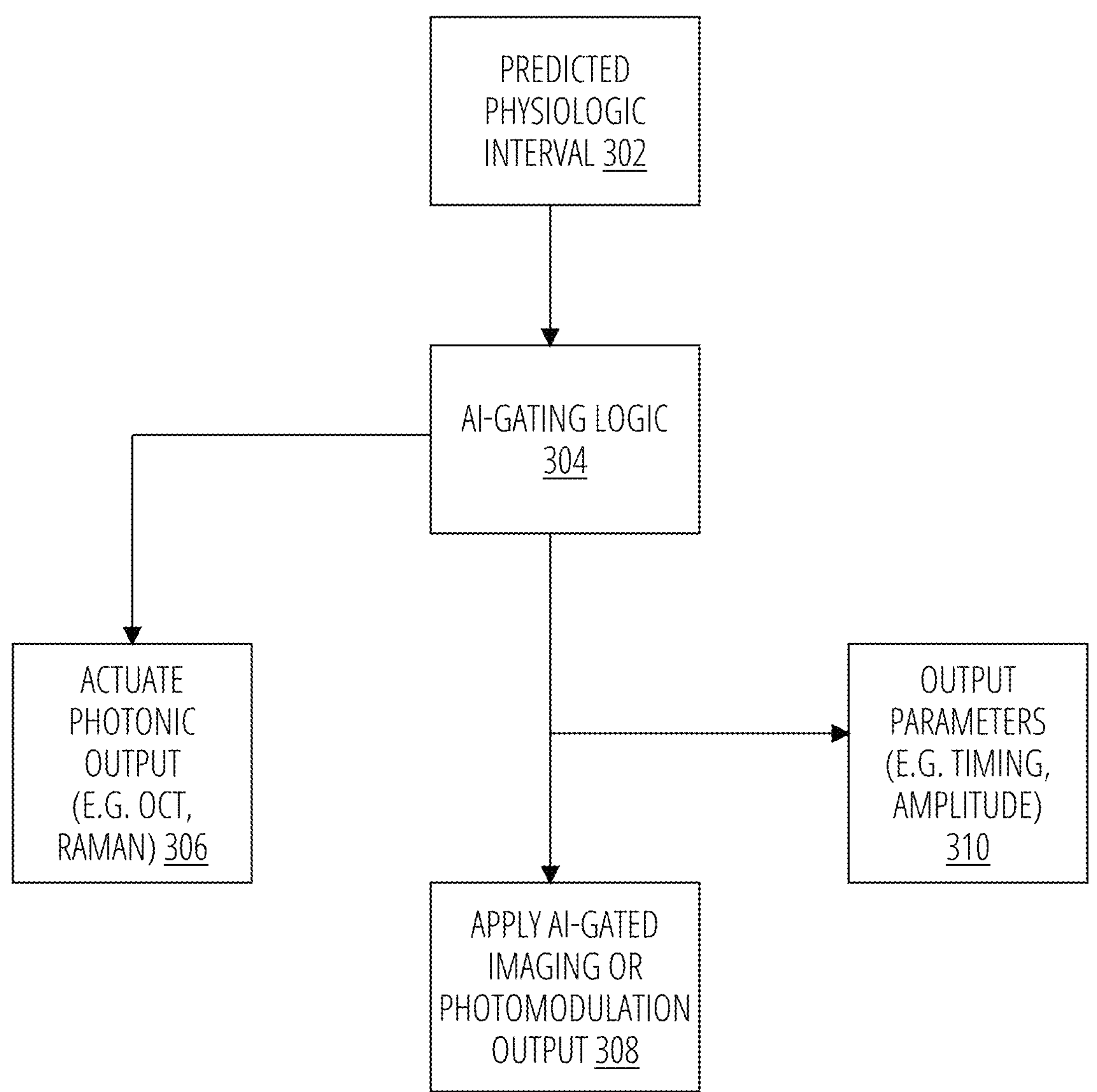
FIG. 3 illustrates a flowchart of AI-Gating output.

FIG. 3 shows the final stage of the actuation layer 236 and the photonic control 232 pathway. The AI-Gated photomodulation system 202 executes the gated action determined by the AI-Gating engine 210. When a predicted high-value interval arrives, the device applies the appropriate photonic output, such as an OCT frame acquisition, an OCTA volume, a reflectance capture, a Raman spectrum, or a photomodulation pulse, precisely during that optimal physiologic window. This ensures that imaging occurs when optical coherence, perfusion stability, and biochemical quieting are maximized, and that therapeutic light is delivered only when mitochondria are most receptive. Whether the output is diagnostic or therapeutic, it is applied with millisecond-level temporal precision governed entirely by the physiologic predictions generated by AI-Gating.

When the predicted physiologic interval 302 is determined by the physiologic monitoring subsystem 208, the AI-Gating logic 304 may actuate photonic output 306, apply AI-Gated imaging or photomodulation output 308, and/or output parameters 310.

4.0 AI-Gated Closed-Loop Feedback Integration

A defining characteristic of the AI-Gating architecture is its closed-loop behavior, in which every actuation event becomes new information that refines subsequent predictions. Rather than functioning as a one-directional pipeline, the AI-Gated photomodulation system 202 continuously cycles between measurement, interpretation, action, and physiologic response. Each imaging frame or photonic pulse alters the optical or metabolic state of the tissue, and these changes, in turn, influence the upstream data acquired by the system.

For example, a Raman spectral acquisition performed during a period of unexpected biochemical variability may produce a lower-than-expected signal-to-noise ratio. This deviation is immediately incorporated into the predictive model, prompting the AI-Gated photomodulation system 202 to adjust its estimate of when the next biochemical stability window will occur. Likewise, the delivery of a photomodulation pulse, particularly in the red or near-infrared spectrum, may induce transient changes in mitochondrial scattering, autofluorescence texture, or reflectance amplitude. These post-illumination signatures are captured by the diagnostic acquisition component 206 and used to update the model's understanding of the tissue's recovery dynamics.

Even seemingly minor physiologic changes, such as the onset of a blink, a shift in fixation, or a temporary increase in tear-film irregularity, contribute to the evolving temporal landscape. Motion vectors, coherence fluctuations, and alterations in reflectance geometry are continuously interpreted as indicators of the tissue's short-term trajectory. The predictive engine 228 adapts in real time, updating its estimation of when optical stability or metabolic quieting will recur.

Through this continuous cycle of action and measurement, the AI-Gated photomodulation system 202 becomes increasingly aligned with the rhythms of the retina itself. The closed-loop architecture enables the device to self-correct, learning from both successful and suboptimal intervals, and progressively improving the accuracy of its temporal forecasts. This dynamic feedback loop is important to the AI-Gated photomodulation system 202, allowing the AI-Gated photomodulation system 202 to behave as a physiologically responsive platform rather than a static imaging or illumination tool.

4.1 Deployment Configurations

The AI-Gating architecture is intentionally designed for broad deployment across diverse clinical, research, and mobile environments. Its modular construction allows the AI-Gated photomodulation system 202 to function either as a self-contained predictive engine or as a deeply integrated component within established ophthalmic imaging platforms. This flexibility enables the AI-Gated photomodulation system 202 to adapt to a wide spectrum of clinical workflows, from high-complexity diagnostic suites to portable field devices, without altering its core predictive capabilities.

4.2 Integrated Clinical Platforms

In one embodiment, AI-Gating is embedded directly within multimodal imaging systems such as OCT, OCTA, Raman spectroscopy, hyperspectral cameras, or fundus reflectance instruments. In this configuration, the predictive engine 228 receives real-time physiologic signals natively from the host device and governs its timing, illumination structure, and acquisition sequencing. Integration at this level enhances the performance of existing devices by converting them from passive imagers into physiologically responsive, closed-loop diagnostic systems. The host device benefits immediately from reduced motion artifacts, higher-fidelity structural capture, optimized Raman or hyperspectral acquisition, and improved reliability during follow-up examinations 4.3 Standalone Predictive Engines In another embodiment, the AI-Gated photomodulation system 202 operates as a standalone predictive processor that interfaces with commercially available imaging hardware through software, APIs, or network connections. This model preserves the full benefit of AI-Gating without requiring modification of the host device's hardware. The standalone engine receives reflectance, autofocus, Raman, OCT, or motion data and issues gating commands back to the device, enabling upgraded temporal control even in legacy systems. This embodiment is especially advantageous for clinics that cannot replace equipment but wish to incorporate physiologic timing control.

4.4 Portable and Handheld Systems

Portable, handheld, or point-of-care devices may incorporate a compact form of AI-Gating for settings where environmental and physiologic variability is high. These include remote screening locations, telemedicine deployments, and home-monitoring units. In these environments, AI-Gating provides stability against motion, lighting variability, tear-film changes, and fixation drift, conditions that traditionally undermine portable imaging. By triggering acquisition only during physiologically coherent intervals, the system substantially improves diagnostic reliability outside controlled clinical environments.

4.5 Cloud-Connected and Distributed Architectures

The system further supports a distributed cloud-connected model in which predictive inference occurs remotely. Here, the device streams acquisition data to a secure cloud host, where AI-Gating analyzes temporal biomarkers and returns optimal gating windows. This architecture allows computationally intensive inference, such as deep multimodal fusion or large Bayesian ensembles, to be performed centrally, while lightweight devices execute actuation locally. This model enables population-level screening, continuous longitudinal monitoring, and remote biomarker tracking at scale.

4.6 Multi-Device Synchronization Networks

In certain embodiments, AI-Gating coordinates multiple devices simultaneously, allowing synchronized interrogation from different modalities. For example, OCT and Raman spectroscopy may be triggered within the same physiologic window, or FAF may be acquired immediately following a predicted metabolic plateau. This multi-device coordination creates a coherent multimodal snapshot of retinal physiology that cannot be achieved with asynchronous acquisition. AI-Gating ensures that all devices operate in harmony with the underlying biology of the tissue rather than in isolation from it.

4.7 General Applicability Beyond Ophthalmology

Although optimized for retinal use, the same deployment principles translate to any setting where optical, spectroscopic, or photomodulatory interaction depends on the physiologic state of living tissue. Dermatology, neurology, oncology, and regenerative medicine all benefit from physiologically timed illumination and measurement. Thus, the deployment architecture is intentionally domain-agnostic and extensible across medical and biologic platforms.

4.8 Detailed Description of AI-Gating Predictive Embodiment

The AI-Gated photomodulation system 202 provides an adaptive, physiologically synchronized optical architecture in which imaging and photomodulation are timed according to the predicted physiologic readiness of the tissue. Rather than acquiring frames or delivering light at fixed intervals, the system continuously evaluates the evolving optical, structural, vascular, biochemical, and metabolic state of the tissue. Using these temporal inputs, the AI-Gating engine 210 predicts when the tissue will transition into a short-lived interval of optical coherence, physiologic stability, or heightened metabolic receptivity. Imaging or therapeutic modules are then triggered during these predicted high-value intervals, converting conventional open-loop optical systems into biologically synchronized closed-loop platforms.

4.9 Predictive Physiologic Timing

Biologic tissues do not remain static between imaging events. In the retina, physiologic activity unfolds over milliseconds to seconds, driven by processes such as mitochondrial redox oscillations, tear-film breakup and reformation, microsaccadic drift and stabilization, choriocapillaris micro-pulsatility, transient oxidative fluctuations in autofluorescence, Raman spectral stabilization phases, and momentary increases in reflectance coherence related to outer-segment alignment. Although these fluctuations appear random in real time, high-frequency optical sampling reveals that they follow reproducible temporal trajectories that rise, decelerate, converge, and enter short-lived plateau phases.

These temporal transitions directly influence every optical modality. During brief intervals, retinal reflectance becomes more coherent, mitochondrial metabolic noise decreases, Raman biochemical signatures stabilize, perfusion irregularity diminishes, and autofluorescence patterns show reduced variability. Conversely, optical signals become less reliable and more susceptible to noise when instability arises from fixation jitter, oxidative microevents, or perfusion turbulence.

Conventional imaging systems ignore these physiologic cycles and acquire frames at fixed time points, regardless of whether the underlying tissue is optically or metabolically suitable for capture. As a result, image quality varies unpredictably from session to session, subtle biomarkers may be obscured, and therapeutic light delivery may occur during periods of reduced mitochondrial receptivity.

The AI-Gated photomodulation system 202 resolves this limitation by forecasting when the tissue will next enter a transient interval of physiologic coherence. Instead of responding only to instantaneous measurements, the AI-Gating engine 210 continuously interprets evolving temporal behavior across reflectance, autofluorescence, Raman spectral stability, perfusion harmonics, and motion signatures. By recognizing the statistical patterns that precede stability, the AI-Gated photomodulation system 202 predicts when optical clarity, metabolic quieting, vascular regularity, and motion stillness are most likely to align.

During these predicted windows, the AI-Gated photomodulation system 202 permits imaging or photonic emission; outside of them, activity is delayed or suppressed. This adaptive timing transforms optical acquisition from a technician-scheduled event into a biologically synchronized process that occurs only when the retina is most capable of providing meaningful diagnostic information or responding to therapeutic illumination.

Importantly, this predictive capability supports, not merely single-modality improvements, but the coordinated timing of multiple optical modalities within the same physiologic gate. By aligning structural, biochemical, vascular, and reflectance-based measurements to a shared biologic interval, the AI-Gated photomodulation system 202 enables multimodal predictive fusion in which OCT, OCTA, Raman spectroscopy, autofluorescence, and photomodulation may be synchronized rather than operating independently.

In this manner, AI-Gating shifts optical systems from static, open-loop timing to an adaptive, closed-loop framework anchored to the intrinsic temporal behavior of the tissue itself.

5.0 Multimodal Input Acquisition and AI-Gating Prediction

The AI-Gated photomodulation system 202 functions as a multimodal optical intake engine that continuously receives streams of structural, biochemical, perfusion-based, reflectance, scattering, and fluorescence-derived data from any combination of available modalities, including optical coherence tomography, OCT angiography, visible and near-infrared fundus reflectance, fundus autofluorescence, scanning laser ophthalmoscopy, Raman spectroscopy, hyperspectral imaging, and interferometric or scattering-based sensors.

The disclosed architecture recognizes that every modality contributes two distinct forms of information. The first is the familiar diagnostic output, such as OCT layer boundaries, Raman biochemical fingerprints, or perfusion maps, that reflects the structural and biochemical state of the tissue. The second, and more powerful, is the continuous stream of temporally evolving biomarkers embedded within these signals that reveal how the physiologic state of the tissue is changing from moment to moment.

As each optical frame is acquired, the AI-Gated photomodulation system 202 interprets not only the diagnostic content but also the dynamic fluctuations that ride on top of the signal. OCT frames may show changes in outer-retinal reflectivity and ellipsoid-zone coherence that signal brief periods of structural stability. Raman spectra may enter transient biochemical plateau phases in which lipid, amyloid, or bisretinoid signatures become clearer as metabolic noise decreases. OCT angiography may display short-lived intervals in which decorrelation harmonics converge, allowing high-fidelity visualization of capillary perfusion. Fundus autofluorescence may reveal brief reductions in oxidative variability, and even small changes in reflectance uniformity may indicate that scattering pathways have temporarily stabilized. These fluctuations, although subtle, encode whether the tissue is stable, unstable, or transitioning through a physiologic micro-cycle.

Over time, the AI-Gated photomodulation system 202 accumulates these temporal signatures across modalities, creating a continuously updated physiologic timeline rather than a collection of isolated snapshots. The result is a composite portrait of retinal behavior that reflects not only what the tissue looks like, but how frequently it stabilizes, how long those windows last, whether metabolic noise is rising or falling, and when motion or perfusion will likely allow a high-quality capture. Because these fluctuations occur with recognizable patterns, they provide the raw material for prediction.

It is this fusion of static diagnostic content with dynamic temporal biomarkers that enables AI-Gating to operate. Rather than treating incoming data as independent images, the AI-Gated photomodulation system 202 interprets the evolving physiologic rhythms encoded across modalities and determines whether the tissue is approaching or departing from a state of structural, metabolic, or vascular coherence. When boundary sharpness increases, Raman variance decreases, autofluorescence smooths, or OCTA micro-pulsatility becomes harmonic, the AI-Gated photomodulation system 202 recognizes that the retina is trending toward a high-value state. Conversely, rising scatter noise, spectral instability, or perfusion turbulence indicates that the tissue is entering a period of physiologic disorder.

Because these transitions occur predictably, even at rapid time scales, the AI-Gated photomodulation system 202 can forecast when the retina will next be optically quiet, metabolically receptive, motion-stable, or perfusion-regular. The multimodal inputs, therefore, serve not only as diagnostic datasets but as predictive substrates. AI-Gating transforms these dynamic signals into a temporal forecast and synchronizes imaging or therapeutic exposure to the predicted interval in which the tissue is most likely to yield meaningful information or respond beneficially to light.

This architecture supports both single-modality operation and true multimodal predictive fusion. While the AI-Gating engine 210 may function with only one optical source, predictive robustness increases substantially as additional modalities contribute complementary physiologic signals. In its integrated embodiment, the AI-Gated photomodulation system 202 may synchronize two or more modalities to act within the same predicted physiologic window, such as OCT and Raman, OCTA and autofluorescence, or structural imaging combined with photomodulation.

The AI-Gated photomodulation system 202 introduces a coordinated timing capability. The multimodal embodiment of the AI-Gated photomodulation system 202 establishes a temporal architecture in which structural, vascular, metabolic, and biochemical modalities are triggered only within the same predicted window of physiologic stability. This creates a form of cross-modal temporal coherence.

Each modality therefore captures data under identical physiologic conditions rather than at unrelated or artifact-prone moments in time. By aligning multiple imaging and therapeutic channels through predictive physiologic gating, the AI-Gated photomodulation system 202 generates multimodal datasets that are more reproducible, more interpretable, and diagnostically more powerful than any single modality operating alone.

5.1 Feature Extraction and Temporal Biomarker Reconstruction

Once multimodal optical data enter the AI-Gated photomodulation system 202, each incoming signal is transformed from a raw measurement into a physiologic descriptor that can be interpreted over time. This process begins with preprocessing steps 206 that normalize 212 intensity, suppress noise 214, align sequential frames, and correct for spectral or spatial distortion. The AI-Gated photomodulation system 202 then extracts features 220 that characterize the tissue's optical, biochemical, structural, vascular, and motion-related properties. These descriptors may include reflectance coherence, autofluorescence uniformity, Raman spectral variance, OCT boundary sharpness, OCTA flow harmonic regularity, tear-film oscillation signatures, and motion vector deceleration.

A distinction of the disclosed AI-Gated photomodulation system 202 is that none of these descriptors are treated as static or isolated values. Each feature is reconstructed as a time-indexed trajectory that reflects how the tissue's physiologic state evolves across milliseconds to minutes. This temporal re-expression is important because virtually every biologic process relevant to imaging or photomodulation is dynamic rather than fixed. Mitochondrial behavior alternates between higher-noise and lower-noise metabolic states; autofluorescence fluctuates with oxidative micro-events; perfusion signatures vary with micro-pulsatility; and Raman spectral purity stabilizes only intermittently when metabolic noise decreases.

Through this temporal reconstruction, the AI-Gated photomodulation system 202 can identify physiologic states that would be invisible in a single snapshot. For example, mitochondrial quieting is not detected by observing a single Raman frame but by recognizing a downward trend in spectral variance that converges onto a short-lived biochemical plateau. OCT motion quiescence is detected not by waiting for a still frame but by observing the progressive deceleration of fixation drift that reliably precedes micro-stillness. Similarly, choriocapillaris stability emerges as rhythmic convergence of OCTA decorrelation values during predictable pulsatility intervals.

These evolving trajectories form the physiologic substrate upon which predictive modeling operates. The AI-Gating engine 210 analyzes their slopes, oscillations, inflection points, and convergence patterns to determine whether the tissue is moving toward coherence or instability. A biomarker trending toward stability signals that a high-value interval for imaging or photomodulation is approaching, while divergence or rising variability indicates that activity should be delayed or suppressed. The diagnostic meaning of each signal, therefore, derives not from its instantaneous magnitude but from its temporal directionality and physiologic context.

This continuous reconstruction of temporal biomarkers enables AI-Gating to convert multimodal optical inputs into interpretive physiologic timelines. It is this temporal transformation, not merely feature extraction, that allows the AI-Gated photomodulation system 202 to anticipate when the tissue will be most structurally stable, metabolically quiet, optically coherent, or vascularly regular.

Importantly, the disclosed architecture supports both single-modality operation and multimodal predictive fusion. When multiple modalities contribute temporal information, such as simultaneous stabilization in OCT reflectance, Raman variance, and OCTA perfusion harmonics, the AI-Gated photomodulation system 202 can forecast physiologic readiness with substantially greater precision.

As these temporal trajectories are reconstructed, it becomes possible to characterize not only the physiologic state of the tissue at a given moment but also how that state will evolve over the immediate future. Because each biomarker follows a recognizable trajectory of increase, convergence, stabilization, or decline, its temporal behavior can be directly correlated with predictable changes in optical signal quality. These relationships form the foundation upon which predictive control is built. The following table summarizes representative temporal dynamics and their observable optical manifestations, illustrating how the AI-Gated photomodulation system 202 converts evolving physiologic behavior into actionable inputs for AI-Gating.

TABLE 4

Reflectance-Derived Physiologic Determinants Relevant to AI-Predictive Gating

| Physiologic Determinant | Optical/Reflectance Signature | Associated Modality | Clinical or Biochemical Meaning | Predictive Value for AI-Gating |
|---|---|---|---|---|
| Photoreceptor Outer Segment Integrity | Reflectance band uniformity; ellipsoid zone definition | OCT, NIR | Mitochondrial density, photoreceptor metabolic health | Stable reflectance indicates mitochondrial quieting and optimal imaging window |
| Mitochondrial Redox State | NIR reflectance steadiness; Raman redox peaks | NIR, Raman | Oxidative phosphorylation balance, photoreceptor resilience | Quieted redox oscillation predicts ideal Raman acquisition moments |
| RPE Lipofuscin Load | FAF brightness, granularity, texture transitions | FAF | Oxidative stress, bisretinoid accumulation | FAF smoothness phase predicts reduced metabolic noise |
| Melanin Distribution | Deep NIR absorption; scattering amplitude | NIR, Multispectral | Choroidal integrity, RPE robustness | Consistent NIR absorption indicates structural stability |
| Interphotoreceptor Matrix Fluid Content | OCT hyper-/hypo-reflectivity; internal shadowing changes | OCT | Subclinical edema, photoreceptor layer hydration | Stable scattering suggests reduced motion and improved signal quality |
| Drusen Composition (Lipids/Amyloid) | Raman peaks (lipids 1440-1460 $cm^{-1}$; amyloid ~1660 $cm^{-1}$) | Raman, Reflectance | Drusen maturation stage, amyloid load, AMD progression | Plateaued Raman variance indicates stable biochemical acquisition window |
| RPE Morphologic Stability | FAF texture; OCT RPE band thickness | FAF, OCT | RPE metabolic stress, early degeneration | Predicts metabolic quieting useful for synchronized imaging |
| Choriocapillaris Perfusion Regularity | OCTA flow void consistency; decorrelation signal stability | OCTA | Microvascular health, ischemia risk | Perfusion regularity predicts ideal OCTA timing |
| Fixation Stability & Micromovements | Reflectance jitter, SLO tracking, motion vectors | Reflectance, SLO | Patient fixation quality, microsaccade dynamics | Predicts motion-minima windows for high-resolution capture |
| Spectral Oxygenation Gradients | Hyperspectral absorption patterns | Hyperspectral | Local retinal oxygenation, metabolic stress | Stability in $O_2$-related signatures signals a high SNR capture period |

Table 4 summarizes the major physiologic variables of retinal and subretinal tissue that manifest as changes in reflectance, absorption, scattering, autofluorescence, and spectral emission. Reflectance is foundational to retinal diagnostics because nearly every major imaging modality, including OCT, OCTA, FAF, NIR, hyperspectral analysis, and Raman spectroscopy, derives its signals from how tissue interacts with light. These optical signatures encode mitochondrial function, photoreceptor alignment, RPE metabolic stress, drusen biochemistry, vascular perfusion, and fixation stability. The AI-Gated photomodulation system 202 interprets these reflectance-derived biomarkers as temporal biomarkers, time-dependent physiologic indicators that allow the system to forecast short intervals of optical and metabolic stability. By synchronizing imaging or photomodulation to these predicted windows, AI-Gating improves signal-to-noise ratio, enhances reproducibility, and increases diagnostic and therapeutic precision.

Figure 4:
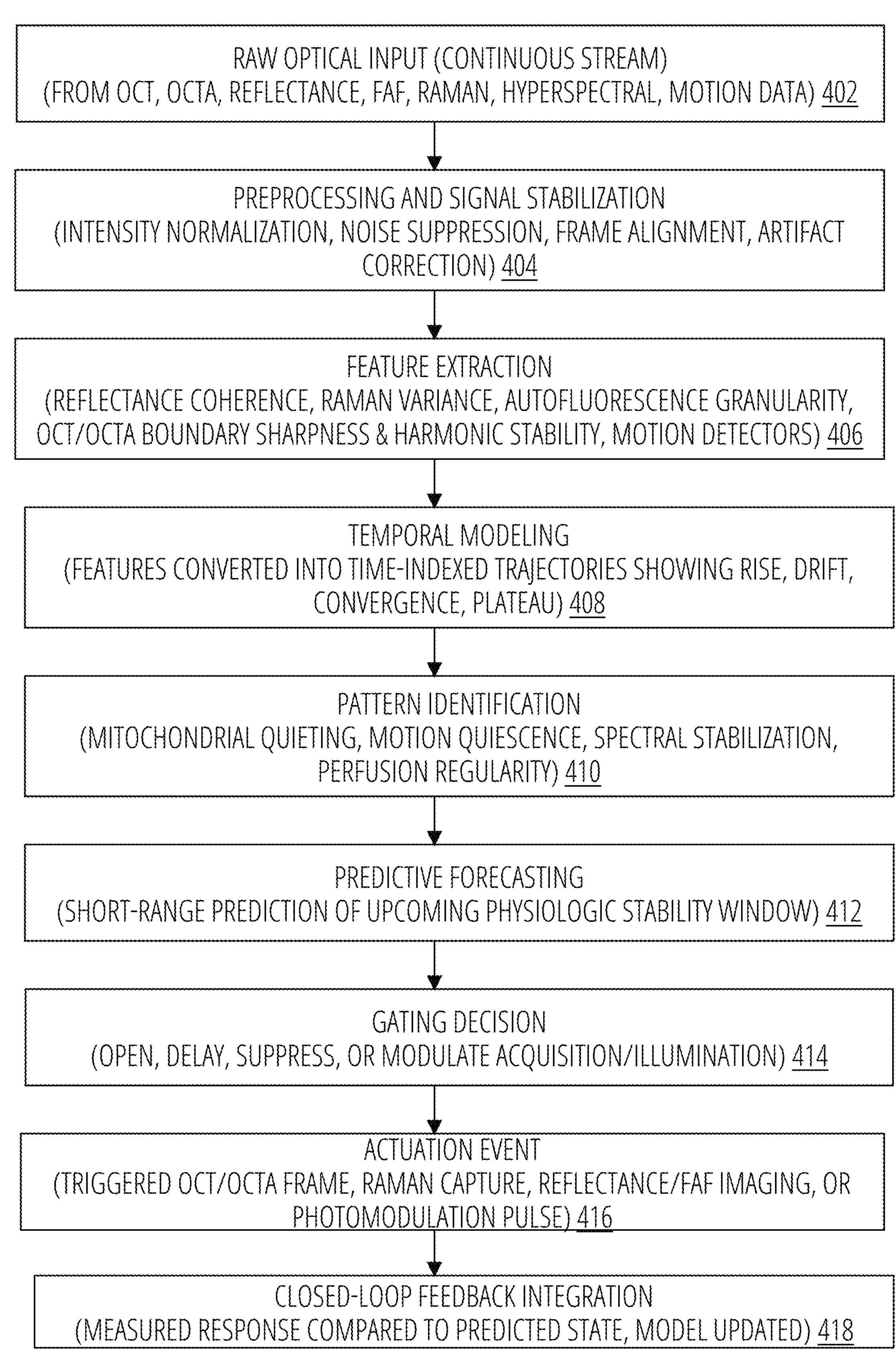
FIG. 4 is a diagram that illustrates the transformation of continuous multimodal optical input into time-indexed biomarker trajectories.

FIG. 4 is a diagram illustrates the transformation of continuous multimodal optical input into time-indexed biomarker trajectories, which are analyzed to forecast physiologic stability and guide AI-Gated imaging or therapeutic actuation within a closed-loop system.

The process starts with raw optical input (continuous stream) 402 from OCT, OCTA, reflectance, FAF, Raman, hyperspectral, and/or motion data. This input is then processed by the preprocessing and signal stabilization 404, which performs intensity normalization, noise suppression, frame alignment, and artifact correction, with the various functions of the diagnostic acquisition component 206. The process then performs feature extraction 406 using reflectance coherence, Raman variance, autofluorescence granularity, OCT/OCTA boundary sharpness & harmonic stability, motion detectors, with the feature isolation 220 module in some embodiments.

The features may then be converted into time-indexed trajectories showing rise, drift, convergence, plateau in the temporal modeling 408 step. The pattern identification 410 step may then perform mitochondrial quieting, motion quiescence, spectral stabilization, perfusion regularity, perhaps using the evaluate texture patterns 218 module. The predictive forecasting 412 step may then make a short-range prediction of the upcoming physiologic stability window, using the predictive engine 228.

With that prediction, a gating decision 414 may decide to open, delay, suppress, or modulate acquisition/illumination, using the AI-Gating engine 210. The actuation layer 236 and the photonic control 232 may also perform the actuation event 416 step, triggering the OCT/OCTA frame, instituting Raman capture, initiating the reflectance/FAF image, or issuing a photomodulation pulse. The closed-loop feedback integration 418 step may perform a measured response compared to the predicted state, and the model may be updated.

5.2 Retinal Physiology as Determined by Reflectance

Reflectance-based imaging is one of the core scientific foundations of retinal diagnostics. Modalities such as optical coherence tomography (OCT), fundus photography, fundus autofluorescence (FAF), near-infrared reflectance imaging, and hyperspectral analysis all operate on the principle that retinal tissue encodes its structural, biochemical, and metabolic state in the way it scatters, absorbs, or emits light. These optical signatures are not passive artifacts; they arise from specific physiologic determinants, including cellular architecture, membrane integrity, mitochondrial activity, lipofuscin and bisretinoid load, melanin distribution, extracellular lipid content, interstitial fluid, and microvascular perfusion.

The AI-Gated photomodulation system 202 organizes these multimodal optical signals into a coordinated hardware-software architecture capable of identifying, predicting, and acting upon transient physiologic intervals in which the retina (or other target tissue) is most receptive to high-value imaging, spectroscopy, or photomodulation. Reflectance thus becomes not only a diagnostic readout but also an upstream biomarker that informs the system's predictive timing.

The architecture is modular and deployable in multiple configurations: as a standalone AI predictive-gating engine, as an integrated subsystem within existing clinical imaging platforms, or as a distributed multi-device ecosystem sharing physiologic timing signals.

At the system's core is an intelligent temporal-control framework. Multimodal optical inputs, together with physiologic parameters (such as fixation stability or perfusion regularity) and device-state metadata, are continuously acquired and analyzed to extract temporal biomarkers. These biomarkers enable the system's predictive inference engine 224 to forecast short-term intervals of physiologic stability or metabolic quieting.

The gating logic 234 then regulates the timing, amplitude, modality, and structure of photonic emission or data capture. Through this mechanism, the AI-Gated photomodulation system 202 transforms conventional open-loop optical devices into closed-loop predictive platforms that dynamically adapt to the real-time physiologic state of the target tissue. This predictive synchronization yields improved signal-to-noise ratio, reduced artifact, enhanced reproducibility, and greater diagnostic and therapeutic precision across all supported modalities.

TABLE 5

Predictive Temporal Dynamics and Their Optical Manifestations Supporting AI-Gating

| Physiologic Micro-Cycle | Biological Source | Optical Manifestation (Real-Time Signal) | Temporal Behavior (Rise → Drift → Convergence → Plateau) | Predictive Value for AI-Gating | Resulting Optimization (Imaging/ Therapy) |
|---|---|---|---|---|---|
| Mitochondrial redox oscillations | Photoreceptor/RPE energetic cycling | NIR reflectance modulation; Raman redox-state instability | Descending noise → partial convergence → stability plateau | Forecasts metabolic receptivity | Triggers Raman capture or photomodulation during redox-quieting |
| Tear-film interference cycles | Tear-film breakup and renewal | Surface reflectance fluctuation; contrast instability | Rising interference → breakup peak → reformation plateau | Predicts optical clarity windows | Schedules reflectance/OCT acquisition during tear-film stability |
| Microsaccades and fixation drift | Oculomotor micro-movements | OCT alignment jitter; SLO motion vectors | Drift → jitter → stillness micro-phase | Predicts motion-quiescent intervals | Triggers high-precision OCT/OCTA capture |
| Choriocapillar is micro-pulsatility | Cardiac-linked perfusion modulation | OCTA decorrelation harmonics | High flow → harmonic convergence → flow regularity | Predicts stable perfusion phase | Captures high-SNR OCTA vasculature data |
| FAF oxidative-load fluctuations | Lipofuscin metabolic behavior | Autofluorescence texture variability | Granularity → deceleration → uniformity plateau | Predicts FAF clarity | Enhances FAF-based biomarker sensitivity |

TABLE 5-continued

Predictive Temporal Dynamics and Their Optical Manifestations Supporting AI-Gating

| Physiologic Micro-Cycle | Biological Source | Optical Manifestation (Real-Time Signal) | Temporal Behavior (Rise → Drift → Convergence → Plateau) | Predictive Value for AI-Gating | Resulting Optimization (Imaging/ Therapy) |
|---|---|---|---|---|---|
| Raman spectral stabilization plateaus | Chromophore equilibrium (lipids, bisretinoids, amyloid) | Baseline drift reduction; stable peak-to-baseline ratio | Noise → stabilization → peak clarity | Predicts biochemical readiness | Enables reliable Raman chemical fingerprinting |
| Reflectance coherence windows | Outer segment alignment; waveguide dynamics | Increased consistency of backscatter intensity | Scattering drift → coherence rise → stability plateau | Predicts optical clarity | Improves OCT structural delineation |
| Transient oxidative bursts | RPE & photoreceptor oxidative micro-events | FAF micro-flicker; NIR noise surges | Fluctuation → harmonic settling | Predicts low-oxidative windows | Protects against misinterpretation; synchronizes imaging |

Table 5 provides the scientific basis for how the disclosed AI-Gating system derives predictive temporal coherence from continuously fluctuating physiologic behavior. Retinal tissue is not static; it cycles rapidly through metabolic, perfusion, scattering, fluorescence, and motion-related micro-states, each leaving a measurable trace within the optical signal. Subtle shifts in reflectance, Raman spectral noise, autofluorescence texture, OCTA pulsatility, or microscopic motion are therefore not artifacts but active indicators of the tissue's evolving physiologic condition. By sampling these signals at high temporal frequency, the AI-Gated photomodulation system 202 reconstructs the trajectory of each biomarker, capturing its rise, drift, convergence, and short-lived plateau phases, to determine when the retina is transitioning into a state of physiologic coherence. Because these trajectories follow reproducible statistical patterns rather than random fluctuation, they become predictable.

AI-Gating uses this predictable temporal structure to forecast the next interval in which imaging or therapy will achieve maximal clarity, stability, or biologic receptivity. These characteristic physiologic cycles, their observable optical signatures, and the specific predictive value they contribute to gated acquisition demonstrate that the system's timing decisions arise from identifiable, quantifiable biologic inputs rather than from abstract inference. This framework also reveals the scientific basis for multimodal predictive fusion: periods of OCT structural stability, Raman spectral clarity, autofluorescence uniformity, and perfusion regularity often occur within overlapping physiologic windows, making synchronized gating across modalities both feasible and uniquely supported by the disclosed architecture.

5.3 AI-Gating Predictive Inference Engine

At the core of the AI-Gated photomodulation system 202 is the predictive inference engine 224, a computational layer designed not merely to classify what the tissue looks like at a given moment, but to determine how its physiologic state is evolving in time. Retinal tissue undergoes rapid fluctuations in reflectance, scattering behavior, autofluorescence emission, biochemical spectral signatures, perfusion regularity, and micro-motion. Although these fluctuations may appear random on a frame-by-frame basis, they follow reproducible short-range temporal patterns that can be identified and forecasted when analyzed as continuous multimodal data streams.

The predictive inference engine 224 analyzes these evolving temporal biomarkers and reconstructs their trajectories to determine whether the tissue is approaching or departing from a state of physiologic coherence. By evaluating the slope, convergence behavior, oscillation patterns, and stabilization phases of these biomarkers, the AI-Gated photomodulation system 202 forecasts the next interval in which the retina will be structurally stable, metabolically quiet, spectrally coherent, perfusion-regular, or motion-free. The resulting forecast is expressed as a continuously updated, time-indexed readiness estimate that identifies the optimal upcoming moments for diagnostic acquisition or photomodulation.

To generate these predictions, the AI-Gated photomodulation system 202 may employ a range of artificial intelligence methods. Neural network models learn complex spatial and spectral relationships within and across modalities, identifying subtle feature combinations that correlate with readiness for high-value imaging or therapeutic response. Recurrent architectures such as LSTM or GRU networks analyze sequential dependencies in the data, enabling short-range temporal forecasting rather than mere real-time reaction. Bayesian estimators quantify uncertainty and distinguish physiologic oscillations from unpredictable noise, allowing the system to suppress activity when prediction confidence is low. Optical-flow models interpret motion vectors to anticipate the onset of fixation stillness, while spectral-decomposition frameworks detect biochemical plateaus that mark periods of Raman or hyperspectral stability.

The disclosed architecture supports both single-modality and multimodal predictive fusion. When temporal trajectories from OCT, reflectance, OCTA, Raman, motion, or autofluorescence are analyzed in isolation, the AI-Gated photomodulation system 202 can still generate a forecast. However, when two or more modalities contribute synchronized temporal information, such as increasing OCT reflectance coherence occurring simultaneously with decreasing Raman variance or convergence of OCTA pulsatility patterns, the predictive confidence and physiologic specificity increase substantially. In multimodal embodiments, the AI-Gating engine 210 performs temporal fusion of structural, vascular, metabolic, and biochemical biomarkers to identify physiologic windows of stability.

The output of the predictive inference engine 224 forms the temporal foundation of AI-Gating. Instead of allowing imaging or therapy to proceed at arbitrary moments chosen by a technician or fixed clock interval, the AI-Gated photomodulation system 202 acts only when the tissue is forecasted to be in its most informative, stable, and receptive condition. In this way, the predictive engine 228 converts physiologic variability from an obstacle into a navigable timing signal, enabling a closed-loop, biologically synchronized mode of operation.

5.4 AI-Gating Decision Layer as Bridge between Prediction and Action

Once the predictive inference engine 224 has identified the forthcoming interval of physiologic stability, metabolic receptivity, spectral clarity, or motion quiescence, these forecasts enter the system's gating decision layer 210. This AI-Gating engine 210 serves as the operational bridge between prediction and action, determining not only whether the AI-Gated photomodulation system 202 should interact with the tissue, but also the precise manner and timing of that interaction. Rather than treating illumination or imaging as fixed, operator-initiated events, the AI-Gating engine 210 transforms them into biologically synchronized processes that occur only when the tissue is forecasted to be in a favorable physiologic state.

At each moment, the AI-Gated photomodulation system 202 evaluates the predicted readiness of the tissue and determines whether imaging or photomodulation should proceed, be delayed, or be temporarily suppressed. If the model anticipates that the tissue is about to enter a window of structural coherence, metabolic quieting, perfusion regularity, or motion stillness, the gate opens and permits acquisition or light delivery. If the tissue is forecasted to transition into instability, such as increased scatter noise, perfusion turbulence, oxidative fluctuation, or fixation drift, the gate inhibits activity, preventing low-value data capture and avoiding unnecessary exposure. When the AI-Gated photomodulation system 202 detects that an optimal interval is imminent but not yet present, the gating layer withholds action until the highest-value physiologic moment is reached.

The AI-Gating engine 210 also controls how the AI-Gated photomodulation system 202 acts, not merely when. It may adjust photonic parameters such as wavelength composition, fluence, pulse duration, repetition pattern, or duty cycle, or it may refine imaging behavior by modulating acquisition timing, averaging, or sampling density. Through this adaptive modulation, the device no longer operates as a static emitter or passive camera, but as a responsive platform capable of tailoring its output to the physiologic state of the tissue.

5.5 Comparison of Open-Loop and Closed-Loop Photomodulation Systems

Open-loop technologies deliver imaging or light output according to fixed settings, pre-programmed timing, or technician activation. In an open-loop system, the device assumes that the tissue is stable and ready, regardless of whether the retina is in motion, metabolically stressed, or undergoing rapid physiologic fluctuation. As a result, image quality, biomarker sensitivity, and treatment consistency depend heavily on chance timing and operator technique, leading to variability across patients and visits.

In contrast, closed-loop technology, as deployed in the AI-Gated photomodulation system 202, continually measure the state of the tissue and use that information to guide what the system does next. Instead of operating blindly, a closed-loop system receives feedback, such as motion stability, reflectance coherence, perfusion regularity, or spectral clarity, and adjusts its behavior in real time. The device can delay, permit, or modulate imaging or light delivery based on physiologic readiness rather than rigid schedules or technician judgment.

This shift from open-loop to closed-loop control is significant in ophthalmology because many retinal biomarkers and therapeutic response states are transient and timing-dependent. By aligning system activation with short-lived periods in which the tissue is most stable or most receptive, closed-loop operation enables higher-value data capture, more reproducible monitoring, and safer, more efficient photonic intervention, without requiring changes to the underlying hardware.

Figure 5:
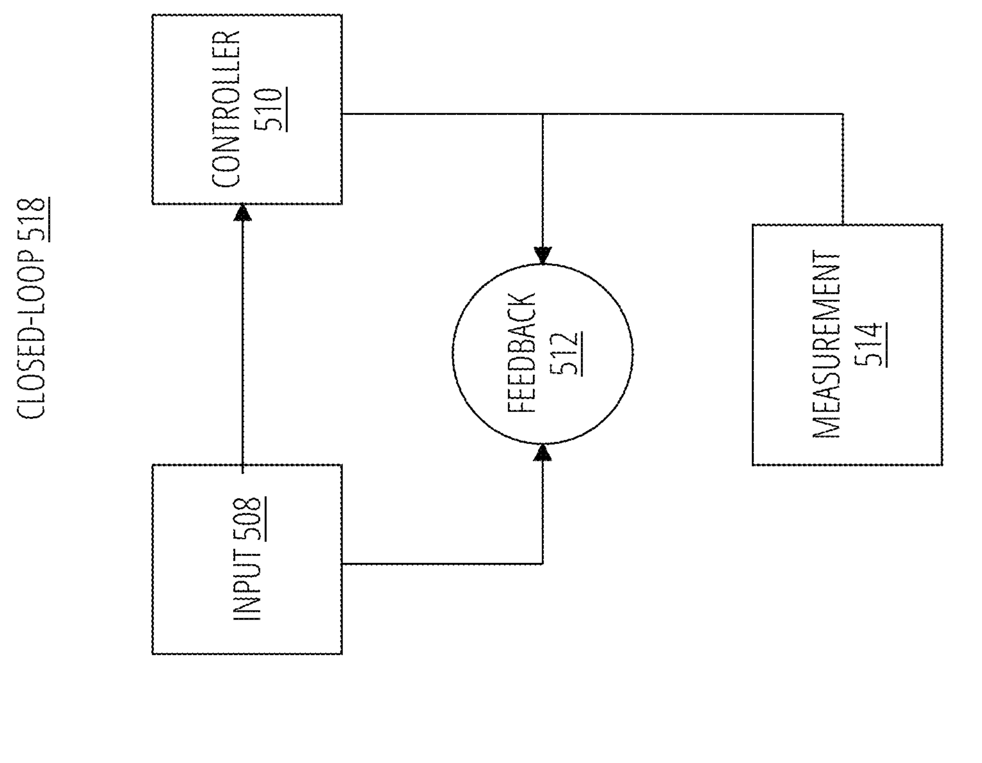
FIG. 5 illustrates open-loop and closed-loop systems.
Figure 5:
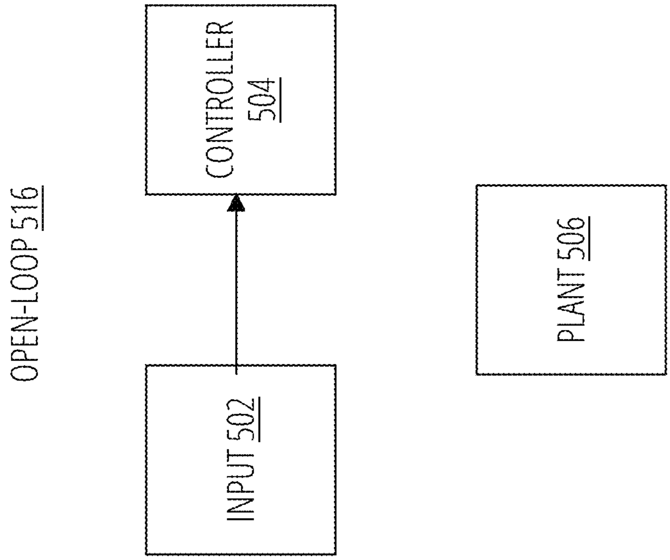

FIG. 5 shows a comparison of open-loop 516 illumination and imaging control (left) versus closed-loop 518 AI-Gated control (right). In the open-loop 516 configuration, the system issues a command (input 502) to the controller 504 without regard to the instantaneous retinal physiologic state, and the plant 506 receives energy or instructions without feedback refinement.

In the closed-loop 518 configuration, real-time retinal signals are measured 514 and returned to the controller 510, enabling predictive analysis of the retinal physiologic state and generation of a gating signal that permits or suppresses emission based on optimal physiologic and optical conditions. This closed-loop 518, feedback-driven 512 operation forms the basis of AI Predictive Gating.

TABLE 6

Comparison of Open-Loop and Closed-Loop Gating Architectures

| Characteristic | Open-Loop (Static Timing) | Closed-Loop Predictive Gating (AI-Based) |
|---|---|---|
| Timing Control | Fixed or preprogrammed; independent of tissue conditions | Dynamically predicts optimal intervals based on real-time physiologic and optical feedback |
| Responsiveness to Tissue Variability | None; assumes stability | High; continuously adapts to motion, perfusion changes, reflectance stability, and metabolic signals |
| Image & Spectral Quality | Subject to motion artifacts, perfusion fluctuations, and noise | Maximized through alignment with physiologically stable windows, improving SNR and structural fidelity |
| Biomarker Sensitivity | Inconsistent detection of subtle or transient biomarkers | Enhanced detection of mitochondrial signals, drusen spectral signatures, FAF texture changes, and perfusion shifts |
| Reproducibility Across Sessions | High variability due to technician or patient factors | Low variability; acquisition occurs consistently at predicted stable intervals |
| Therapeutic | Light delivered regardless of | Energy delivered only when tissue is |

TABLE 6-continued

| Comparison of Open-Loop and Closed-Loop Gating Architectures | | |
|---|---|---|
| Characteristic | Open-Loop (Static Timing) | Closed-Loop Predictive Gating (AI-Based) |
| Photomodulation Safety | metabolic readiness | receptive, reducing unnecessary exposure |
| Multimodal Integration | Modalities operate independently without temporal coordination | OCT, OCTA, Raman, NIR reflectance, and photomodulation can be synchronized within the same physiologic gate |
| Clinical Interpretability | Dependent on operator technique and timing | More consistent datasets enabling reliable longitudinal monitoring |
| Applicability Across Tissues | Limited and modality-dependent | Extensible to retina, RPE, choroid, optic nerve head, trabecular meshwork, and other ocular or systemic tissues |

Table 6 contrasts the disclosed AI-based closed-loop 518 gating architecture with conventional open-loop 516 ophthalmic imaging and photonic delivery systems By highlighting differences in timing control, biologic responsiveness, biomarker fidelity, reproducibility, safety, and multimodal integration, Table 6 illustrates the structural and functional advantages that distinguish the closed-loop system from conventional loop systems.

TABLE 7

| Examples of Advantages of Closed-Loop Predictive Gating | |
|---|---|
| Advantage Category | Explanation |
| Improved Image and Spectral Quality | Temporal gating aligns acquisition with physiologically stable intervals, producing sharper OCT volumes, clearer Raman spectra, enhanced FAF signals, and higher signal-to-noise ratios across all modalities. |
| Enhanced Detection of Retinal Biomarkers | Signals associated with drusen composition, mitochondrial dysfunction, RPE oxidative load, metabolic transitions, choriocapillaris perfusion, and retinal pigment architecture are more reliably captured. |
| Reduced Variability Across Sessions and Devices | By aligning acquisition to biologic timing rather than technician timing, the system provides reproducible biomarker assessments for longitudinal monitoring. |
| Safety and Efficiency in Photomodulation | Therapeutic exposure occurs only when tissue is metabolically receptive, reducing unnecessary light dosage and enhancing biologic effect. |
| Foundation for Multimodal Fusion | Because gating occurs at the level of physiologic coherence, OCT, OCTA, Raman, NIR, FAF, and photomodulation can be temporally synchronized, enabling a richer diagnostic framework. |

Importantly, the AI-Gated Closed-Loop System supports multimodal and cross-modal gating, allowing two or more modalities to be triggered within the same predicted physiologic window. For example, OCT and Raman spectroscopy may be synchronized to capture structural and biochemical information during a shared period of retinal stability, or OCTA and autofluorescence may be aligned to obtain perfusion and oxidative signals under the same physiologic conditions.

Through this decision architecture, AI-Gating converts physiologic variability from a source of artifact into a source of control. Every frame of imaging and every pulse of light is delivered only when the tissue itself is biologically prepared to yield the highest diagnostic value or therapeutic benefit. In doing so, the system elevates ophthalmic imaging and photomodulation from a time-agnostic procedure to a fully adaptive, closed-loop interaction with living tissue-achieving a level of synchronization and multimodal integration that is not attainable with current technology.

Figure 6:
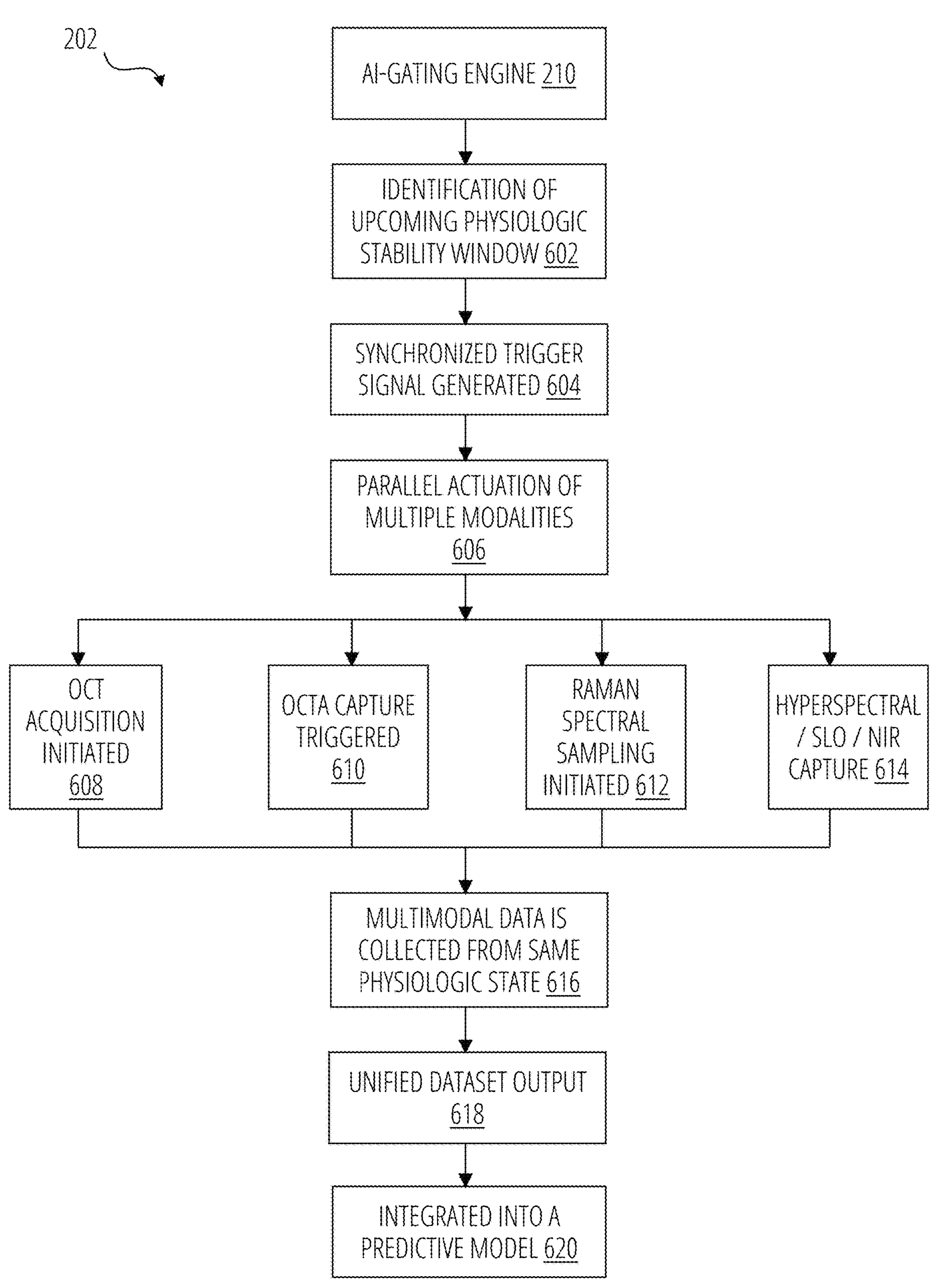
FIG. 6 illustrates a system architecture in which multiple imaging and spectroscopic modalities are triggered based on a predicted physiologic stability interval.

FIG. 6 depicts a system architecture in which multiple imaging and spectroscopic modalities are triggered based on a predicted physiologic stability interval rather than sequential timing, manual selection, or retrospective signal filtering.

The synchronized actuation of OCT, OCTA, Raman spectroscopy, and optional hyperspectral or SLO/NIR acquisition occurs within the same anticipated physiologic window, producing a dataset derived from a single tissue state rather than multiple heterogeneous time points. The resulting multimodal output is returned to the predictive model in a closed-loop manner, permitting temporal coherence across modalities that is not achievable in conventional ungated, sequential, or post-hoc alignment systems.

The AI-Gating engine 210 uses measurements and measurement history to identify an upcoming physiologic stability window 602. Once the timing is determined, a synchronized trigger signal is generated 604, causing parallel actuation of multiple modalities 606: OCT acquisition initiated 608, OCTA capture triggered 610, Raman spectral sampling initiated 612, and hyperspectral/SLO/NIR capture 614. The multimodal data is collected from same physiologic state 616, creating a unified dataset output 618. This unified dataset is then integrated into a predictive model 620.

5.6 Effective Resolution Enhancement Through Physiologic Synchronization

Although the disclosed AI-Gating architecture does not alter the intrinsic axial or transverse resolution of an OCT system, which remains determined by factors such as light-source bandwidth, central wavelength, and detector or spectrometer design, it materially improves the effective diagnostic resolution and usable-frame yield of both current and future OCT platforms. By synchronizing image acquisition to predicted intervals of physiologic stability, including reduced microsaccadic motion, increased reflectance coherence, and transient metabolic quieting, the AI-Gated photomodulation system 202 suppresses frame capture during periods of instability and permits acquisition only when structural boundaries are inherently clearer.

This timing-based control reduces motion artifact, segmentation variability, and frame discard rate, thereby enabling higher-fidelity visualization without any modification to the underlying hardware. In practical terms, physiologically synchronized acquisition increases the proportion of diagnostically usable frames compared with ungated imaging performed at arbitrary time points; for example, continuity of the ellipsoid zone is more reliably preserved when frames are captured during predicted motion-quiet intervals, and boundary-segmentation algorithms operate with greater consistency when reflectance coherence is maximized.

Although specific quantitative improvements depend on device implementation, these effects arise from temporal optimization rather than equipment changes, allowing the AI-Gated photomodulation system 202 to enhance diagnostic performance across existing OCT instruments as well as forthcoming high-resolution and extended-source iterations.

5.7 Algorithmic Basis for Predictive AI-Gating

The predictive capability and contribution of the AI-Gating engine 210 arises from the fundamental observation that retinal physiology, although dynamic, is not random. Optical, metabolic, and perfusion-based biomarkers follow discernible short-term and long-term temporal patterns driven by mitochondrial energetics, choriocapillaris micropulsatility, fluorescence decay behavior, tear-film oscillations, fixation micro-cycles, and Raman spectral stabilization phases. These physiologic transitions create repeatable intervals in which the tissue becomes optically coherent, metabolically quiet, or spectrally stable, precisely the moments when imaging or photomodulation is most effective.

To forecast these intervals, the AI-Gated photomodulation system 202 analyzes multimodal optical inputs not as isolated frames but as time-dependent signals exhibiting trajectories, oscillations, plateaus, and convergence patterns. The algorithmic stack is therefore designed to extract both instantaneous features (e.g., reflectance intensity, spectral purity) and temporal relationships (e.g., metabolic drift, motion quiescence cycles). By integrating spatial, spectral, and temporal information, the AI-Gating engine 210 becomes capable of predicting when the retina will transition into a physiologically favorable state, rather than merely reacting to real-time fluctuations.

Each class of algorithm contributes a distinct dimension of predictive intelligence. Neural networks specialize in detecting complex spatial and spectral patterns that correlate with retinal readiness. Recurrent architectures model short-term physiologic dynamics, enabling the AI-Gated photomodulation system 202 to anticipate transitions before they occur. Bayesian models quantify uncertainty, allowing the gating engine to suppress imaging during unstable or unpredictable intervals. Optical-flow methods track fixation and micro-movement, predicting when motion-free conditions will arise. Spectral unmixing algorithms detect biochemical stabilization windows, moments when Raman or hyperspectral signals are least contaminated by noise or vibrational interference.

Together, these computational frameworks transform physiologic variability into actionable temporal predictions. The AI-Gated photomodulation system 202 does not rely on chance "lucky frames," but instead forecasts when meaningful optical and metabolic signals will occur, ensuring that diagnostic acquisition and photomodulation are performed during the most informative and safest intervals.

TABLE 8

Algorithmic Methodology Supporting Predictive AI-Gating

| Algorithm Type | Application | Contribution to Gating |
|---|---|---|
| Neural Networks (CNN/MLP) | Feature extraction from multimodal data | Identify complex reflectance/metabolic patterns |
| Recurrent Models (LSTM/GRU) | Sequential and temporal data modeling | Capture time-linked biomarker fluctuations |
| Bayesian Models | Probabilistic state estimation | Quantify prediction confidence, suppress unstable periods |
| Optical-Flow Algorithms | Motion vector detection | Predict motion quiescence windows for imaging |
| Spectral Unmixing Models | Raman/hyperspectral analysis | Identify biochemical steady-states for acquisition |

Table 8 summarizes the computational methods used to forecast physiologic windows favorable for imaging or photomodulation. Each algorithm class contributes a distinct dimension of predictive intelligence, spatial feature extraction, temporal sequence modeling, probabilistic state estimation, motion prediction, or biochemical spectral stabilization, together enabling the AI-Gating engine 210 to anticipate optimal acquisition intervals rather than relying on moment-to-moment fluctuations.

5.8 Output and Actuation Layer

Once the gating decision layer determines that the tissue has entered, or is about to enter, a physiologically favorable interval, the AI-Gated photomodulation system 202 transitions into the photonic control 232 layer and actuation layer 236. These layers convert prediction into execution, carrying out the specific diagnostic or therapeutic action authorized by the AI-Gating engine 210. At this stage, the AI-Gated photomodulation system 202 may initiate OCT or OCTA acquisition precisely when reflectance coherence and motion quiescence are forecast to converge, or it may trigger fundus reflectance, autofluorescence, hyperspectral sampling, or scanning-laser imaging during predicted intervals of optical stability.

For biochemical interrogation, the photonic control 232 and actuation layer 236 enables Raman spectroscopy only during forecasted spectral plateau states, when metabolic noise and vibrational interference are minimized. Likewise, when the predictive engine 228 identifies a period of mitochondrial quieting or metabolic receptivity, the AI-Gated photomodulation system 202 permits photomodulation pulses to be delivered during those biologically favorable moments. In this way, the AI-Gated photomodulation system 202 ensures that every imaging frame and every photon of therapeutic light is delivered at a time when the tissue can yield maximum diagnostic clarity or therapeutic benefit.

The photonic control 232 and actuation layer 236 also dynamically modulate the characteristics of the AI-Gated photomodulation system 202 output based on predicted physiologic readiness. Photonic parameters, including wavelength composition, fluence, pulse duration, repetition structure, and duty cycle, may be adapted in real time, just as imaging parameters such as acquisition timing, sampling density, or dwell period may be refined to preserve fidelity under changing physiologic conditions. This adaptability allows each action to be tailored to the evolving metabolic, structural, or perfusion state of the tissue.

The disclosed architecture supports multimodal and cross-modal actuation, enabling two or more modalities to be triggered within the same predicted physiologic window. For example, OCT, Raman spectroscopy, fundus autofluorescence, and near-infrared reflectance may be executed in synchrony, allowing structural, biochemical, vascular, and optical information to be captured from the same physiologic state rather than from unrelated moments in time.

Every actuation event is timestamped and linked to the physiologic conditions under which it occurred. These data are immediately returned to the predictive engine 228, allowing the model to update its internal temporal maps and refine its future forecasts. Over repeated sessions, the AI-Gated photomodulation system 202 learns how an individual eye behaves, how frequently stability windows arise, how long metabolic quieting persists, how perfusion rhythms vary, and how motion patterns evolve, resulting in progressively more patient-specific timing and output control.

Through the photonic control 232 and actuation layer 236, the AI-Gated photomodulation system 202 completes its transition from physiologic prediction to physiologically synchronized action. By ensuring that every diagnostic and therapeutic event occurs only at the biologically most meaningful moment, the AI-Gated photomodulation system 202 maximizes imaging fidelity, enhances biomarker detectability, improves therapeutic efficiency, and establishes a closed-loop operational model.

5.9 AI-Gated Closed-Loop Feedback Integration

A feature of the disclosed architecture is its closed-loop operation, in which every imaging acquisition and every therapeutic pulse becomes new physiologic information that is immediately incorporated back into the predictive model. Once an actuation event occurs, whether an OCT frame is captured, a Raman spectrum is obtained, an OCTA sequence is recorded, or a photomodulation pulse is delivered, the AI-Gated photomodulation system 202 analyzes the resulting tissue response and compares it to the predicted physiologic state. This post-actuation assessment reveals whether the retina behaved as anticipated during the projected interval of structural stability, metabolic receptivity, spectral coherence, or perfusion regularity.

When deviations arise, the AI-Gated photomodulation system 202 adapts. For example, if a Raman acquisition yields lower-than-expected signal-to-noise, the model interprets this discrepancy as evidence that the predicted biochemical plateau was less stable than forecasted, prompting refinement of the temporal readiness mapping. Conversely, if an OCT frame exhibits unusually high reflectance coherence and boundary sharpness, this reinforces the accuracy of the structural-stability prediction and strengthens future estimates of motion quiescence.

Subtle shifts in autofluorescence or reflectance following photomodulation pulses provide further insight into how the tissue transitions between receptive and non-receptive states, enabling the AI-Gated photomodulation system 202 to refine its understanding of metabolic cadence. Likewise, changes in choriocapillaris pulsatility or decorrelation harmonics observed on OCTA feed back into the vascular-timing model, improving future prediction of perfusion-stable intervals.

Because these feedback signals are derived from multimodal physiologic responses, the AI-Gated photomodulation system 202 benefits from a uniquely rich and cross-validated learning process. The disclosed platform continuously recalibrates itself using real biological outcomes generated during each actuation event. This closed-loop behavior allows the predictive engine 228 to improve its accuracy over both short and long timescales: predictions for the next few seconds evolve based on immediate optical responses, while longitudinal performance, spanning multiple visits or treatment cycles, adapts to patient-specific physiologic patterns.

Over time, the AI-Gated photomodulation system 202 becomes increasingly personalized, learning the characteristic frequency of a patient's microsaccades, the duration and recurrence of their mitochondrial quieting phases, and the rhythmic behavior of their choriocapillaris perfusion. This progressive adaptation transforms the platform into a self-correcting, physiologically synchronized system that continuously aligns its operational timing with the evolving state of living tissue.

Through this closed-loop feedback mechanism, the AI-Gated photomodulation system 202 establishes an adaptive architecture. Rather than assuming stability, the AI-Gated photomodulation system 202 verifies and re-predicts it, ensuring that future imaging and therapeutic events are executed with increasing precision, reliability, and biologic relevance. This capability is important to enabling the disclosed multimodal predictive fusion, which depends on accurate and continuously refined temporal alignment across structural, vascular, biochemical, and reflectance-based modalities.

TABLE 9

AI-Gated versus Conventional Ungated Acquisition Performance

| Performance Domain | AI-Gated Acquisition (Predictive Physiologic Synchronization) | Resulting Impact |
|---|---|---|
| Timing Control | Acquisition triggered only during predicted physiologic stability | Eliminates timing variability and reduces low-value captures |
| Structural Image Fidelity | Capture aligned to motion-free and reflectance-coherent intervals | Sharper layer boundaries and improved segmentation reliability |

TABLE 9-continued

AI-Gated versus Conventional Ungated Acquisition Performance

| Performance Domain | AI-Gated Acquisition (Predictive Physiologic Synchronization) | Resulting Impact |
|---|---|---|
| Spectral/Biochemical Signal Quality | Acquisition restricted to metabolic quieting and spectral plateau phases | Higher signal-to-noise ratios and more reproducible biochemical profiles |
| Perfusion and Flow Mapping | Triggered during predicted perfusion-regularity windows | Clearer visualization of microvasculature and reduced flow artifact |
| Autofluorescence Stability | Capture during uniform fluorescence intervals | More consistent metabolic assessment and improved longitudinal tracking |
| Reproducibility Across Sessions | Standardized to comparable physiologic states | Enables reliable trajectory-based monitoring rather than snapshot comparison |
| Therapeutic Energy Delivery (Photomodulation) | Exposure allowed only during predicted receptive intervals | Reduced cumulative exposure and enhanced therapeutic efficiency |
| Multimodal Synchronization | OCT, OCTA, reflectance, Raman, and FAF triggered within the same physiologic window | Enables coherent multimodal datasets not achievable with open-loop systems |
| System Intelligence Over Time | Closed-loop learning refines timing predictions per individual | Progressive personalization and safety optimization |

The analysis presented in Table 9 demonstrates that the advantages of AI-Gated acquisition arise from predictive physiologic synchronization. The disclosed AI-Gated architecture restricts acquisition to short-lived intervals in which the retina exhibits predicted physiologic coherence, such as motion-quiet periods, reflectance-stable phases, perfusion-regularity windows, or biochemical plateau states. Capturing data only during these intervals materially improves effective diagnostic resolution and significantly increases the proportion of usable frames. Structural imaging demonstrates sharper boundaries and more reliable segmentation, spectral measurements present higher signal-to-noise ratios, and perfusion maps display clearer microvascular detail with reduced decorrelation artifact.

A further consequence of physiologically synchronized timing is improved longitudinal reproducibility. Rather than comparing snapshots collected under uncontrolled conditions, serial examinations are standardized to comparable physiologic states, enabling true trajectory-based monitoring of disease progression rather than variability-driven interpretation. This same temporal selectivity enhances the safety and efficiency of photomodulation, permitting energy delivery only during predicted receptive intervals and avoiding unnecessary exposure.

6.0 Multimodal Integration

The AI-Gated photomodulation system 202 is designed to unite multiple optical modalities within a single predictive, physiologically synchronized framework. Although each modality, such as OCT, OCT angiography, Raman spectroscopy, autofluorescence imaging, or photomodulation, could be operated independently and without regard to inherent tissue timing, the AI-Gated photomodulation system 202 transforms them into coordinated components of a unified multimodal engine. Each modality responds to a different facet of retinal physiology: OCT reflects structural coherence; OCTA captures perfusion regularity; Raman spectroscopy reveals biochemical stabilization; FAF expresses oxidative behavior; and photomodulation depends on mitochondrial receptivity. These physiologic states do not arise simultaneously by chance; rather, they occur within brief yet predictable intervals of alignment that the unaided human operator cannot anticipate.

AI-Gating identifies these intervals by continuously analyzing temporal biomarkers from all available input streams. As the AI-Gated photomodulation system 202 forecasts the moment when structural stillness, vascular regularity, biochemical stability, and metabolic quieting converge, it orchestrates the actions of each modality accordingly. OCT frames may be triggered exactly when reflectance coherence peaks; OCTA acquisition may be delayed until the next pulsatile perfusion plateau; Raman spectroscopy may be initiated only when spectral variance falls into a plateau state; and autofluorescence may be captured during a fleeting moment of oxidative quieting. Photomodulation pulses, in turn, are delivered only when mitochondrial behavior indicates metabolic receptivity rather than stress or saturation.

Because all modalities follow the same physiologic timeline generated by AI-Gating, the resulting datasets are temporally harmonized, inherently comparable, and free from the inconsistencies that plague conventional open-loop imaging. Multimodal data acquired in this synchronized manner create a coherent portrait of the tissue's structural, vascular, metabolic, and biochemical state, all recorded during the same period of physiologic stability. This predictive alignment enhances diagnostic confidence, strengthens longitudinal comparisons, and enables a level of multimodal coherence that has not previously been achievable.

6.1 Ophthalmic and Systemic Applications of AI-Gating

The predictive framework enabled by AI-Gating is not limited to a single disease or imaging modality; it is fundamentally applicable to any ophthalmic or systemic condition in which tissue physiology fluctuates over time. Because the AI-Gated photomodulation system 202 interprets universal optical biomarkers, such as reflectance coherence, spectral variance, fluorescence stability, biochemical Raman signatures, and perfusion regularity, it can adapt seamlessly to the molecular and structural behaviors of diverse tissues. Many retinal and systemic diseases exhibit characteristic temporal transitions in their metabolic, vascular, or biochemical states, and these transitions form ideal substrates for AI-Gated physiologic prediction.

In age-related macular degeneration, for example, the retina oscillates between intervals of oxidative load, mitochondrial fatigue, perfusion irregularity, and brief periods of metabolic quieting. AI-Gating captures these transitions and synchronizes imaging or photomodulation to the windows in which drusen morphology, RPE lipofuscin behavior, and choriocapillaris perfusion most accurately reflect disease status. A similar advantage emerges in toxic maculopathies such as hydroxychloroquine exposure, where subtle defects in photoreceptor and RPE physiology become detectable only when imaging is matched to stable, low-noise intervals.

Inherited retinal dystrophies, mitochondrial disorders, and conditions involving metabolic instability show especially pronounced physiologic variability that often masks early pathology during conventional, ungated imaging. By forecasting the brief periods when mitochondrial redox behavior stabilizes or when outer-segment reflectance becomes coherent, AI-Gating allows earlier and more reliable identification of degenerative change. In systemic amyloid disease, the biochemical signatures present within drusen or subretinal deposits appear inconsistently across time; gating Raman acquisition to predicted spectral stability windows markedly enhances the clarity and reproducibility of these subtle amyloid peaks.

Inflammatory conditions and ocular perfusion disorders also benefit from predictive timing, as their biomarkers often fluctuate with perfusion micro-pulsatility, oxidative bursts, or transient refractive irregularities. AI-Gating identifies the moments when inflammatory scatter is lowest or when perfusion harmonics stabilize, enabling cleaner capture of clinically relevant features. Across all of these applications, the key advantage is that imaging or photomodulation are no longer tied to technician timing or arbitrary acquisition intervals, but instead to the biologic rhythm of the tissue itself. AI-Gating transforms the system into an adaptive platform that acts only during physiologically meaningful moments, substantially improving disease detection, monitoring, and therapeutic precision across a broad range of ophthalmic and systemic conditions.

6.2 Deployment Configurations (Standalone and Integrated Embodiments)

The disclosed AI-Gating architecture is intentionally designed to operate across a broad range of deployment models, allowing the technology to be embedded directly into new optical systems or added onto existing commercial platforms without structural modification. At its core, AI-Gating acts as a physiologically informed timing engine: it receives optical input streams, interprets temporal biomarkers, forecasts upcoming stability windows, and issues gating commands that synchronize imaging or photonic exposure with the tissue's moment-to-moment physiologic readiness. Because this predictive intelligence is modality-agnostic, the same algorithmic foundation can be deployed in multiple hardware configurations.

In its standalone embodiment, AI-Gating functions as a purely software-based controller operating alongside commercial imaging devices. In this configuration, the AI-Gated photomodulation system 202 ingests optical or physiologic signals from an external device, such as OCT, OCTA, FAF, Raman, reflectance, or hyperspectral instruments, and produces gating directives without requiring any modification to the host hardware.

This approach allows AI-Gating to upgrade existing clinical devices with predictive physiologic timing, transforming their fixed, technician-driven acquisition schedules into biologically optimized ones. The standalone embodiment demonstrates that AI-Gating is not dependent on proprietary hardware integration; it operates as an independent layer of intelligence capable of elevating the performance of legacy instrumentation.

An integrated embodiment incorporates AI-Gating directly into a unified multimodal platform, such as a system combining OCT, Raman spectroscopy, reflectance imaging, and photomodulation. In this configuration, the predictive timing engine shares internal clocks, optical channels, and hardware resources, enabling exceptionally tight temporal coordination across all modalities. Integrated systems benefit from high-frequency synchronization and rapid cross-modal feedback, allowing the device to capture structural, vascular, metabolic, and biochemical information within the same physiologic window. By acting as the central controller of the optical platform, AI-Gating ensures that every subsystem delivers or receives information at the biologically most coherent moment.

The architecture also supports portable and handheld embodiments, in which the predictive timing engine is embedded into compact devices used for field diagnostics, remote screenings, telemedicine, or home monitoring. In these contexts, physiologic fluctuations are often more pronounced and less controlled, making predictive gating especially valuable. The handheld versions rely on lightweight inference models that maintain the same temporal-prediction capabilities while operating with reduced computational and power resources.

In a cloud-connected or distributed embodiment, AI-Gating coordinates data from multiple geographically dispersed devices. Physiologic timing maps, temporal biomarkers, and predictive models can be shared or aggregated across patients, enabling population-scale screening systems that maintain consistent diagnostic standards. In longitudinal monitoring, cloud-based gating allows individual patients to be tracked with high temporal fidelity, even when data are acquired across different sites or devices.

Finally, the AI-Gated photomodulation system 202 supports a multi-device network embodiment, in which multiple imaging or therapeutic instruments operate as a coordinated ecosystem. Instead of relying on mechanical or operator-defined schedules, the devices share a common physiologic timeline derived from AI-Gating. This allows, for example, an OCT device, a Raman instrument, and a photomodulation source to operate in synchronized physiologic alignment, even if they are physically separate devices. The network embodiment demonstrates how AI-Gating can unify heterogeneous optical technologies into a single adaptive diagnostic infrastructure driven by real-time biology rather than workflow constraints.

Across all embodiments, standalone, integrated, portable, cloud-connected, and networked, the defining element is the same: AI-Gating establishes physiologic readiness as the master clock for optical imaging and photonic therapy. Whether functioning as an add-on intelligence layer or an embedded system controller, AI-Gating ensures that acquisition and treatment occur not when it is convenient for the machine, but when the tissue itself is most stable, most receptive, and most diagnostically revealing.

TABLE 10

Comparative Deployment Configurations for AI-Gating

| Deployment Embodiment | Description | Role/Function of AI-Gating | Primary Advantages |
|---|---|---|---|
| Standalone Embodiment | Operates as a software-based predictive controller connected to existing commercial imaging or therapeutic devices. | Interprets incoming optical streams and issues gating commands without modifying the host hardware. | Enables immediate upgrade of legacy systems; device-agnostic; lowest barrier to implementation. |
| Integrated Embodiment | AI-Gating is embedded directly into a unified optical platform (e.g., OCT + Raman + reflectance + photomodulation). | Serves as the master physiologic timing engine coordinating all modalities using shared clocks and optical channels. | Provides maximal synchronization; highest precision; native multimodal fusion. |
| Portable/ Handheld Embodiment | Miniaturized version suitable for clinic-to-field use, remote care, or home monitoring. | Uses lightweight predictive models to maintain physiologic gating despite variable environments. | Ideal for screening, telemedicine, mobile diagnostics; stable performance under motion and environmental variability. |
| Cloud-Connected/ Distributed Embodiment | Devices upload physiologic timing data and biomarker trajectories to cloud infrastructure for population-level analysis. | Aggregates temporal biomarkers across patients; refines predictive readiness models; supports remote physiologic alignment. | Enables large-scale screening, remote follow-up, and longitudinal alignment across multiple locations. |
| Multi-Device Network Embodiment | Multiple devices function as a coordinated diagnostic ecosystem sharing a common physiologic timeline. | Synchronizes imaging and therapy across independent instruments based on predicted stability windows. | Creates unified diagnostic workflows, cross-system coherence, and multi-instrument physiologic synchronization. |

6.3 Illustrative Elements of Predictive AI-Gating

Across every embodiment, the disclosed AI-Gating architecture transforms optical imaging and photomodulation into a physiology-synchronized, time-optimized, and fully adaptive closed-loop process. AI-Gating continuously interprets reflective, metabolic, biochemical, and perfusion-related signals to anticipate when the tissue is most capable of providing diagnostically meaningful information or responding safely and effectively to photonic stimulation. By gating acquisition or therapy to these predicted high-value intervals, the AI-Gated photomodulation system 202 achieves levels of consistency, clarity, and biologic precision that were not previously attainable.

This predictive physiologic alignment yields profound improvements across all major optical modalities. OCT imaging benefits from enhanced sharpness and more stable boundary segmentation due to alignment with intervals of reduced motion and increased reflectance coherence. OCTA acquires perfusion maps during rhythmic windows of flow regularity, producing more reliable representations of flow voids and microvascular behavior. Raman spectroscopy, which is exquisitely sensitive to metabolic noise, demonstrates markedly improved spectral clarity and biochemical detectability when captures occur during metabolically quiet intervals forecasted by the AI-Gating engine 210. Similarly, fundus autofluorescence becomes far more interpretable when exposures are timed to moments of oxidative stability, reducing artifacts and improving the accuracy of lipofuscin and bisretinoid assessments.

The benefits extend beyond individual modalities. By synchronizing all imaging and therapeutic activities to a unified physiologic timeline, multimodal datasets become inherently aligned in both time and biologic state. This temporal fusion enhances early disease detection, strengthens cross-modal comparisons, and establishes a solid foundation for longitudinal monitoring of conditions such as age-related macular degeneration, inherited retinal dystrophies, toxic maculopathies, inflammatory disorders, and systemic diseases with ocular biomarkers. Variability between visits, often a major limitation in conventional imaging, is greatly reduced because each acquisition is captured under physiologically comparable conditions rather than arbitrary temporal sampling.

AI-Gating also elevates photomodulation from a generic light-delivery procedure to a biologically tuned therapy. By predicting mitochondrial receptivity and suppressing exposure during periods of metabolic vulnerability, the AI-Gated photomodulation system 202 ensures that therapeutic photons are delivered only when they are most likely to exert beneficial effects and least likely to cause stress, thereby improving safety and maximizing therapeutic impact.

Taken together, these capabilities establish a novel control architecture for optical diagnostics and therapy. The AI-Gated photomodulation system 202 no longer waits for physiologic stability to occur by chance, nor does it operate blindly through periods of instability. Instead, it anticipates biologic readiness, acts only during physiologically meaningful intervals, and continuously adapts its decisions based on real-time and historical feedback. Through this predictive and closed-loop integration, AI-Gating enables reproducible, high-fidelity imaging and safe, precisely timed photomodulation, advancing the entire field t and establishes a new approach for an intelligent, physiology-aware operation.

6.4 Overview of System Operation

The AI-Gated photomodulation system 202 functions as an adaptive photonic and diagnostic platform that continually interprets optical and physiologic signals to determine the optimal timing for illumination and image acquisition. As the AI-Gated photomodulation system 202 begins operation, it gathers a continuous stream of data reflecting the tissue's structural, metabolic, and mechanical behavior. These data include reflectance patterns, depth-resolved scattering information, autofluorescence characteristics, near-infrared signatures, perfusion metrics, and motion-related signals such as microsaccades and blink activity.

Each incoming dataset is routed into the internal processing pipeline, where the AI-Gating engine 210 evaluates the evolving physiologic state. Rather than responding to a static measurement, the system interprets temporal trajectories, patterns that reveal when reflectance coherence strengthens, autofluorescence stabilizes, or motion jitter decreases. These temporal cues serve as predictors of when the tissue is most amenable to either photonic emission or diagnostic imaging.

When the predictive engine 228 identifies a favorable interval, the AI-Gated photomodulation system 202 issues a gating signal instructing the photonic or imaging modules to operate during this physiologically advantageous window. After each emission or capture event, the resulting tissue responses are reacquired by the sensors and fed back into the model. This dynamic feedback loop continuously refines predictions and enhances synchrony between system operations and tissue physiology.

6.5 Physiologic State of Target Tissue for AI-Gating

The diagnostic and therapeutic performance of optical systems is profoundly influenced by the temporal physiologic state of biological tissue. At any moment, tissue exhibits dynamic fluctuations in scattering behavior, metabolic activity, perfusion regularity, autofluorescence stability, and biochemical composition. These fluctuations, though appearing random to the unaided observer, follow statistically predictable trajectories over short time scales. The AI-Gated photomodulation system 202 leverages this phenomenon by identifying, modeling, and forecasting these physiologic rhythms, enabling imaging and photomodulation to occur during the most diagnostically meaningful intervals.

6.6 Scientific Basis and Rationale for Predictive AI-Gating

The retina is an inherently dynamic structure whose optical and metabolic characteristics fluctuate continuously across milliseconds to seconds. At any given moment, its mitochondria shift between polarized and depolarized states; its microvasculature modulates flow in rhythm with cardiac pulsatility; the tear film undergoes cycles of thinning and reformation that alter surface reflectance; photoreceptors drift subtly with microsaccades; and chromophores, fluorophores, and Raman-active biochemical species oscillate in response to metabolic demand. These rapid physiologic variations shape every optical interaction occurring within retinal tissue, influencing how light is absorbed, scattered, reflected, and emitted.

Other imaging and illumination systems treat these variations as noise rather than signal. They operate in an open-loop manner, capturing frames or delivering light at predetermined intervals without regard for whether the tissue is optically stable, metabolically quiet, or vascularly coherent at that moment. As a result, a single microsaccade can degrade an OCT volume; a brief period of perfusion instability can distort an OCTA en face map; oxidative microbursts can corrupt fundus autofluorescence; and transient mitochondrial redox fluctuations can alter the fidelity of Raman spectral peaks. In this open-loop paradigm, the timing of acquisition rarely aligns with moments when the tissue is optimally ready to reveal accurate structural or biochemical information.

Predictive AI-Gating is specifically designed to overcome this fundamental limitation. Instead of reacting solely to instantaneous input, the AI-Gated photomodulation system 202 interprets the temporal evolution of the optical signals themselves. Physiologic fluctuations, although seemingly random, follow statistically recognizable trajectories, such as the rise and decay of mitochondrial redox states, the rhythmic regularity of choriocapillaris perfusion, the drift-and-plateau cycle of fixation stability, the periodic stabilization of autofluorescence patterns, and the spectral settling behavior of Raman peaks. These micro-rhythms become temporal biomarkers that indicate whether the tissue is approaching a state of coherence or instability.

Because physiologic state is directly encoded in optical behavior, the AI-Gated photomodulation system 202 is able to forecast future optical quality by analyzing these temporal biomarkers. When the biomarkers converge toward stability, the retina enters a high-value interval in which reflectance becomes more coherent, metabolic noise diminishes, Raman signatures sharpen, autofluorescence smooths, and perfusion becomes more uniform. Predictive AI-Gating identifies these transitions before they occur, enabling the AI-Gated photomodulation system 202 to act preemptively, opening the gate for imaging or illumination when the tissue is poised to provide maximal diagnostic fidelity or therapeutic receptivity. Conversely, when biomarkers drift toward instability, such as during fixation perturbations, perfusion irregularities, oxidative spikes, or redox turbulence, the AI-Gated photomodulation system 202 suppresses acquisition automatically.

This predictive timing capability is important because many of the most clinically relevant biomarkers in retinal disease are fragile. Raman biochemical signatures of drusen components, for example, can shift with minute changes in mitochondrial state. OCTA flow motifs deteriorate abruptly during phases of pulsatility. FAF texture becomes noisy during oxidative fluctuations. When these biomarkers are captured at suboptimal moments, their diagnostic meaning is obscured. AI-Gating ensures that they are measured during the rare intervals in which the retina expresses them with maximal clarity.

Viewed broadly, the predictive AI-Gating engine 210 functions as a temporal bridge between biology and technology. It continuously interprets physiologic micro-states, anticipates when the retina will enter an optically coherent or metabolically receptive phase, and restricts interaction to those physiologic windows. This transforms reflectance from a passive readout into an active guide: instead of merely describing tissue, reflectance behaviors become predictive indicators that determine when imaging or therapy should occur. In doing so, the AI-Gated photomodulation system 202 fundamentally redefines the timing architecture of optical diagnostics and photomodulation, from fixed scheduling to adaptive, biologically synchronized operation.

This predictive framework represents a natural evolution of the reflective paradigm underpinning all ophthalmic imaging. It enables the device to engage the retina only when the tissue is capable of revealing meaningful information or responding constructively to light. The result is a profound enhancement in structural fidelity, vascular clarity, biochemical detectability, and therapeutic safety, establishing a novel standard for physiologically aligned optical performance.

TABLE 11

Physiologic and Optical Foundations Underlying Predictive AI-Gating

| Physiologic Source | Optical Manifestation | Temporal Behavior | Predictive Value for AI-Gating | Impact on Imaging or Photomodulation |
|---|---|---|---|---|
| Mitochondrial redox oscillations and membrane-potential transitions | NIR reflectance variability, Raman redox peak shifts, subtle EZ reflectance changes | Millisecond-scale oscillations with identifiable quieting plateaus | Indicates when metabolic noise is low and biochemical signatures are stable | Enables high-fidelity Raman capture and optimizes timing for photomodulation receptivity |
| Choriocapillaris micro-pulsatility and perfusion rhythms | OCTA decorrelation stability, flow-void pattern regularity, NIR backscatter modulation | Rhythmic micro-pulsatility tied to cardiac cycle | Predicts impending phases of smooth perfusion | Improves OCTA flow mapping, reduces vascular noise, enhances detection of ischemic micro-patterns |
| Tear-film break-up and reformation cycles | Surface reflectance fluctuations, variations in FAF excitation efficiency | Repetitive cycles of break-up, thinning, and smoothing | Identifies windows when the tear film produces uniform surface optics | Enhances clarity of reflectance, FAF, and SLO-based fixation monitoring |
| Microsaccades, tremor, drift, and fixation settling | Reflectance jitter, OCT alignment noise, Raman acquisition instability | Predictable clusters of motion followed by transient motion-free intervals | Allows anticipation of motion-quiescence periods | Enables sharper OCT volumes, fewer motion artifacts, more stable multimodal acquisition |
| Transient oxidative bursts (RPE photochemistry) | FAF granularity changes, fluctuating fluorophore intensity | Rapid transitions driven by metabolic load and RPE oxidative state | Predicts when oxidative flicker will subside | Improves FAF interpretation and early detection of lipofuscin and bisretinoid behavior |
| Chromophore and fluorophore decay kinetics | Hyperspectral and Raman spectral stabilization plateaus | Convergence of spectral variability into stable plateaus | Signals when spectral noise is falling into a detectable steady-state | Allows biochemical signatures (lipids, bisretinoids, amyloid) to be measured reliably |
| Outer-segment alignment and photoreceptor scattering dynamics | Reflectance coherence windows, EZ-band definition, reduced layer jitter | Momentary improvements in optical coherence linked to structural stability | Predicts upcoming structural clarity | Enhances OCT segmentation accuracy and detection of subtle pathology |
| Perfusion-driven reflectance states of the choroid | NIR intensity modulations, subretinal scattering shifts | Semi-periodic fluctuations linked to microvascular tone | Identifies phases of choroidal stability | Enables precise NIR reflectance imaging and improves integration with OCTA timing |
| Biochemical micro-oscillations within drusen constituents | Raman fluctuations in amyloid, lipid oxidation, or bisretinoid peaks | Short-term oscillations with identifiable stabilization behavior | Predicts optimal biochemical measurement windows | Improves detectability of drusen molecular signatures and early AMD biomar |

6.7 Temporal Biomarkers as Inputs for Predictive AI-Gating

Temporal biomarkers are the foundational signals that allow the AI-Gated photomodulation system 202 to make physiologic predictions rather than merely respond to real-time input. A temporal biomarker is any optical or physiologic signal that fluctuates over time in a manner that reflects the underlying state of retinal or choroidal tissue. These fluctuations are not random; they carry physiologic meaning. When tracked continuously, they reveal when tissue is entering a period of stability or approaching a state of metabolic, structural, or vascular receptivity.

In practical terms, temporal biomarkers arise from every major imaging or sensing modality. OCT contributes dynamic variations in reflectance coherence and boundary sharpness; Raman spectroscopy exhibits changes in peak variance linked to mitochondrial redox activity; autofluorescence demonstrates granularity shifts that correlate with oxidative load; near-infrared reflectance reveals moment-to-moment scattering stability; OCT angiography carries rhythmic signatures of microvascular pulsatility; hyperspectral imaging displays emerging spectral plateau phases; motion tracking reveals fixation drift, tremor, and quiescent intervals; and tear-film behavior introduces oscillatory changes in surface clarity. Each of these fluctuating signals independently conveys a measure of tissue stability or instability.

However, the predictive value is enhanced when these biomarkers are fused. Combined across modalities, they form a high-dimensional temporal signature, an evolving physiologic trajectory that reflects not only the tissue's current state but also the direction in which that state is trending. Instead of treating any measurement as a static datapoint, the AI-Gating engine 210 examines the rate of change, slope, variance, periodicity, and convergence behavior of each biomarker. It analyzes whether Raman variance is drifting downward toward a biochemical plateau, whether OCT reflectance coherence is strengthening, whether autofluorescence noise is settling, whether motion vectors are decelerating toward micro-stillness, or whether perfusion harmonics are converging into a stable flow pattern.

By interpreting these temporal trends rather than single-frame snapshots, AI-Gating determines whether the tissue is moving toward an optimal window for imaging or therapy, or whether it is drifting into a period of instability in which acquisition should be delayed or suppressed. This temporal understanding is central to the architecture of the AI-Gated photomodulation system 202: temporal biomarkers supply the physiologic backbone upon which all predictive inference is built. They allow the AI-Gated photomodulation system 202 to forecast not only when the tissue is ready for high-fidelity imaging or photomodulation, but also when it is likely to become unreceptive, metabolically noisy, or structurally unstable.

Thus, temporal biomarkers transform optical signals from descriptive measurements into predictive indicators. They allow AI-Gating to synchronize photonic activity with the innate physiologic rhythms of the retina and choroid, ensuring that every image, spectral capture, or photomodulation pulse is delivered during the most meaningful and biologically coherent interval.

TABLE 12

Temporal Biomarkers Relevant to Predictive AI-Gating

| Temporal Biomarker | Physiologic Source/Signal Modality | Temporal Behavior | Diagnostic/ Therapeutic Insight | Gating Value for AI-Gating |
|---|---|---|---|---|
| Fixation Stability Intervals | Oculomotor control; microsaccades; eye-tracking/SLO | Transient sub-pixel motion-quiet periods (microseconds-milliseconds) | Enables high-fidelity capture of microstructures; reduces motion distortion | Identifies precise windows for OCT and OCTA frame acquisition |
| Motion Quiescence Bursts | Physiologic tremor, head drift; tracking vectors | Intermittent global stillness across motion channels | Minimizes distortion across all optical modalities | Serves as cross-modal “safe-moment” trigger for synchronized capture |
| Reflectance Coherence Windows | Photoreceptor alignment; outer segment integrity; OCT/NIR/SLO reflectance | Momentary stabilization of reflectance intensity and scatter | Enhances contrast and boundary definition; improves segmentation | Triggers structural imaging during optical clarity intervals |
| Tear-Film Smoothing/ Oscillation | Tear-film dynamics; reflectance/SLO | Cyclic thinning and smoothing over seconds | Sharpens reflectance and reduces scatter-induced noise | Times capture to smooth-phase windows for improved SNR |
| Autofluorescence Stability Moments | Lipofuscin distribution; RPE oxidative load; FAF | Short-lived uniformity between oxidative microbursts | Improves detection of subtle RPE metabolic shifts | Aligns exposure with low-variability FAF intervals for consistent tracking |
| Perfusion Regularity (Choriocapillaris Pulsatility) | Vascular pulsation; microvascular tone; OCTA | Rhythmic peaks of smooth flow tied to heartbeat | Improves visualization of microvasculature; reduces decorrelation artifact | Times acquisition to perfusion-regularity windows for clearer flow maps |
| Flow Regularity Harmonics | OCTA and vascular phase analysis | Harmonic stabilization lasting milliseconds | Improves perfusion mapping consistency | Predicts high-fidelity vascular frames |
| Mitochondrial Quieting Intervals | potential Membrane oscillations; redox cycles; Raman | Periodic metabolic plateaus with reduced spectral noise | Enhances Raman sensitivity to metabolic biomarkers | Predicts optimal Raman acquisition windows with maximal SNR |
| Raman Peak Stability | Raman spectroscopy (biochemical resonances) | Redox-linked oscillations converging to plateau | Improves identification of β-sheet, lipid oxidation, and chromophore ratios | Restricts sampling to biochemical readiness intervals |
| Spectral Plateau Phases/Dynamics | Hyperspectral and mixed chromophore behavior | Moments of spectral convergence across chromophores | Enables classification of subtle biochemical signatures | Improves hyperspectral analysis accuracy by gating to plateau phases |

Table 12 integrates physiologic, optical, and behavioral temporal biomarkers whose short-lived stabilization creates optimal intervals for diagnostic acquisition or therapeutic photonic delivery. The AI-Gating engine 210 detects and forecasts these events to align system activation with periods of maximal diagnostic clarity or metabolic receptivity.

7.0 Detailed Description of the AI-Gating Standalone Embodiment

The AI-Gated photomodulation system 202 includes embodiments in which AI-Gating operates entirely as a standalone capability, independent of multimodal imaging or therapeutic systems. In these configurations, the AI-Gated photomodulation system 202 serves as the sole intelligence layer, predicting the optimal temporal window for photonic activation or diagnostic data acquisition using only a single source of input.

Despite this architectural simplicity, the standalone AI-Gated photomodulation system 202 preserves the core power of predictive gating: it improves signal quality, enhances safety, increases physiologic congruence, and greatly reduces operator-dependent variability. The standalone embodiment therefore represents a compact, deployable, and highly scalable approach to physiologic synchronization.

7.1 AI-Gating Standalone System Architecture

The standalone system architecture is built around the interplay of a single input pathway, an inference engine 224, gating logic 234, and a synchronized photonic or measurement output 232, 236. Even with a minimalistic structure, the AI-Gated photomodulation system 202 exploits the eye's naturally occurring micro-windows of stability. These windows arise despite the presence of constant physiologic disturbance, tear-film collapse, microsaccades, blink transients, accommodative flicker, and metabolic oscillations. In conventional imaging or therapeutic systems, these fluctuations degrade quality or impede precision. In the standalone embodiment, however, the AI-Gated photomodulation system 202 continuously analyzes the temporal behavior of the incoming optical signal and identifies those fleeting intervals in which these disturbances momentarily recede. These intervals become the gating windows through which diagnostic or therapeutic actions are optimally executed.

At the core of this capability is a continuous monitoring stream that captures the eye's optical behavior at high temporal resolution. Reflectance fluctuations, blink-related shape changes, hydration gradients, eyelid trajectories, and subtle positional drifts all appear as structured temporal sequences rather than random noise. Over time, these sequences form recognizable physiologic rhythms, microsaccade-drift cycles, tear-film micro-break patterns, oxidative quieting intervals, metabolic plateaus, choriocapillaris pulsatility flattening, and pre-quiescent fixation deceleration. The standalone embodiment of AI-Gating is designed to detect these rhythms and forecast when the next physiologically favorable interval will arise.

7.2 AI-Gating Single-Sensor Input Layer

In the simplest standalone configuration, the AI-Gated photomodulation system 202 relies on just one sensing modality, which serves as the sole source of physiologic information. This single input may derive from a compact CMOS image sensor, a photodiode array, a near-infrared reflectance diode, a fixation-tracking spot reflector, or any miniature detector capable of producing a continuous optical time-series.

The sensor provides raw, unprocessed temporal data reflecting the micro-instabilities of the eye. Even with only one channel, the signal contains rich physiologic structure. Blink recovery shows as large transient disruptions, tear-film breakup appears as gradual desynchronization of reflectance regularity, fixation drift produces low-frequency positional shifts, and microsaccades generate sharp, rapid peaks.

In the standalone embodiment, no specific imaging modality, such as OCT, OCTA, FAF, or Raman, is required; the AI-Gated photomodulation system 202 performs physiologic prediction using only native reflectance and motion signals, enabling predictive gating in minimal-hardware configurations. The standalone AI-Gated photomodulation system 202 does not require multimodal fusion or complex imaging; the physiologic timing information needed for predictive AI-Gating can be extracted entirely from the single optical stream, making the architecture highly deployable even in small, handheld, or consumer devices.

7.3 AI-Gated System Layer

The AI-Gated System Layer (diagnostic acquisition component 206 and physiologic monitoring subsystem 208) receives the raw temporal data and converts it into a predictive gating score that represents the likelihood that the eye is entering, residing in, or exiting a physiologically stable moment. Because only one data source is available, the AI-Gated System Layer is optimized to interpret temporal patterns rather than spatial features. It identifies microsaccadic oscillations, drift-quiescence transitions, blink-recovery relaxation, reflectance variance dampening, metabolic plateau formation, and perfusion-related micropulsatility flattening.

The AI-Gated photomodulation system 202 may be implemented through temporal convolutional networks, recurrent architectures, lightweight transformers, or even small threshold-trained classifiers depending on device constraints. The training data can be obtained from short optical recordings of normal and abnormal eye behavior, captured under varying conditions. Existing frameworks such as TensorFlow Lite and PyTorch Mobile enable efficient inference on compact processors, ARM cores, microcontrollers, or embedded neural accelerators.

As the AI-Gated photomodulation system 202 operates, the AI-Gated System Layer generates a continuously updated physiologic state vector, capturing tear-film uniformity, fixation behavior, microsaccadic frequency, blink waveform signatures, oxidative or metabolic fluctuations inferred from reflectance harmonics, and the trajectory of each into the near future. With this temporal awareness, the AI-Gated System Layer predicts not merely the present state of stability but the onset of the next quiescent interval, allowing activation to occur proactively rather than reactively.

7.4 AI-Gating Logic Unit

The gating logic 234 translates the output of the Standalone AI-Gated photomodulation system 202 into precise operational control. When the AI-Gated photomodulation system 202 indicates that a high-quality window is approaching or has arrived, the AI-Gated photomodulation system 202 allows the photonic control 232 or actuation layer 236 to activate. When the prediction falls below a stability threshold, activation is withheld or interrupted.

This conversion of continuous physiologic prediction into actionable timing control may be executed through microcontroller firmware, Field Programmable Gate Array (FPGA) logic, or embedded software. The logic is platform-agnostic and can be implemented on low-power hardware, making the standalone embodiment suitable for both clinical and consumer applications.

Importantly, the gating logic 234 does not merely respond to stability; it acts to prevent low-value, distorted, or unsafe activations. As soon as instability is detected, whether due to blink onset, tear-film collapse, abrupt fixation change, or reflectance irregularity, the gate immediately closes, halting output with sub-millisecond latency. This ensures that therapeutic pulses, measurement sampling, or imaging frames occur only during optimal physiologic conditions.

7.5 AI-Gated Output Channel

The output channel (photonic control 232, actuation layer 236) may be configured for photomodulation, diagnostic sampling, or imaging frame capture. Regardless of purpose, the defining principle is that all outputs are temporally synchronized to AI-predicted stability windows. When the single sensor indicates that the eye is entering a moment of structural, metabolic, or reflectance quieting, the output channel activates. When instability returns, the output pauses.

This synchronization dramatically increases the signal-to-noise ratio of the acquired data, enhances the efficiency of photomodulation energy delivery, and reduces the probability of misalignment or biologically ineffective activation. Because the standalone embodiment depends on one sensing pathway and one output pathway, the AI-Gated photomodulation system 202 remains compact, low-cost, and highly reliable.

7.6 AI-Gating Standalone Photomodulation Embodiment

A representative standalone embodiment is a compact photomodulation device incorporating AI-Predictive Gating. Such a device may deliver narrowband light intended to modulate retinal mitochondrial behavior, enhance metabolic efficiency, or support neuro-optical recovery. Photomodulation benefits profoundly from precise physiologic timing, as energy is absorbed far more effectively when the retina is briefly motionless, metabolically quiescent, and structurally coherent.

Even with a single reflectance or positional sensor, the AI-Gated photomodulation system 202 identifies the trajectory of micro-stability. It predicts the moment in which microsaccades slow, reflectance variance drops, and tear-film irregularities temporarily resolve. During this narrow physiologic plateau, the device delivers its photonic pulse. This approach avoids firing energy during periods of motion or instability and allows a simple handheld device to perform at a level traditionally associated with far more complex systems.

7.7 AI-Gating Enablement of Light Delivery Synchronization

Enablement of this embodiment is achieved with minimal engineering overhead. The device may use only a low-power LED array, a simple microcontroller, and the embedded AI-Gated photomodulation system 202. The single sensor provides the temporal data from which the AI-Gated photomodulation system 202 forecasts the optimal delivery window. By suppressing activation during blink recovery, drift acceleration, or reflectance noise, the system reduces wasted pulses and enhances therapeutic efficiency. No multimodal integration is required; the physiologic intelligence alone is sufficient to synchronize light delivery to the most biologically receptive moment.

7.8 AI-Gating Standalone Diagnostic Embodiment

Another AI-Gating standalone embodiment centers on diagnostic acquisition using a single optical sensor. The sensor may record reflectance behavior, positional drift, signal decay patterns, or backscatter characteristics. The AI-Gated photomodulation system 202 interprets the evolving temporal signatures to identify moments in which physiologic noise is minimized and measurement precision is highest.

This embodiment is well-suited to small portable devices or home-monitoring tools where size, cost, and simplicity are crucial. Even without the analytical capacity of OCT, SLO, or Raman systems, the standalone design extracts value by precisely timing when each measurement occurs.

7.9 AI-Gating Enablement of Diagnostic Precision

Diagnostic precision is achieved through the combination of temporal forecasting and artifact suppression. The AI-Gated photomodulation system 202 anticipates periods of drift reduction, reflectance stabilization, and blink-free quiescence. During such intervals, the device captures its diagnostic measurement. When instability is predicted or detected, the AI-Gated photomodulation system 202 delays acquisition until conditions improve.

Standard processing such as temporal smoothing or AI-Guided frame scoring further enhances reliability. These methods are easily implemented with modest hardware and require no specialized imaging subsystems. The diagnostic value arises not from complexity of instrumentation, but from intelligent timing.

8.0 AI-Gating Standalone Safety and Cutoff Embodiment

The standalone AI-Gated photomodulation system 202 can also operate as a safety and cutoff mechanism. Using only one sensor, the AI-Gated photomodulation system 202 can recognize hazardous conditions including excessive motion, blink onset, off-axis alignment, sudden reflectance spikes, or physiologic patterns inconsistent with safe operation. When such patterns are detected or predicted, the AI-Gated photomodulation system 202 immediately suppresses output.

Even simple blink traces, reflectance trajectories, and drift signatures can be used to train the AI-Gated photomodulation system 202. Small datasets suffice, and the architecture scales from clinical systems to home-use consumer devices. This embodiment positions AI-Gating as a guardian that inhibits activation during physiologically unsuitable moments, enhancing safety in compact or minimally supervised environments.

8.1 Advantages of the AI-Gating Standalone Embodiment

Despite its minimalist architecture, the standalone embodiment offers significant advantages. It delivers high diagnostic or therapeutic value solely through temporal optimization. It requires minimal hardware, enabling low-cost manufacturing and broad scalability. Its simplicity eases regulatory pathways and supports integration into handheld and home-use products. By removing operator timing from the workflow, it reduces user dependence and improves consistency. Most importantly, it creates a physiologically synchronized system that ensures optical engagement occurs only when the tissue itself is most prepared to receive it.

Through this combination of predictive modeling, physiologic insight, and compact engineering, the standalone embodiment of the AI-Gated photomodulation system 202 establishes a paradigm in which even the simplest devices gain access to precision.

8.2 Detailed Description of AI-Gating Multimodal Embodiment

The AI-Gated photomodulation system 202 also includes embodiments in which AI-Gating functions as the central predictive intelligence within a multimodal imaging or therapeutic system, coordinating inputs from multiple photonic and physiologic channels. In this integrated configuration, the AI-Gating engine 210 analyzes convergent temporal biomarkers across a plurality of modalities to forecast the optimal biologic moment for activation.

8.3 AI-Gating Multimodal System Architecture

In the multimodal embodiment, AI-Gating extends beyond the constraints of a single-sensor input and serves as the central temporal intelligence within a coordinated imaging and therapeutic platform. Instead of relying on one optical signal, the AI-Gated photomodulation system 202 receives a constellation of physiologic and photonic inputs drawn from modalities such as OCT, OCT angiography, Raman spectroscopy, scanning laser ophthalmoscopy, autofluorescence, hyperspectral imaging, and reflectance-based tracking streams.

By synchronizing each subsystem to intervals of physiologic coherence, the multimodal embodiment substantially elevates image fidelity, spectral clarity, and therapeutic precision while reducing artifacts and energy waste. This integrated form of AI-Gating enhances the performance of all participating modalities.

The multimodal architecture is defined not by hardware complexity alone but by the integration of diverse physiologic rhythms. Tear-film behavior, fixation cycles, vascular micro-pulsatility, oxidative fluctuations, and biochemical oscillations each imprint themselves on different imaging modalities.

The system's predictive engine 228 unifies these diverse temporal signatures into a coherent physiologic narrative, granting it a predictive clarity that surpasses any single-modality analysis. Through this architecture, the AI-Gated photomodulation system 202 identifies the exact temporal corridors in which the eye becomes momentarily stable, receptive, or quiet across multiple physiologic axes.

8.4 Multimodal AI-Gating Input Integration Layer

The multimodal input layer (diagnostic acquisition component 206) brings together a suite of imaging and sensing channels whose signals each carry a fragment of the tissue's temporal behavior. Raman spectroscopy reveals fluctuations in biochemical variance as metabolic signatures pass through noisy and quiet phases. Autofluorescence uncovers oxidative micro-bursts alternating with periods of emission stability. OCT and OCTA detect textural coherence, structural alignment, and vascular pulsatility synchronized to the cardiac cycle. Hyperspectral imaging captures shifts in scattering and absorption patterns as tissue transitions between physiologic states.

Individually, these modalities provide narrow insight; collectively, they reveal the eye's multi-system temporal architecture. Each channel becomes a physiologic witness to different components of retinal and choroidal function. The integration of these inputs enriches the predictive capacity of AI-Gating by enabling it to detect convergence patterns across physiologic systems. When reflectance stabilizes, Raman variance falls, autofluorescence smooths, and OCTA micro-pulsatility flattens, the AI-Gated photomodulation system 202 recognizes these parallel transitions as heralds of a high-value optical moment long before that moment fully emerges.

8.5 Multimodal AI-Gating Model Layer

The AI-Gated photomodulation system 202 in the multimodal embodiment receives diverse temporal inputs and fuses them into a unified predictive framework. It evaluates each physiologic rhythm, whether structural, vascular, metabolic, or optical, not as an isolated phenomenon but as part of an interconnected temporal network. The model identifies early inflection points in these rhythms, such as the deceleration of fixation drift, the progressive smoothing of autofluorescence texture, or the decline in Raman peak variance, and interprets them as trajectories moving toward physiologic coherence.

Through temporal convolutional structures, recurrent architectures, and attention-based predictors, the AI-Gated photomodulation system 202 constructs probabilistic forecasts of when the tissue will enter a state of reduced noise, increased receptivity, or enhanced stability. These forecasts are not merely extrapolations of single-channel behavior but are derived from a multi-modal convergence pattern that reflects deeper physiologic alignment. This multimodal AI-Gated photomodulation system 202 therefore achieves a more comprehensive predictive acuity than the standalone system by recognizing cross-modal harmonization as a key marker of an impending high-value window.

8.6 Multimodal AI-Gating Coordination Unit

The AI-Gated multimodal coordination unit (physiologic monitoring subsystem 208) serves as the orchestrator of all imaging and therapeutic subsystems. Once the AI-Gated photomodulation system 202 identifies that the tissue is moving toward a period of multi-modal physiological stability, the AI-Gating coordinator 208 determines which subsystem is best positioned to exploit that interval. OCT scanning may be triggered at the instant when reflectance coherence aligns with fixation quiescence. Raman acquisition may be initiated when biochemical signatures enter a plateau of spectral stability. OCTA may capture perfusion maps at the precise moment when vascular micro-pulsatility flattens.

In the multimodal configuration, AI-Gating is no longer a simple binary decision but a selective synchronization event that allocates the physiologic window to one or more subsystems based on each modality's temporal requirements. This coordination prevents competing subsystems from interrupting one another and ensures that every activation occurs when the eye's physiology and the device's operational readiness are simultaneously aligned.

8.7 Multimodal AI-Gating Output Execution Layer

The AI-Gating output execution layer (AI-Gating engine 210) translates the AI-Gating coordinator's 208 decisions into precisely timed imaging or therapeutic actions. Each subsystem receives activation permissions only when the predicted physiologic state is optimal for its specific operation. Imaging frames are captured during structural and optical quietness. Spectral data are sampled during biochemical plateaus. Perfusion maps are acquired during diastolic temporal flattening. Photomodulation is delivered when mitochondrial metabolic noise falls into a low-variance trough.

By ensuring that activation occurs only during these physiologically meaningful intervals, the multimodal embodiment elevates the performance of every subsystem without increasing power, hardware complexity, or exposure time. The AI-Gated photomodulation system 202 relies entirely on predictive synchronization rather than forcibly mandated acquisition, producing cleaner images, more interpretable spectra, and safer, more efficient therapeutic pulses.

8.8 Multimodal AI-Gating Photonic and Imaging Embodiment

In the AI-Gating multimodal photonic embodiment, AI-Gating integrates across several imaging and therapeutic pathways to create a unified temporal intelligence. structural OCT, Raman spectroscopy, autofluorescence imaging, hyperspectral analysis, and therapeutic photomodulation that carry their own timing sensitivities and physiologic dependencies. The multimodal AI-Gated photomodulation system 202 identifies the precise intervals in which these modalities converge biologically, allowing the device to use a single physiologic window to support multiple coordinated functions.

During these compound windows, the AI-Gated photomodulation system 202 may initiate OCT scanning at the moment of fixation steadiness, immediately followed by Raman acquisition during biochemical quieting, and then photomodulation during mitochondrial receptivity. The AI-Gated photomodulation system 202 evaluates not only each modality's temporal demands but also its biological context, ensuring that the eye is receptive to each form of optical engagement in sequence.

8.9 AI-Gating Enablement of Multi-Channel Light and Imaging Synchronization

Enablement of the AI-Gating multimodal embodiment is achieved through the temporal modeling of physiologic rhythms across multiple channels. Because the foundational predictive logic may remain identical to the standalone embodiment, the AI-Gated photomodulation system 202 does not require specialized multimodal hardware to function. Rather, each additional channel simply broadens the temporal features available to the AI-Gated photomodulation system 202.

The AI-Gated photomodulation system 202 recognizes Raman spectral trajectories, OCT reflectance coherence, autofluorescence smoothing, OCTA micro-pulsatility flattening, hyperspectral noise reduction, and fixation drift deceleration as manifestations of deeper physiologic processes becoming synchronized. When these multi-channel indicators align, the AI-Gated photomodulation system 202 anticipates an imminent high-value interval and authorizes activation. Thus, the multimodal embodiment builds upon the same core principles of physiologic forecasting while expanding the richness of the temporal biomarkers used to identify optimal engagement.

9.0 Multimodal AI-Gating Diagnostic Embodiment

The multimodal diagnostic embodiment utilizes the AI-Gated photomodulation system 202 to elevate the quality of imaging across structural, vascular, spectral, and biochemical domains. Each imaging modality thrives when physiologic noise is minimized. By capturing data only during physiologically coherent intervals, the multimodal embodiment produces sharper structural OCT images, clearer Raman spectra, more reliable OCTA flow maps, and more interpretable autofluorescence patterns.

This diagnostic synchronization does not depend on mechanical stabilization but instead uses the eye's own rhythmic quieting as the anchor for high-value acquisition. The AI-Gated photomodulation system 202 adapts dynamically to each patient's unique physiologic signature, recognizing individual variations in tear-film dynamics, vascular oscillation patterns, metabolic cycles, and fixation behavior.

9.1 Enablement of AI-Gated Multimodal Diagnostic Precision

Multimodal precision is enabled by fusing temporal trajectories across several physiologic systems. Each modality contributes a portion of the predictive picture: Raman variance trajectories reveal biochemical readiness, OCT reflectance coherence reflects structural stability, autofluorescence smoothing signifies oxidative quieting, and OCTA pulsatility flattening indicates vascular steadiness. When these trajectories converge, the AI-Gated photomodulation system 202 initiates diagnostic capture with millisecond precision.

9.2 Multimodal AI-Gated Safety and Inhibition Embodiment

The multimodal embodiment also enhances safety by predicting physiologic states that would render imaging or therapy unreliable or hazardous. Blink onset, drift acceleration, metabolic turbulence, vascular surges, and spectral noise spikes all manifest distinctly across the multimodal channels. By interpreting these patterns collectively, the AI-Gated photomodulation system 202 detects unsafe conditions earlier and more reliably than any single modality could achieve.

Output is inhibited instantly when predictions indicate that the physiologic state is unsuitable. This ensures that lasers are not fired during motion, Raman spectra are not captured during metabolic turbulence, OCT scans are not drawn across fixation breaks, and autofluorescence imaging is not attempted during oxidative bursts. The multimodal AI-Gated photomodulation system 202, therefore, acts not only as an optimizer of high-value acquisition but as a guardian against biologically incongruent engagement.

9.3 Advantages of the Multimodal AI-Gating Embodiment

The multimodal embodiment of AI-Gating creates a physiologically synchronized ecosystem in which every imaging and therapeutic subsystem benefits from predictive timing. Structural imaging becomes sharper, spectral measurements become cleaner, perfusion maps become more reliable, and photomodulation becomes more biologically efficient. This embodiment introduces a new paradigm in which photonic technology interacts with the eye only during moments of natural physiologic harmony.

In this context, AI-Gating serves as a temporal bridge between biology and technology, anticipating rather than reacting, adapting rather than assuming, synchronizing rather than approximating. The result is a predictive, physiologically tuned multimodal AI-Gated photomodulation system 202 that fundamentally redefines how and when light interacts with living tissue.

TABLE 13

Comparison between Standalone and Multimodal AI-Gated Systems

| Feature | Standalone AI-Gated System | Multimodal AI-Gated System |
|---|---|---|
| Core Concept | Independent device performing AI-Gating using only its native sensors | Integrated platform combining multiple imaging/sensing modalities under unified AI-Gating |
| Input Sources | Native reflectance sensors, NIR diodes, autofluorescence channels, motion detectors | OCT, OCTA, FAF, Raman, hyperspectral, SLO, NIR reflectance, plus native sensors |
| AI-Gating Engine | Identical algorithmic core, but operates with fewer input classes | Same AI-Gating engine, enhanced by richer multimodal inputs |
| Physiologic Biomarker Set | Reflectance oscillations, scattering, basic metabolic fluorescence, motion quieting | Structural coherence, perfusion regularity, RPE metabolic transitions, biochemical plateau states, spectral signatures |

TABLE 13-continued

Comparison between Standalone and Multimodal AI-Gated Systems

| Feature | Standalone AI-Gated System | Multimodal AI-Gated System |
|---|---|---|
| Predictive Accuracy | Sufficient for physiologic gating; optimized for low-resource or portable contexts | Highest predictive accuracy due to cross-modal fusion and physiologic corroboration |
| Clinical Use Cases | PBM timing, basic diagnostic gating, home-use systems, low-cost or remote settings | High-precision retinal imaging, early AMD detection, toxic maculopathy screening, multimodal synchrony |
| Advantages | Portable, inexpensive, fully enabled without advanced imaging | Synergistic physiologic integration, cross-modal temporal precision |
| Hardware Complexity | Minimal hardware; does not require OCT/FAF/Raman | Uses existing modalities but adds a new predictive supervisory layer |
| Scope of AI-Gated Photomodulation | Photomodulation gated based on reflectance + motion | Photomodulation gated based on comprehensive metabolic, structural, vascular, and biochemical biomarkers |
| Overall Impact | Physiologically timed PBM and imaging independent of modality | Highest fidelity diagnostic and therapeutic synchronization available |

9.4 Benefits of Predictive Timing Compared to Real-Time Feedback

The predictive AI-Gating forecasts physiologic transitions before they occur, enabling the AI-Gated photomodulation system 202 to act proactively rather than reactively. This predictive capability fundamentally enhances both diagnostic quality and therapeutic precision.

By modeling the trajectory of temporal biomarkers, such as reflectance coherence trends, Raman spectral variance, autofluorescence granularity, fixation dynamics, and perfusion micro-pulsatility, the AI-Gated photomodulation system 202 is able to anticipate moments of impending instability.

When subtle inflection points indicate that the tissue will soon enter a period of motion, metabolic turbulence, oxidative fluctuation, or vascular irregularity, AI-Gating can terminate or delay acquisition before degradation occurs. The result is a capture sequence that is more physiologically aligned and less contaminated by transient instability.

Prediction also enables anticipatory synchronization across optical modalities. Because the AI-Gated photomodulation system 202 can forecast a future moment when the tissue will reach a high-value state, it can coordinate imaging and emission events such that OCT frames, Raman spectra, autofluorescence captures, and photomodulation pulses all occur during the same predicted interval of physiologic coherence. This multimodal temporal alignment substantially increases diagnostic confidence, enabling clinicians to compare structural, biochemical, metabolic, and perfusion signatures that were acquired under identical physiologic conditions rather than at unrelated time points.

A further benefit of predictive timing is increased reproducibility. The biologic rhythms that generate stability can vary widely across sessions or days. Predictive AI-Gating learn the characteristic oscillatory patterns of each tissue and forecasts the next forthcoming window of stability, ensuring that acquisitions across different sessions are temporally comparable. This directly improves longitudinal monitoring, disease staging, and treatment response assessment.

Therapeutic optimization also emerges from predictive reasoning. Photomodulation is delivered only when the tissue is forecasted to be metabolically receptive, such as during mitochondrial quieting, spectral plateau phases, or oxidative steadiness, ensuring that photons interact with tissue when they are most likely to generate a beneficial cellular response. By avoiding emission during predicted periods of metabolic instability, the AI-Gated photomodulation system 202 reduces unnecessary exposure and enhances both safety and therapeutic efficiency.

Predictive AI-Gating additionally improves early disease detection. Subtle biomarkers, such as weak Raman peaks associated with drusen amyloid, early oxidative fluctuations visible on FAF, or low-contrast perfusion signatures on OCTA, often become detectable only during brief low-noise windows. By forecasting and targeting these windows rather than waiting for them to occur spontaneously, the AI-Gated photomodulation system 202 reveals subtle pathologic features that might otherwise remain obscured.

In all of these ways, predictive AI-Gating advances optical diagnostics and therapy beyond the constraints of real-time gating, establishing a precision framework in which imaging and photonic emission occur at physiologically strategic moments.

9.5 Performance of the AI-Gating System with Other Optical Modalities

The disclosed AI-Gating architecture functions as a unifying temporal intelligence layer that governs how and when optical systems interact with living tissue. Although optical coherence tomography, OCT angiography, fundus reflectance, autofluorescence imaging, scanning laser ophthalmoscopy, Raman spectroscopy, hyperspectral imaging, and photomodulation each provide unique and highly specialized forms of information, all of them are constrained by the same fundamental truth: ocular physiology is dynamic. Tissue reflectance, biochemical signatures, perfusion behavior, mitochondrial readiness, fluorescence emission, and fixation stability fluctuate from moment to moment in ways that directly influence imaging quality and therapeutic precision.

AI-Gating uses a biologically synchronized timing model. The AI-Gated photomodulation system 202 continuously analyzes incoming optical or physiologic signals, whether from a single device or an array of integrated modalities, and forecasts when the tissue will enter a state of maximum optical coherence, spectral stability, metabolic quieting, or perfusion regularity. Imaging or photomodulation is then triggered precisely at these predicted intervals, transforming the interaction between device and tissue into a cooperative process governed by physiologic readiness.

In standalone configurations, AI-Gating can be applied to commercial OCT or OCTA systems without altering their hardware. The gating layer simply receives temporal optical data, forecasts high-value acquisition windows, and instructs the device when to capture. In integrated embodiments, AI-Gating orchestrates the timing of multiple modalities simultaneously. For example, OCT may be triggered during predicted motion-free intervals, OCTA during predicted perfusion stability, Raman during predicted biochemical plateaus, and photomodulation during predicted mitochondrial receptivity. Because all operations share a common temporal reference, the resulting datasets are intrinsically aligned, more interpretable, and vastly more reproducible.

The value of this integration becomes especially significant during longitudinal follow-up. When each modality acquires data during physiologically comparable moments, trends in retinal structure, perfusion, biochemistry, and metabolic state can be compared reliably across sessions. This temporal harmonization strengthens biomarker interpretation, enhances early disease detection, and allows therapeutic responses to be evaluated with far greater confidence.

The following section illustrates how AI-Gating elevates each optical modality by aligning its activity with the retina's own physiologic rhythms. Whether applied in a minimal single-modality deployment or in a fully integrated multimodal platform, AI-Gating provides a predictive, physiologically optimized timing framework that significantly improves diagnostic accuracy, spectral clarity, perfusion mapping, and therapeutic precision across the entire optical ecosystem.

TABLE 14

Comparative Overview of AI-Gating Integration with Variety of Optical Modalities

| Modality | Primary Diagnostic/ Therapeutic Output | Key Physiologic Limitation (Without Gating) | How AI-Gating Enhances Performance | Standalone Compatibility | Integrated Compatibility |
|---|---|---|---|---|---|
| Optical Coherence Tomography (OCT) | Structural imaging of retinal layers, drusen, EZ integrity | Motion artifacts, reflectance instability, fixation drift | Captures during predicted motion-quiescence and reflectance coherence windows, improving segmentation fidelity and layer definition | Yes | Yes |
| OCT Angiography (OCTA) | Perfusion maps of retinal and choroidal vasculature | noise, Pulsatility decorrelation variability, flow instability | Triggers during predicted perfusion stability phases, yielding clearer capillary networks and fewer flow void artifacts | Yes | Yes |
| Fundus Reflectance (Visible/NIR) | Photoreceptor and RPE reflectance patterns | Tear-film instability, scatter fluctuations, micro-movement | Synchronizes capture to predicted optical stability, enhancing image contrast and RPE/photreceptor visualization | Yes | Yes |
| Fundus Autofluorescence (FAF) | Lipofuscin and bisretinoid metabolic assessment | Oxidative bursts, excitation-history variability | Identifies low-variability FAF intervals, improving metabolic signal interpretation | Yes | Yes |
| Scanning Laser Ophthalmoscopy (SLO) | Confocal reflectance and fixation analysis | Tremor and microsaccades degrade raster reliability | Gated to predicted fixation stability intervals for improved clarity and microstructure detail | Yes | Yes |
| Raman Spectroscopy | Biochemical signatures of lipids, amyloid, redox state | High sensitivity to metabolic noise and motion | Predicts biochemical plateau states for high-SNR spectral acquisition | Yes | Yes |

TABLE 14-continued

Comparative Overview of AI-Gating Integration with Variety of Optical Modalities

| Modality | Primary Diagnostic/ Therapeutic Output | Key Physiologic Limitation (Without Gating) | How AI-Gating Enhances Performance | Standalone Compatibility | Integrated Compatibility |
|---|---|---|---|---|---|
| Hyperspectral Imaging | Molecular absorption/scattering across wavelengths | Spectral drift, chromophore instability | Activates during predicted spectral plateau phases, improving chromophore discrimination | Yes | Yes |
| Photomodulation (Light Therapy) | Mitochondrial, RPE, and choroidal metabolic modulation | Delivered during metabolically unstable or unreceptive intervals | Restricts exposure to predicted metabolic receptivity windows, enhancing safety and therapeutic effectiveness | Yes | Yes |
| AI-Gating (Standalone Software) | Predictive temporal control | None intrinsically-relies on device data streams | Serves as a universal controller for timing across any modality | Yes | Yes |

9.6 AI-Gating and Multimodal Predictive Fusion

The AI-Gated photomodulation system 202 enables a level of multimodal coordination that has not been possible with conventional ophthalmic imaging platforms. In standard clinical workflows, each modality, OCT, OCTA, Raman spectroscopy, fundus autofluorescence, reflectance imaging, and hyperspectral systems, captures data independently, at arbitrary moments determined by operator timing or device presets.

Because each modality is sensitive to moment-to-moment physiologic fluctuations, its images or spectra rarely represent the same underlying physiologic state. As a result, cross-modal interpretation is often degraded by temporal mismatch: structural clarity may not coincide with perfusion regularity, Raman biochemical signatures may not align with oxidative stress markers, and autofluorescence fluctuations may obscure subtle spectral features.

AI-Gating fundamentally transforms this paradigm by providing a predictive temporal framework capable of synchronizing multiple modalities to act during the same biologically optimal interval. Rather than functioning in isolation, two or more instruments may be triggered simultaneously, or in tightly coordinated sequence, based on the AI engine's forecast of when the tissue will enter a transient window of stability, metabolic quieting, or spectral coherence.

For example, OCT and Raman spectroscopy may be activated together during a predicted interval of reduced motion and biochemical stabilization; OCTA and FAF may be paired during a phase of vascular smoothness and uniform autofluorescence; or reflectance and hyperspectral acquisition may be aligned with predicted moments of high scattering coherence.

To operationalize this multimodal synchrony, the AI-Gated photomodulation system 202 maintains a unified temporal index that is continuously updated as the predictive engine 228 analyzes incoming biomarker trajectories. When the AI-Gated photomodulation system 202 forecasts an upcoming interval of physiologic coherence, defined by converging trends in reflectance stability, Raman variance, perfusion regularity, or motion quiescence, the AI-Gated photomodulation system 202 computes a gating confidence score.

Once this score crosses a predefined threshold, the controller issues synchronized trigger commands to each modality in the fusion set. These commands are timestamped and aligned to the same predicted physiologic phase, ensuring that OCT structural volumes, OCTA flow maps, Raman spectral captures, FAF images, and reflectance frames are acquired during the identical moment of optical and metabolic readiness. This shared temporal alignment enables direct cross-modal comparison of structural, vascular, metabolic, and biochemical information that originates from the same physiologic state rather than from unrelated or unstable intervals.

The benefits of multimodal predictive fusion are substantial. Diagnostic coherence improves because each dataset reflects the same underlying physiology, eliminating much of the noise and variability that arise from asynchronous or technician-timed acquisition. Cross-modal interpretation becomes more powerful: Raman spectral signatures can be directly mapped onto OCT-detected drusen structures; perfusion irregularities detected on OCTA can be correlated with local autofluorescence behavior; and reflectance changes can be linked to biochemical shifts measured through Raman or hyperspectral imaging.

Early detection of subtle pathology, such as microstructural deformation, emerging oxidative stress patterns, or biochemical markers of drusen maturation, is significantly enhanced when modalities agree temporally. The predictive fusion framework also strengthens longitudinal monitoring by ensuring that every multimodal dataset collected across visits represents comparable physiologic conditions.

By enabling synchronized operation across independent optical and spectroscopic platforms, AI-Gating introduces a multimodal architecture that elevates every modality's diagnostic value. The AI-Gated photomodulation system 202 transforms these instruments from isolated, sequential tools into a harmonized network capable of capturing a unified physiologic snapshot, one that reflects structural, biochemical, vascular, and metabolic states with unprecedented temporal fidelity. This capability provides a powerful new foundation for early disease detection, risk stratification, treatment monitoring, and mechanistic insight across a broad spectrum of ophthalmic and systemic disorders.

9.7 Summary of Multimodal Integration and System Novelty

Taken together, the disclosed architecture establishes a unified framework in which structural, biochemical, vascular, reflectance, and fluorescence-based modalities no longer operate as independent or asynchronous systems. Instead, each modality becomes part of a coordinated, predictive ecosystem in which optical interrogation and photonic delivery occur only during physiologically favorable intervals identified by the AI-Gating engine 210.

This transforms OCT from a static structural recorder into a physiologically synchronized structural probe, Raman spectroscopy from a noise-sensitive acquisition into a timing-dependent biochemical clarity detector, OCT angiography from a flow snapshot into a tool for precision perfusion assessment, and fundus autofluorescence from a variable metabolic indicator into a signal captured at the moment of maximal stability. In therapeutic applications, photomodulation shifts from a fixed illumination schedule to a biologically negotiated intervention delivered only when the tissue is most receptive.

The following section illustrates how this architecture translates into clinical impact across multiple disease states, demonstrating how predictive physiologic synchronization enhances diagnostic sensitivity, treatment precision, and the early detection of pathologic change.

9.8 Clinical Applications and Disease-Specific Embodiments

The clinical power of the AI-Gated photomodulation system 202 arises from its ability to interpret physiology as a continuous, time-dependent process rather than as a collection of static optical snapshots. Virtually all diseases, ocular or systemic, exhibit fluctuations in tissue structure, metabolic behavior, vascular stability, and biochemical activity. These fluctuations govern when meaningful diagnostic information emerges and when photonic interventions are most likely to be effective.

AI-Gating transforms this paradigm by synchronizing every diagnostic or therapeutic action to windows of predicted physiologic stability. By continuously monitoring temporal biomarkers, reflectance coherence, mitochondrial spectral quieting, perfusion regularity, fixation stability, and numerous others, the AI-Gated photomodulation system 202 identifies when the tissue is most structurally coherent, most metabolically receptive, and most optically informative. These windows may last only milliseconds, yet they represent the moments in which imaging yields maximal fidelity and photomodulation produces maximal biologic effect.

This capability makes the AI-Gated photomodulation system 202 inherently adaptable across diseases. Whether the target is drusen composition in age-related macular degeneration, flow instability in glaucoma, inflammatory flare in uveitis, or biochemical signatures of early retinal degeneration, the same predictive principles apply: the tissue cycles through high-value and low-value physiologic states, and the AI-Gating engine 210 ensures that acquisition occurs only within the former. The result is enhanced sensitivity to early pathologic change, improved classification of disease severity, and far more reliable longitudinal monitoring.

Although the AI-Gated photomodulation system 202 is fundamentally generalizable to any organ system accessible to optical interrogation, the retina and macula serve as an ideal demonstration platform because they exhibit rapid physiologic cycling, rich multimodal optical signatures, and clinically meaningful fluctuations on the scale of seconds. The embodiments that follow illustrate how predictive physiologic synchronization elevates diagnostic accuracy, reduces inter-session variability, and reveals clinically actionable trends that remain hidden within ungated imaging.

In this context, AI-Gating functions not merely as a timing mechanism but as a physiologic interpreter, linking real-time biology to real-time photonic action. It ensures that each retinal image, spectral measurement, or therapeutic pulse is delivered when the tissue is most revealing and most responsive. The disease-specific embodiments in this section demonstrate how this capability transforms ophthalmic diagnostics and therapy across a wide spectrum of retinal and systemic conditions.

9.9 AI-Gating in Age-Related Macular Degeneration (AMD)

Age-related macular degeneration represents an ideal clinical setting for the AI-Gated photomodulation system 202 because the disease evolves through continuous structural, biochemical, metabolic, and perfusion-related fluctuations that are not adequately captured by static or arbitrarily timed imaging.

In conventional ophthalmic workflows, OCT, autofluorescence, Raman spectroscopy, and vascular imaging are acquired under the assumption that the macula is physiologically stable at the moment of capture. In reality, the retinal environment changes over milliseconds to minutes, reflectance coherence varies with photoreceptor alignment, Raman spectral clarity shifts with mitochondrial redox state, autofluorescence fluctuates with oxidative load, and choriocapillaris flow regularity oscillates with micro-pulsatility. These transient behaviors mean that many disease-defining biomarkers are temporally unstable and may be missed entirely when acquisition is ungated.

The disclosed AI-Gating architecture introduces predictive physiologic synchronization, allowing imaging and therapeutic activity to occur only during short-lived intervals in which structural reflectance, biochemical spectral stability, perfusion regularity, or autofluorescence uniformity are maximized. By forecasting these intervals rather than reacting to static measurements, the AI-Gated photomodulation system 202 increases diagnostic sensitivity, improves longitudinal reproducibility, and enables earlier detection of subtle physiologic deterioration that can precede clinical conversion to advanced disease.

AI-Gating may function as a standalone analytical platform or be selectively combined with one or more optical modalities. The AI-Gated photomodulation system 202 does not depend on a particular hardware configuration and can operate independently of OCT, Raman, FAF, OCTA, or future imaging systems. When integrated into multimodal acquisition, AI-Gating synchronizes structural, metabolic, vascular, and biochemical capture within the same predicted physiologic window, generating coherent datasets that are not attainable with open-loop systems.

This capability is particularly impactful in AMD, where biomarkers such as drusen composition, RPE metabolic stress, autofluorescence texture, choriocapillaris flow irregularity, and mitochondrial dysfunction express differently across time. By timing acquisition to predicted periods of physiologic coherence, the AI-Gated photomodulation system 202 enhances early detection, supports more reliable monitoring, and provides a fundamentally improved framework for disease surveillance and therapeutic decision-making.

10.0 Evaluation of AMD with AI-Gating and Multimodal Embodiments

Age-related macular degeneration is a condition defined not by a single biomarker, but by the interplay of structural change, vascular instability, biochemical accumulation, and metabolic stress. The AI-Gated photomodulation system 202 is uniquely suited to this complexity because it can operate with any single modality or selectively combine multiple modalities within the same physiologic window. Whether functioning as a standalone predictive engine or as an integrated multimodal system, AI-Gating improves the diagnostic yield of each technology by ensuring that imaging and spectral acquisition occurs only during intervals of retinal stability, metabolic quieting, or perfusion regularity.

In structural applications, optical coherence tomography (OCT) benefits from predictive timing because reflectance coherence and motion quiescence are not constant throughout an examination. During brief, forecasted intervals, the photoreceptor outer segments align more consistently, and scattering pathways stabilize, sharpening layer boundaries and revealing subtle features that may otherwise be missed.

Under these conditions, the AI-Gated photomodulation system 202 becomes more sensitive to early ellipsoid-zone attenuation, micro-disruption of photoreceptor architecture, shallow subretinal drusenoid deposits, parafoveal hyperreflective foci, and evolving changes in drusen height or internal reflectivity. By synchronizing acquisition to these physiologic windows, AI-Gated OCT transforms structural imaging from a snapshot into a more precise indicator of early AMD-related injury.

Vascular assessment through OCT angiography is similarly enhanced. Choriocapillaris perfusion is highly dynamic, exhibiting rhythmic fluctuations that can obscure or exaggerate pathology when sampled at arbitrary times. AI-Gating identifies the moments in which flow irregularity stabilizes, enabling clearer visualization of choriocapillaris flow voids, parafoveal perfusion dropout, nascent ischemic changes, and early neovascular precursor patterns. As a result, OCTA becomes more reliable for detecting both progression and subtle microvascular vulnerability long before clinically visible conversion.

Biochemical interrogation through Raman spectroscopy provides an entirely different dimension of AMD evaluation, capturing molecular signatures rather than structural or vascular patterns. Relevant biomarkers include amyloid β-sheet signals, oxidized lipids, bisretinoids such as A2E and A2F, photoreceptor redox state, and lipid-to-protein ratios within drusen.

These signatures are notoriously sensitive to metabolic noise and therefore benefit profoundly from gated timing. AI-Gating forecasts short intervals of biochemical quieting in which spectral variance decreases and vibrational interference subsides, generating reproducible and high-signal-to-noise spectra. This enables the detection of biochemical changes that may precede structural transformation, offering earlier insight into disease trajectory and risk.

Metabolic embodiments, including fundus autofluorescence and hyperspectral imaging, track physiologic stress rather than anatomy or perfusion. Lipofuscin distribution, oxidative load, mitochondrial strain, and oxygenation gradients fluctuate rapidly and are often uninterpretable when captured during periods of instability. Predictive gating allows these modalities to acquire data only during moments when autofluorescence texture becomes uniform or when hyperspectral signals enter characteristic plateau phases. Under these conditions, subtle shifts in oxidative metabolism and mitochondrial compromise become measurable, improving the ability to monitor early AMD and evaluate response to therapy.

Across all embodiments, the rationale remains consistent: AI-Gating aligns each modality with the physiologic state that maximizes its interpretive value. The AI-Gated photomodulation system 202 may function with a single modality, providing standalone predictive stabilization, or combine multiple modalities within the same predicted interval to generate synchronized structural, vascular, biochemical, and metabolic data from the identical physiologic moment. This multimodal predictive fusion is not available in conventional ophthalmic systems and provides a uniquely powerful framework for diagnosing and monitoring AMD with greater sensitivity, reproducibility, and temporal precision.

10.1 Drusen-Focused Embodiments and Biomarker Assessment Using AI-Gating

Drusen are not static deposits but biologically active, temporally evolving structures whose composition and optical behavior reflect the underlying metabolic and inflammatory state of the macula. Their internal architecture includes variable proportions of lipids, phospholipids, cholesterol esters, bisretinoids, complement proteins, and amyloid-beta species; these components fluctuate across weeks to months as the disease advances. Conventional imaging captures drusen only as fixed morphologic elevations, masking the biochemical and temporal complexity that determines progression risk.

The AI-Gated photomodulation system 202 enables both standalone and multimodal evaluation of drusen by synchronizing acquisition to physiologic windows in which structural, biochemical, and metabolic signals become momentarily coherent. When operated with structural OCT alone, AI-Gating identifies intervals in which reflectance coherence and fixation stability converge, sharpening the delineation of drusen height, internal reflectivity, hyporeflective cores, and early subretinal drusenoid deposits. These synchronized captures improve sensitivity to internal heterogeneity, an increasingly recognized marker of drusen instability and impending atrophy.

When Raman spectroscopy is used as an adjunct, AI-Gating forecasts short periods of biochemical quieting in which spectral variance diminishes and vibrational noise stabilizes. During these gated intervals, the AI-Gated photomodulation system 202 can more reliably detect amyloid β-sheet signatures, oxidized lipid peaks, bisretinoid fingerprints (A2E/A2F), and lipid-to-protein structural ratios that correlate with inflammatory activation and complement-mediated injury. These measurements would be unreliable if acquired during ungated periods of metabolic fluctuation.

Fundus autofluorescence and hyperspectral imaging further expand the biochemical and metabolic profile of drusen. AI-Gated timing allows acquisition only during transient plateaus of autofluorescence uniformity or spectral stabilization, revealing fluctuations in lipofuscin burden, oxidative load, and mitochondrial stress that would otherwise be obscured by physiologic noise. Because these modalities assess the same lesion through different optical dimensions, the selective synchronization made possible by AI-Gating enables a layered understanding of drusen biology in vivo, capturing structural integrity, biochemical composition, and metabolic stress within the same physiologic state.

Whether deployed as a single-modality stabilizing technology or as a platform for predictive multimodal fusion, AI-Gating transforms drusen assessment from a static morphologic observation into a dynamic physiologic analysis. This capability supports earlier detection of destabilizing change, improves longitudinal comparability, and provides a scientifically grounded foundation for identifying eyes at risk of progression.

10.2 AI-Gated Control of Photomodulation and Therapeutic Exposure

Photomodulation refers to the controlled delivery of low-energy photonic stimulation intended to influence cellular metabolism, enhance mitochondrial performance, modulate oxidative stress, or promote structural recovery in ocular tissues. Unlike ablative or thermal laser exposures, photomodulation operates within a biologically permissive energy range where photons act as metabolic cues rather than destructive stimuli.

Within the retina and adjacent tissues, photomodulation engages pathways related to cytochrome-c oxidase activation, mitochondrial membrane potential stabilization, ATP generation, and downstream antioxidative mechanisms. These effects support photoreceptor resilience, RPE metabolic balance, choriocapillaris function, and recovery of tissues under oxidative or inflammatory burden.

Although the therapeutic potential of photomodulation is well recognized, its efficacy is heavily dependent on the physiologic state of the target tissue at the moment the light is delivered. Mitochondria display oscillatory fluctuations in membrane potential and redox readiness; RPE autofluorescence and oxidative load shift over short intervals; choriocapillaris perfusion varies across the cardiac cycle; and retinal motion or fixation instability can degrade the uniformity of the exposure.

AI-Gating introduces a new level of therapeutic control by continuously monitoring optical or physiologic feedback from the target tissue. Signals derived from reflectance stability, mitochondrial spectral signatures, autofluorescence characteristics, and vascular pulsatility are analyzed in real time to identify moments in which the tissue exhibits metabolic receptivity and structural stability. During these ideal intervals, whether measured in milliseconds or seconds, the AI-Gating engine 210 issues a permissive command allowing photomodulation to proceed. Conversely, during periods of motion, metabolic instability, perfusion instability, or metabolic noise, the system suppresses photonic output.

In this manner, AI-Gated photomodulation transforms therapeutic exposure from a static, technician-timed event into a biologically synchronized intervention. Light is delivered only when it is most likely to propagate efficiently through the tissue, to be absorbed predictably by cytochrome-c oxidase or other chromophores, and to elicit the intended downstream mitochondrial or cellular response.

The AI-Gated photomodulation system 202 therefore elevates photomodulation from a general therapeutic technique into a precision-timed, physiologically integrated therapy, offering improved safety, reduced cumulative exposure, and enhanced clinical effectiveness. This biologically aware method of delivery forms the conceptual bridge to the subsequent description of open-loop limitations, closed-loop feedback architecture, and predictive timing control within the broader AI-Gated photomodulation system 202.

10.3 AI-Gated Biomarker-Based Diagnosis and Monitoring of AMD

The diagnostic value of AI-Gating arises from its ability to identify when optical biomarkers of AMD are most detectable. Structural features such as ellipsoid-zone attenuation, outer-segment disruption, early subretinal drusenoid deposits, hyperreflective foci, and changes in drusen contour sharpen predictably during intervals of reflectance coherence. By synchronizing OCT acquisition to these periods, the AI-Gated photomodulation system 202 improves sensitivity to early disease and enhances the reliability of progression assessment across visits. Vascular instability in intermediate and advanced AMD often manifests as transient choriocapillaris flow voids, parafoveal dropout, or nascent neovascular precursor patterns that may be obscured during motion or micro-pulsatility. AI-Gated OCT angiography captures flow during intervals of predicted perfusion regularity, allowing earlier detection of subclinical non-exudative macular neovascularization that would otherwise remain undetected. Biochemical analysis of AMD is frequently limited by spectral noise, tear-film variability, and metabolic fluctuation. Raman spectroscopy performed without temporal control produces inconsistent signatures of amyloid, oxidized lipid species, bisretinoids, and redox-state markers. AI-Gating identifies short-lived biochemical quieting in which spectral variance decreases and Raman plateaus emerge, enabling stable acquisition of lipid-protein ratios and drusen-associated biochemical fingerprints.

Metabolic biomarkers detected through autofluorescence or hyperspectral imaging, including lipofuscin texture, oxidative load, mitochondrial stress, and local oxygenation gradients, stabilize only intermittently. When these signals are captured during predicted intervals of fluorescence uniformity or spectral convergence, the resulting images provide a clearer representation of metabolic stress and allow reproducible longitudinal tracking of geographic atrophy expansion, parafoveal metabolic decline, and early foveal vulnerability. Through physiologic synchronization rather than increased illumination or sampling density, the AI-Gated photomodulation system 202 transforms each modality into a higher-fidelity diagnostic tool and yields a more accurate representation of disease activity over time.

TABLE 15

Temporal Biomarkers Indicative of High-Risk AMD Progression

| Temporal Biomarker | Characteristic Temporal Change | Typical Time Window Before Exudation | Primary Detection Modality (AI-Gated) | Predictive Significance |
|---|---|---|---|---|
| Rapid drusen collapse or regression | Previously stable large soft drusen shrink, flatten, or disappear over weeks; often preceded by increased | 4-12 weeks (range 3-6 months) | SD-OCT, FAF (AI-Gated timing improves clarity during | Strong indicator of impending RPE breach and inflammation; among the most |

TABLE 15-continued

Temporal Biomarkers Indicative of High-Risk AMD Progression

| Temporal Biomarker | Characteristic Temporal Change | Typical Time Window Before Exudation | Primary Detection Modality (AI-Gated) | Predictive Significance |
|---|---|---|---|---|
| | reflectance instability and rising FAF signal | | reflectance coherence intervals) | validated conversion predictors |
| Emergence or rapid expansion of subretinal drusenoid deposits (SDD/reticular pseudodrusen) | New SDD appear or existing lesions increase in depth or number; associated with oligomeric Aβ accumulation | 3-9 months before type 3 MNV | OCT (en-face + B-scan), NIR reflectance | Single strongest predictor of progression to type 3 MNV; correlates with mitochondrial dysfunction and hypoxia |
| Development of hyporeflective cores or "splitting" within drusen | Drusen develop central cavities or layered separation, indicating internal liquefaction and inflammatory remodeling | 4-20 weeks | High-resolution OCT (UHR-OCT, AO-OCT), NIR | Highly specific sign of drusen destabilization and imminent sub-RPE invasion |
| New or migrating intraretinal hyperreflective foci (HRF) | HRF appear or shift inward over 1-3 months; may increase in number or cluster | 1-4 months | OCT (AI-Gated acquisition improves detection during motion-quiet intervals) | Reflects inflammatory cell migration and photoreceptor stress; associated with 2-3× increased conversion risk |
| Appearance of vitelliform-like subretinal deposits | Rapid development of hyperautofluorescent material between RPE and photoreceptors, often rich in Aβ42 | 2-12 weeks | FAF + OCT | Frequently precedes aggressive conversion; may justify accelerated monitoring or prophylactic intervention |
| Sudden increase in OCTA flow irregularity or non-exudative MNV signals | Perfusion instability emerges before fluid; early type 1 neovascular networks detectable only during perfusion-stable intervals | 6-24 weeks before leakage | OCTA (AI-Gated enhances visualization during micro-pulsatility convergence) | Represents subclinical CNV; strongest actionable pre-fluid biomarker |
| Acceleration of ellipsoid-zone (EZ) attenuation adjacent to drusen | Localized EZ thinning progresses rapidly despite stable drusen volume | 2-6 months | OCT | Marker of photoreceptor compromise and oxidative stress; predicts rapid functional decline |
| Increased autofluorescence heterogeneity surrounding drusen | FAF texture becomes irregular or mottled over short intervals | 3-12 months | FAF (AI-Gated reduces oxidative-noise variability) | Indicates heightened lipofuscin load and RPE stress; spatially predictive of atrophy expansion |
| Choroidal vascular index (CVI) reduction | Decline in choroidal vascularity relative to stromal area | variable; often 3-9 months | Enhanced-depth OCT | Reflects hypoxic signaling and VEGF upregulation-mechanistic bridge to neovascularization |

Table 15 summarizes short-range, time-linked biomarkers associated with high-risk AMD progression detectable through AI-Gated physiologic synchronization.

10.4 Drusen-Specific Embodiments and AI-Gated Biochemical Assessment

Drusen are dynamic, multicomponent extracellular deposits whose composition and internal heterogeneity evolve with disease activity. Their biochemical signatures, including amyloid species, oxidized lipids, bisretinoids, cholesterol esters, inflammatory proteins, and lipid-protein structural ratios, are often transient and easily obscured by scatter, redox fluctuation, or motion. The AI-Gated photomodulation system 202 enhances the detection and characterization of drusen by identifying physiologic intervals in which Raman variance decreases, autofluorescence texture stabilizes, and OCT reflectance coherence increases. During these intervals, the AI-Gated photomodulation system 202 obtains clearer biochemical and structural characterization of drusen, including identification of amyloid-associated spectral peaks, shifts in lipid oxidation states, and changes in internal reflectivity that correlate with risk of progression. AI-Gating may operate independently as a standalone analytical layer or in combination with OCT, Raman, autofluorescence, hyperspectral imaging, or other modalities, allowing the clinician or system operator to evaluate composition, temporal instability, and change over time without requiring synchronous hardware. This capability is particularly valuable in assessing early drusen destabilization. Abrupt changes in size, contour, or internal structure can occur weeks to months before exudative conversion. When captured during physiologically coherent intervals, the AI-Gated photomodulation system 202 improves the likelihood of detecting splitting drusen, hyporeflective cores, subretinal drusenoid deposits, and migrating hyperreflective foci, features associated with increased risk of progression. AI-Gating, therefore, provides a physiologically grounded framework for biochemical and structural monitoring of drusen throughout the course of AMD.

TABLE 16

Assessment of AMD and Drusen-Specific Biomarkers Enhanced by AI-Gating

| Biomarker | Modality | Underlying Pathophysiology | What AI-Gating Improves |
|---|---|---|---|
| Drusen Composition (Lipids, Amyloid, Cholesterol Esters) | Raman Spectroscopy | Accumulation of amyloidogenic and lipid-rich deposits | Cleaner Raman peaks during metabolic quieting |
| Ellipsoid Zone Integrity | OCT | Photoreceptor mitochondrial health | Better segmentation when reflectance stabilizes |
| Choriocapillaris Flow Voids | OCTA | Early vascular insufficiency | Flow regularity timing improves detection |
| Subretinal Drusenoid Deposits | OCT/ Reflectance | Basal laminar/RPE pathology | Enhanced contrast when scattering noise drops |
| RPE Autofluorescence Patterns | FAF | Oxidative stress, lipofuscin load | Smoother FAF capture during uniformity phases |
| Retinal Oxygenation Gradients | Hyperspectral | O2 depletion linked to AMD progression | Higher SNR spectral plateau windows |
| VEGF-Associated Microenvironment | Raman/OCTA | Pre-neovascular biochemical milieu | Predictive spikes in Raman bio-signatures |

Table 16 summarizes the principal molecular, structural, vascular, and metabolic biomarkers associated with age-related macular degeneration and drusen evolution. Each biomarker exhibits temporal variability, arising from fluctuations in mitochondrial metabolism, autofluorescence behavior, optical coherence, or microvascular regularity, that can obscure early pathological change when imaging is performed in an ungated, open-loop manner. By forecasting intervals of physiologic stability and optical clarity, the AI-Gating engine 210 aligns each imaging or spectroscopic acquisition with moments in which drusen composition, RPE oxidative load, choriocapillaris perfusion, and photoreceptor integrity are most reliably expressed. The result is a more sensitive, temporally consistent, and clinically actionable assessment of AMD progression and conversion risk.

10.5 AI-Gated Photomodulation for Treatment of AMD

Photobiomodulation and other light-based therapies are traditionally delivered using static timing and fixed illumination parameters, assuming that retinal tissue is uniformly receptive to therapeutic light. Physiologic receptivity, however, fluctuates with mitochondrial activity, oxidative state, and perfusion dynamics. The AI-Gated photomodulation system 202 transforms photomodulation from a time-agnostic procedure into a physiologically synchronized intervention. AI-Gating forecasts short-lived intervals of metabolic receptivity characterized by mitochondrial quieting, reduced oxidative noise, and increased spectral stability. Photomodulation delivered during these intervals may enhance therapeutic efficiency by aligning treatment with the tissue's biologic readiness. The AI-Gated photomodulation system 202 modulates wavelength, power, pulse structure, or duty cycle based on predictive modeling.

The AI-Gated photomodulation system 202 does not require a specific therapeutic mechanism and may be applied to various forms of photobiomodulation intended for metabolic support, inflammatory modulation, or neuroprotective benefit. Through this approach, AI-Gated photomodulation becomes an adaptive, closed-loop therapeutic modality capable of responding to the evolving biologic state of AMD rather than imposing a fixed schedule upon it.

10.6 Pre-Exudative High-Risk AMD AI-Gating Embodiments

Certain forms of AMD progress through a phase characterized by rapid structural and biochemical instability that precedes overt exudation. This stage, referred to here as the premonitory or pre-exudative high-risk AMD state, may unfold over weeks to months and is marked by temporal biomarker fluctuations rather than constant or chronic change. During this interval, collapsing or rapidly evolving drusen, emerging or increasing subretinal drusenoid deposits, newly detected hyperreflective foci, vitelliform-like material, and drusen splitting may occur before leakage is visible on conventional imaging. AI-Gating is uniquely positioned to detect these transitions because the associated biomarkers are temporal rather than purely structural. OCT reflectance coherence, autofluorescence texture stability, Raman spectral variance, and OCTA perfusion regularity fluctuate as these lesions destabilize. By synchronizing acquisition to physiologic windows in which these signals are clearest, the AI-Gated photomodulation system 202 improves the ability to detect collapsing drusen, early biochemical signatures of amyloid and lipid oxidation, migrating hyperreflective foci, and subclinical non-exudative macular neovascularization during perfusion-stable intervals.

These capabilities support earlier recognition of high-risk transformation and provide a non-invasive method for monitoring short-range physiologic instability. The AI-Gated photomodulation system 202 enhances the visibility and reproducibility of biomarkers that are clinically associated with elevated conversion risk.

10.7 Effect of Anti-VEGF Therapy on Retinal Physiologic Stability and Integration with AI-Gating Anti-VEGF therapy, which is widely used in the management of neovascular age-related macular degeneration (AMD), produces several well-documented structural, vascular, and metabolic restorative effects in the retina. Although these pharmacologic treatments are not associated with light-based therapy, the physiologic remodeling effects they induce can enhance the performance of imaging systems that rely on consistent optical or motion conditions, such as the AI-Gating architecture described herein.

Structurally, anti-VEGF therapy decreases intraretinal and subretinal fluid and reduces cystic and contour-related irregularities. These changes produce smoother reflectance boundaries in OCT and improved delineation of the ellipsoid zone (EZ), external limiting membrane (ELM), and RPE complex. Because AI-Gating detects moments of reflectance coherence to forecast high-value acquisition intervals, this post-treatment structural regularity increases the frequency and duration of physiologic stability windows.

Vascular changes are similarly favorable for coherent data capture. Reductions in leakage and neovascular activity lead to more predictable OCT angiography (OCTA) flow patterns with fewer decorrelation spikes. These periods of harmonic flow regularity allow the AI-Gating engine 210 to identify and predict optimal vascular acquisition windows with higher accuracy.

Metabolic and biochemical fluctuations also diminish following anti-VEGF therapy. Fundus autofluorescence (FAF) becomes more uniform, and Raman spectral variability associated with oxidative stress can decrease. The AI-Gating engine 210 identifies these intervals of metabolic quieting and aligns spectral or reflectance-based imaging to periods of maximal signal stability.

Motion stability typically improves as well. As retinal distortion and associated visual disruption decrease, patients demonstrate more consistent fixation with fewer compensatory microsaccades. This results in more frequent motion-quiescent intervals suitable for high-fidelity gated imaging. Collectively, the physiologic stabilization associated with anti-VEGF therapy enhances the operational environment in which AI-Gating performs prediction, gating, and closed-loop refinement. The AI-Gated photomodulation system 202 can therefore generate higher-quality gated OCT, OCTA, FAF, reflectance, hyperspectral, or Raman acquisitions under these more stable conditions. These advantages apply across all embodiments disclosed herein, including standalone devices, multimodal platforms, and external supervisory controllers configured to interface with existing imaging instruments.

10.8 AI-Gating for Disease-Specific Embodiments

The AI-Gating architecture is applicable across a broad spectrum of ophthalmic diseases characterized by structural, vascular, metabolic, or biochemical variability. Because many retinal and choroidal disorders exhibit physiologic instability over short temporal cycles, the system's ability to identify and leverage transient stability intervals enables more reliable imaging, enhanced biomarker detection, and improved monitoring of disease progression or therapeutic response. The following subsections describe exemplary embodiments of AI-Gating applied to specific disease categories. These embodiments are illustrative rather than limiting, and the AI-Gated photomodulation system 202 is compatible with both current and future imaging, spectroscopic, and photomodulation technologies.

10.9 AI-Gated Detection and Monitoring in Diabetic Retinopathy and Diabetic Macular Edema Diabetic retinopathy and diabetic macular edema represent dynamic retinal environments in which vascular, metabolic, and structural abnormalities evolve continuously over short physiologic intervals. Capillary non-perfusion, microaneurysm turnover, endothelial dysfunction, inflammatory signaling, and oscillating retinal thickness create an optical landscape that changes from moment to moment.

OCTA, in particular, is highly sensitive to these fluctuations: flow-void patterns shift with pulsatility; microaneurysm visibility depends on capillary turbulence; and edema-associated scatter varies with hydration state, fixation stability, and micro-motion. These rapidly changing physiologic conditions introduce artifacts that obscure early signs of ischemia, distort measurements of retinal thickening, and compromise the reproducibility required for longitudinal monitoring.

AI-Gating directly addresses this challenge by forecasting the intervals in which diabetic retinal physiology transitions into brief states of vascular and structural coherence. By continuously analyzing reflectance geometry, OCT boundary stability, microsaccadic deceleration, tear-film smoothing, and the rhythmic harmonics of capillary pulsatility, the AI-Gated photomodulation system 202 identifies the precise moments when vascular noise quiets and scatter diminishes.

During these short-lived stability windows, microaneurysms solidify into sharper foci, regions of capillary dropout become more clearly demarcated, and laminar flow patterns appear with greater continuity. OCTA images captured during these predicted intervals reveal ischemic topography with higher fidelity and reduce false interpretations of perfusion deficits caused by motion or scattering rather than true vascular compromise.

In diabetic macular edema, the retina undergoes continuous biomechanical modulation driven by fluid shifts, Müller-cell dysfunction, and transient changes in extracellular matrix pressure. These variations alter the retinal refractive index and modulate intraretinal scatter on a scale too rapid for conventional OCT to track.

AI-Gating detects the moments in which edema-related scatter transiently decreases, enabling the AI-Gated photomodulation system 202 to capture OCT frames during periods of improved boundary definition and reduced noise. These gated acquisitions provide a clearer assessment of cystic change, subretinal fluid, and ellipsoid-zone disruption, enhancing the precision of thickness maps and allowing clinicians to quantify therapeutic response to anti-VEGF or corticosteroid injections with greater accuracy.

Across all stages of diabetic retinopathy, from early microvascular instability to advanced macular edema, the AI-Gated photomodulation system 202 transforms chaotic physiologic fluctuation into a predictable temporal structure. By acquiring images during the narrow intervals when the retina is most optically coherent, metabolically steady, and biomechanically stable, AI-Gating elevates the diagnostic sensitivity of OCT, OCTA, and reflectance imaging. This physiologic synchronization improves the reliability of ischemia detection, sharpens visualization of microaneurysm morphology, enhances the measurement of fluid dynamics, and increases the reproducibility of follow-up imaging.

In a disease where progression can be subtle and treatment decisions hinge on delicate changes in perfusion and edema, AI-Gating provides a precision-timed framework that conventional imaging has never achieved.

TABLE 17

| Diabetic Retinopathy and DME: Physiologic Instabilities and AI-Gated Enhancement | | | | |
|---|---|---|---|---|
| Physiologic/ Optical Instability | Pathophysiologic Basis in DR/DME | Consequences for Conventional Imaging | AI-Gated Enhancement Mechanism | Clinical Impact |
| Capillary flow pulsatility | Hemodynamic irregularities from endothelial dysfunction | Variable OCTA flow signal; inconsistent detection of dropout | Identifies harmonic flow-regularity intervals for stable capture | Improves mapping of ischemia and perfusion deficits |
| Microaneurysm turnover | Dynamic formation and regression of microaneurysms | Frame-to-frame variability in visibility and morphology | Times capture to reflectance-coherent intervals | Enhances sensitivity to early microvascular lesions |
| Inflammatory and metabolic oscillation | Cytokine bursts, oxidative flux, and metabolic instability | Scatter-related noise on OCT/OCTA; unstable FAF | Forecasts metabolic quieting phases for clearer imaging | Improves detection of subclinical inflammatory activity |
| Edema-associated scatter fluctuation | Fluid shifts and tissue hydration changes | Boundary distortion; degraded cyst and fluid visualization | Captures OCT during low-scatter intervals | Sharpens delineation of cysts, SRF, and EZ disruption |
| Thickness and biomechanical modulation | Transient changes in retinal rigidity and ECM pressure | Poor reproducibility of thickness measurements | Captures frames at biomechanically stable moments | Increases accuracy of DME quantification |
| Fixation instability and micro-motion | Diabetic neuropathy affecting fixation control | Motion artifacts; false flow gaps on OCTA | Gating during microsaccadic deceleration | Reduces false-positive flow deficits |

Table 17 shows key diabetic retinal fluctuations and the mechanisms by which AI-Gating improves vascular and structural imaging through physiologic synchronization.

Table 17 outlines the principal physiologic and optical instabilities that characterize diabetic retinopathy and diabetic macular edema, instabilities that arise not from device limitations but from the retina's own dynamic biology.

Diabetic eyes exhibit fluctuating capillary flow, microaneurysm turnover, edema-associated scatter, metabolic oscillations, and biomechanical modulation, all of which destabilize the vascular and structural signals on which OCT and OCTA depend. These fluctuations create a moving target for imaging systems, reducing sensitivity to early ischemia, complicating thickness assessment, and producing variability that undermines longitudinal monitoring.

AI-Gating converts this volatile environment into a predictable temporal framework by forecasting the brief intervals in which vascular turbulence quiets, scatter diminishes, and structural boundaries stabilize. During these physiologically favorable micro-windows, OCTA flow patterns become more coherent, microaneurysms sharpen into discrete foci, and edema-related noise temporarily recedes. By synchronizing imaging to these moments of intrinsic retinal stability, AI-Gating enhances both the clarity and reproducibility of diabetic imaging. This physiologic alignment supports earlier detection of microvascular compromise, more accurate characterization of DME fluid dynamics, and more reliable assessment of therapeutic response across visits.

11.0 AI-Gating in Glaucoma and Other Optic Neuropathies

Glaucoma and related optic neuropathies present a uniquely challenging physiologic environment for ophthalmic imaging systems. These diseases introduce not isolated artifacts, but a continuous and interwoven set of rhythmic and chaotic micro-events that affect nearly every dimension of structural and vascular measurement. Even in an attentive patient with excellent fixation, the eye is never static.

Microsaccades, fixational drift, and high-frequency microtremor create a persistent backdrop of positional jitter that subtly alters the orientation of the peripapillary retina from moment to moment. Although these fluctuations occur on the scale of only a few microns, their magnitude closely mirrors the annual rate of glaucomatous retinal nerve fiber layer loss, meaning that ordinary physiologic motion can easily mimic progression, conceal early disease, or distort longitudinal comparisons.

Blink activity introduces an additional layer of complexity. Each blink triggers rapid tear-film redistribution, transient corneal shape changes, and brief but measurable shifts in intraocular pressure. During the post-blink recovery interval, the biomechanics of the optic nerve head and peripapillary retina have not yet returned to equilibrium, and segmentation algorithms are disproportionately prone to error. Imaging obtained during these unstable windows frequently yields retinal nerve fiber layer (RNFL) or ganglion cell layer measurements that appear thickened, thinned, or structurally irregular for reasons entirely unrelated to disease.

Vascular pulsatility further compounds this variability. With every cardiac cycle, the lamina cribrosa and prelaminar tissues undergo subtle displacement, altering both the mechanical and optical characteristics of the optic nerve head. OCT and OCTA acquisitions captured at different phases of the pulsatile cycle, therefore, do not represent equivalent physiologic states. They reflect moment-to-moment differences in perfusion, tissue compliance, and structural load, and these fluctuations can exceed the degree of glaucomatous change detectable over months or years. Uncoordinated imaging produces inconsistent RNFL readings, unstable neuroretinal rim metrics, and variations in deep laminar visibility that confound progression analysis.

Even the intrinsic reflectance properties of the lamina cribrosa fluctuate with perfusion, oxygenation, and metabolic demand. These shifts alter the backscatter characteristics of the laminar beams and prelaminar tissues, influencing layer segmentation accuracy and degrading the precision of deep optic nerve imaging.

Across all of these physiologic processes, ocular motion, blink recovery, vascular pulsatility, and reflectance modulation, the common denominator is temporal instability that constrains the reliability of conventional OCT, OCTA, reflectance imaging, and deep-layer profiling.

AI-Gating directly addresses this entire constellation of physiologic fluctuation by introducing a predictive temporal intelligence layer that monitors, interprets, and forecasts the dynamics of ocular stability. By continuously analyzing reflectance harmonics, micro-motion signatures, pulsatility cues, and structural coherence trends, the AI-Gating engine 210 identifies the specific future intervals in which the optic nerve head and peripapillary retina will exhibit maximal stability.

Instead of reacting to artifacts after they degrade image quality, the AI-Gated photomodulation system 202 anticipates impending periods of quiescence before they arise and gates imaging or spectral acquisition strictly within those predicted windows. This represents a fundamental shift in glaucoma imaging: the timing of data collection is no longer governed by the device's capture cycle, but by the physiologic readiness of the tissue itself.

This predictive synchronization reduces spurious RNFL fluctuations, suppresses blink-associated distortions, mitigates the effects of cardiac-cycle pulsatility, improves segmentation reliability, and enhances the reproducibility of neuroretinal rim and GCL measurements. The improvement is not incremental; it is structural.

AI-Gating converts inherently unstable ocular behavior into a predictable, biologically coherent temporal framework for imaging. It enables consistent acquisition of RNFL thickness, BMO-MRW metrics, deep laminar profiles, and OCTA flow maps with a degree of reproducibility that has historically been unattainable in glaucoma diagnostics.

In eyes where microns matter, and physiologic noise often exceeds disease signal, AI-Gating restores interpretive clarity. It creates the temporal conditions under which true structural change can be distinguished from transient variability and establishes a new model for artifact-resistant, reliability-optimized glaucoma imaging.

The ability to synchronize imaging to biologically favorable intervals is therefore a central contribution of the AI-Gating architecture and applies across all embodiments, including standalone devices, multimodal systems, and external supervisory controllers that interface with existing imaging platforms.

TABLE 18

Impact of Physiologic Fluctuations on Glaucoma Imaging and the Mitigating Role of AI-Gating

| Physiologic Fluctuation | Magnitude/ Characteristics | Impact on OCT/OCTA and RNFL/GCL Metrics | Contribution of AI-Gating |
|---|---|---|---|
| Microsaccades, Drift, Microtremor | Eye motion of 3-7 microns; continuous during fixation | Produces RNFL variability equal to or greater than yearly glaucoma loss; induces scan-to-scan inconsistency; causes B-scan misregistration | Predicts motion quieting and triggers imaging only during micro-intervals of drift stagnation or microsaccadic pause |
| Blink-Induced Deformation | Tear-film redistribution; corneal shape transients; IOP micro-spikes for 100-300 ms | Causes segmentation errors, RNFL thickness artifacts, reflectance variability, and misinterpretation of rim or GCL boundaries | Detects pre-blink and post-blink fluctuation signatures and suppresses imaging during unstable recovery windows |
| Vascular Pulsatility at ONH | Lamina displacement 2-40 microns per cardiac cycle; flow oscillation | Alters RNFL thickness, ONH contour, and OCTA flow maps; produces rhythmic but unpredictable variability | Identifies diastolic stability intervals and aligns imaging to pulsatility minima for reproducible structural and flow acquisition |
| Lamina Cribrosa Reflectance Variation | Variations with perfusion, metabolic demand, and oxygenation | Alters backscatter properties, producing deep-layer OCT inconsistency; reduces laminar visibility and segmentation accuracy | Uses reflectance harmonics as biomarkers to forecast moments of optimal optical clarity |
| Fixation Instability | Slow drift, instability in diseased or elderly patients | Produces non-uniform sampling of peripapillary sectors; false asymmetry; false progression | Learns fixation pattern in real time and predicts quiescent intervals for sectoral or widefield imaging |
| Optic Nerve Head Biomechanical Fluctuation | Dynamic structural deformation under variable load | Alters BMO-MRW, neuroretinal rim thickness, and peripapillary curvature | Gates imaging when biomechanical consistency is predicted, improving structural repeatability |

Table 18 summarizes the principal physiologic fluctuations that undermine the reliability of structural and vascular imaging in glaucoma, emphasizing both their magnitude and their clinical relevance. These fluctuations, ranging from microsaccadic drift to blink-induced deformation, cardiac-cycle pulsatility, laminar reflectance variability, and fixation instability, introduce noise levels that frequently equal or exceed the degree of true glaucomatous progression. Because these disturbances arise from normal biology rather than device limitations, they cannot be eliminated through hardware improvements alone.

AI-Gating provides a physiologically aligned solution to these problems by forecasting the brief intervals in which the optic nerve head and peripapillary retina are most likely to be stable. Instead of acquiring data during arbitrary or device-driven timing, the AI-Gated photomodulation system 202 synchronizes imaging to predicted periods of minimal motion, consistent reflectance, and hemodynamic quieting.

By aligning data capture to the most favorable physiologic windows, AI-Gating reduces scan-to-scan variability, improves segmentation stability, enhances OCTA flow-map consistency, and allows subtle disease-related changes to emerge with greater clarity. In doing so, AI-Gating transforms unavoidable physiologic noise into a predictable temporal structure that supports more accurate, reproducible, and clinically meaningful imaging across all glaucoma-related embodiments.

11.1 The Role of AI-Gating in Uveitis and Ocular Inflammation

Uveitis and ocular inflammatory diseases create an optical and physiologic environment that is among the most unstable in ophthalmology. Unlike healthy eyes, in which fluctuations arise from motion and vascular pulsatility alone, inflamed eyes exhibit rapid, dramatic, and unpredictable changes that profoundly disrupt the reliability of OCT, OCTA, FAF, and multimodal retinal imaging. Inflammation fundamentally alters the scattering, absorption, fluorescence, and perfusion characteristics of ocular tissues, and these changes may evolve over seconds or even milliseconds.

One of the defining features of uveitis is the presence of dynamic inflammatory scatter. Proteinaceous flare, cellular aggregates, and particulate debris suspended in the aqueous or vitreous continuously modify the optical path. These particles drift, sediment, disperse, and coalesce in ways that alter backscatter patterns from moment to moment. Hyperreflective foci, representing inflammatory cells, activated microglia, or subclinical granulomatous elements, appear and dissolve unpredictably. The result is an imaging field in which brightness, contrast, and signal-to-noise ratios fluctuate far more rapidly than in non-inflamed eyes.

Autofluorescence signals are similarly unstable in uveitis. Oxidative bursts within the retinal pigment epithelium, variable lipofuscin expression, and transient alterations in metabolic load produce irregular autofluorescence intensities that make frame-to-frame interpretation unreliable. OCTA images are compromised by variable flow void patterns, transient capillary hyperpermeability, and dynamic leakage that obscures or mimics true perfusion deficits. Even the retinal and choroidal layers themselves undergo inflammatory thickening, redistribution of fluid, and localized biomechanical deformation that can shift segmentation boundaries across scans taken only seconds apart.

These inflammatory fluctuations create a diagnostic landscape in which conventional timing paradigms break down. Images captured in one moment may falsely suggest cystoid edema, while those taken moments later may hide it entirely. Subclinical fluid pockets, especially in intermediate or posterior uveitis, may be visible only during short intervals when scatter temporarily recedes. Vascular leakage produces transient OCTA artifacts that mimic flow loss, and inflammatory hyperreflective deposits may appear or disappear depending on the precise alignment between tissue motion, flare density, and device acquisition timing.

AI-Gating addresses these challenges by leveraging the temporal volatility of uveitic physiology as a source of information rather than noise. The AI-Gated photomodulation system 202 continuously monitors reflectance fluctuations, scatter harmonics, autofluorescence oscillations, flow-related variance, and local textural changes that correlate with inflammatory burden. These time-varying signatures allow the AI-Gating engine 210 to identify micro-intervals in which inflammatory activity temporarily quiets, moments in which scatter diminishes, oxidative instability recedes, and vascular leakage enters brief periods of relative equilibrium.

Instead of capturing data indiscriminately or reacting to degraded image quality after the fact, AI-Gating anticipates the emergence of these calmer physiologic windows before they occur. It synchronizes OCT, OCTA, FAF, or multimodal acquisition precisely to these predicted intervals, enabling the AI-Gated photomodulation system 202 to pierce through the turbulent optical environment created by inflammation. This predictive synchronization reveals subtle structural details that would otherwise be obscured: shallow subretinal fluid, parafoveal thickening, evolving granulomas, and inflammatory aggregates that escape detection during more chaotic intervals.

In chronic uveitis, where clinical management depends heavily on reliable serial imaging, AI-Gating offers a transformative advantage. By aligning follow-up imaging to physiologically analogous windows of inflammatory quiescence, the AI-Gated photomodulation system 202 produces longitudinal data with dramatically improved reproducibility. This consistency enables earlier detection of flare or recurrence, more accurate quantification of treatment response, and tighter titration of corticosteroids, immunomodulators, or biologic therapies. In acute disease, AI-Gating allows clinicians to visualize inflammatory architecture that is otherwise masked by optical noise.

In this way, AI-Gating does not simply improve imaging quality, it creates a novel imaging paradigm for inflammatory disease. It transforms the unpredictable turbulence of uveitis into a structured temporal landscape that can be forecasted, navigated, and exploited for diagnostic clarity. By capturing information only during biologically favorable intervals, the AI-Gated photomodulation system 202 delivers clearer, more stable, and clinically actionable images across all inflammatory phenotypes and disease severities.

TABLE 19

Impact of Inflammatory Fluctuations in Uveitis on Retinal Imaging and the Mitigating Role of AI-Gating

| Inflammatory Fluctuation | Magnitude/ Characteristics | Impact on OCT, OCTA, FAF, and Multimodal Imaging | Contribution of AI-Gating |
|---|---|---|---|
| Proteinaceous flare and inflammatory | Rapidly changing density of proteins, | Causes unpredictable backscatter, contrast | Predicts transient reductions in scatter and |

TABLE 19-continued

Impact of Inflammatory Fluctuations in Uveitis on Retinal Imaging and the Mitigating Role of AI-Gating

| Inflammatory Fluctuation | Magnitude/ Characteristics | Impact on OCT, OCTA, FAF, and Multimodal Imaging | Contribution of AI-Gating |
|---|---|---|---|
| scatter | cells, and particulate debris; fluctuates over seconds | instability, variable signal attenuation, and degraded B-scan clarity | targets acquisition to these brief clarity windows |
| Hyperreflective foci and mobile inflammatory aggregates | Moving cellular elements and aggregates with variable optical signatures | Create false positives for edema, exudate, or hyperreflective pathology; obscure subtle structural details | Detects fluctuation patterns and forecasts intervals when aggregates are least disruptive |
| Autofluorescence instability from oxidative bursts | Rapid metabolic oscillations in RPE; fluctuating lipofuscin signal intensity | Produces frame-to-frame FAF inconsistency, masking RPE lesions or inflammatory disturbances | Identifies and synchronizes capture to oxidative quieting periods with more stable autofluorescence |
| Vascular leakage and transient OCTA flow voids | Rapid alternation between leakage, hyperpermeability, and temporary flow attenuation | OCTA maps display non-physiologic voids, false perfusion deficits, and inconsistent capillary density | Forecasts periods of vascular equilibrium, aligning OCTA acquisition to authentic flow states |
| Choroidal thickening and dynamic biomechanical shifts | Inflammatory swelling, shifting fluid compartments, dynamic mechanical deformation | Alters segmentation boundaries and per-scan choroidal profiles, complicating progression assessment | Learns deformation patterns and triggers imaging when biomechanical variability stabilizes |
| Tissue motion from ocular discomfort, photophobia, or reflex tearing | Increased blink rate, fixation instability, reflex micro-movements | Causes motion artifacts, segmentation errors, and inconsistent structural maps | Automatically suppresses acquisition during unstable intervals and predicts windows of residual fixation |
| Macular and perivascular edema fluctuations | Edema pockets appear, expand, or recede rapidly; fluid shifts across scans | Creates inconsistent thickness maps; subtle fluid may be visible only intermittently | Captures scans during predicted fluid-clarity intervals, enabling reliable visualization of micro-cystic changes |

Table 19 highlights the major sources of physiologic and optical instability that arise in uveitis and related inflammatory disorders, each of which can undermine the reliability of structural and vascular imaging. Inflammatory scatter, shifting hyperreflective deposits, oxidative autofluorescence fluctuations, dynamic leakage patterns, biomechanical thickening, and reflex-driven motion all contribute to rapid frame-to-frame variability. These disturbances can obscure subclinical fluid, distort segmentation boundaries, mimic perfusion loss, or generate inconsistent thickness profiles, making it difficult to detect flare, quantify treatment response, or track disease progression.

AI-Gating provides a physiologically synchronized alternative by forecasting the short-lived intervals in which inflammatory activity temporarily quiets. During these moments, scatter density drops, autofluorescence stabilizes, and vascular leakage enters brief periods of relative equilibrium.

By aligning image acquisition to these favorable physiologic windows, AI-Gating improves visualization of subtle inflammatory architecture, enhances the reproducibility of serial imaging, and supports more accurate therapeutic decision-making. In doing so, AI-Gating transforms the volatile optical environment of uveitis into a structured, predictable timing landscape that enables higher-quality diagnostic imaging across all inflammatory phenotypes.

11.2 Retinal Vascular Occlusions and the Role of AI-Gating

Retinal vascular occlusions create some of the most physiologically volatile environments in ophthalmic imaging. Whether involving a branch retinal vein occlusion, a central vein occlusion, or an arterial occlusion, the retina undergoes rapid, unpredictable, and spatially heterogeneous fluctuations in perfusion, oxygenation, edema distribution, and vascular remodeling. These changes occur not only across days or hours, but also across seconds, and even within the duration of a single imaging session. As a result, conventional OCT and OCTA systems often capture snapshots that represent transient physiologic states rather than stable, interpretable markers of underlying pathology.

In venous occlusions, perfusion is characterized by unstable flow dynamics, intermittent capillary dropout, pulsatile venous congestion, and the emergence of collateral channels that change their caliber and flow characteristics over short intervals. OCTA imaging captured during periods of flow irregularity often shows nonperfusion areas, flow voids, or apparent capillary dropout that do not correspond to persistent ischemia but rather to momentary hemodynamic turbulence. These physiologic fluctuations obscure the true extent of ischemia, reduce the reliability of perfusion maps, and complicate the assessment of collateral vessel development.

Arterial occlusions introduce a different but equally unstable physiology. Areas of profound ischemia coexist with islands of partial reperfusion, and localized pockets of metabolic recovery can emerge unpredictably. The resulting mosaics of variable oxygenation and residual flow create OCTA patterns that shift from frame to frame. Without temporal coordination, imaging acquisitions reflect these chaotic hemodynamic transitions, leading to inconsistent visualization of watershed zones, macular nonperfusion, or residual perifoveal flow.

Structural OCT is similarly affected. Edema in vein occlusion evolves dynamically, with cystic spaces expanding or collapsing within short time intervals depending on local hydrostatic forces. Subretinal and intraretinal fluid layers exhibit similar volatility. Even the degree of disorganization of the retinal inner layers (DRIL), a prognostic biomarker, can appear more or less severe depending on the degree of momentary scatter, motion, or biomechanical distortion at the time of image capture.

AI-Gating transforms the imaging paradigm for retinal vascular occlusions by forecasting the specific intervals in which perfusion regularity, vascular quieting, and optical stability are most likely to occur. By analyzing temporal fluctuations in flow variance, reflectance patterns, motion signatures, and scatter dynamics, the AI-Gating engine 210 identifies the moments in which OCTA is most likely to represent authentic perfusion rather than hemodynamic noise. Imaging triggered during these predicted physiologic windows yields more reliable maps of nonperfusion, collateral circulation, and macular ischemia.

At the same time, AI-driven reflectance gating enhances structural OCT in these unstable disease states. When acquisition is confined to moments of minimal motion, reduced scatter, and relative biomechanical equilibrium, the resulting images more accurately delineate cystoid edema, subtle subretinal fluid, foveal contour, and the boundaries of DRIL. This level of temporal targeting improves clinical interpretation, supports more robust prognostic assessment, and enhances the ability to track treatment response across follow-up visits.

In retinal vascular occlusions, where perfusion instability and structural volatility are intrinsic features of the disease, AI-Gating provides a physiologically synchronized strategy for capturing the most meaningful and least distorted images. By aligning both vascular and structural imaging to periods of predictable stability, the AI-Gated photomodulation system 202 delivers clearer, more reproducible, and more clinically actionable information across all occlusive phenotypes.

TABLE 20

Hemodynamic and Structural Instability in Retinal Vascular Occlusions and the Role of AI-Gating

| Fluctuation in Vascular Occlusion | Magnitude/Nature of Instability | Impact on OCT/OCTA | Contribution of AI-Gating |
|---|---|---|---|
| Unstable flow dynamics and fluctuating capillary perfusion | Moment-to-moment changes in flow velocity and capillary visibility | Produces transient flow voids, false non-perfusion, and unreliable ischemia maps | Predicts intervals of flow regularity and synchronizes OCTA to these stable moments |
| Collateral vessel remodeling | Collaterals change caliber and flow characteristics within short intervals | Inconsistent visualization of collateral networks and venous bypass pathways | Targets acquisition to moments when collateral flow is stable enough for accurate depiction |
| Venous congestion and pulsatile flow variability | Hemodynamic turbulence, irregular venous outflow | Flow signal dropout, pulsatile artifacts, macular ischemia misinterpretation | Forecasts low-turbulence intervals to obtain more reliable flow maps |
| Dynamic edema in BRVO/CRVO | Cystoid spaces expand and collapse rapidly; subretinal fluid fluctuates | Inconsistency in edema visualization and DRIL boundaries | Gates structural OCT to motion-quiet, scatter-minimized intervals for stable thickness profiles |
| Metabolic variability and oxygenation gradients | Patchy reperfusion and local hypoxia-reversal zones | Autofluorescence irregularity, OCTA signal variability | Uses reflectance and FA-related harmonics to capture imaging during metabolic equilibrium |
| Tissue motion from ischemic discomfort or transient fixation loss | Increased micro-motion due to visual distortion | Motion artifacts degrade both OCT and OCTA | Suppresses capture during motion bursts and predicts quiescent intervals |

Table 20 shows key physiologic fluctuations in retinal vascular occlusions and how AI-Gating stabilizes OCT and OCTA acquisition by forecasting perfusion-regularity and optical-clarity intervals.

Table 20 captures the defining physiologic instabilities that characterize retinal vascular occlusions, fluctuating perfusion pressure, dynamic collateral recruitment, oscillating venous congestion, and irregular metabolic signaling, each of which creates a highly variable optical environment. Conventional OCT and OCTA systems acquire images at arbitrary moments within these unstable cycles, causing ischemic regions, flow voids, and deep-layer distortions to appear inconsistently from frame to frame. These fluctuations generate artifacts that can obscure early ischemia, distort the apparent extent of capillary non-perfusion, and limit the reliability of follow-up imaging.

AI-Gating mitigates these limitations by predicting the narrow intervals during which perfusion harmonizes, scattering transiently decreases, and structural coherence improves. By synchronizing OCT and OCTA acquisition to these physiologically favorable windows, the AI-Gated photomodulation system 202 produces more stable visualization of macular ischemia, collateral vascular patterns, cystic edema, and DRIL architecture. Through this physiologic timing strategy, AI-Gating enhances diagnostic precision, reduces false variability, and supports more accurate assessment of both acute severity and longitudinal recovery in vascular occlusive disease.

11.3 Geographic Atrophy (Non-Exudative AMD) and the Role of AI-Gating

Geographic atrophy (GA) presents a distinctive physiologic and optical landscape in which the retina and retinal pigment epithelium undergo progressive degeneration, metabolic collapse, and loss of structural integrity. These changes do not occur as static anatomic transformations but as a sequence of highly dynamic and spatially heterogeneous events that reshape the optical behavior of the fundus from moment to moment.

As RPE cells fail, the metabolic oscillations that normally regulate autofluorescence become erratic; pockets of residual lipofuscin alternate between periods of oxidative flare and transient quiescence. These fluctuations create a constantly shifting autofluorescence signature that can cause conventional FAF imaging to misrepresent the size or border activity of atrophic lesions, depending on the precise timing of acquisition.

Structural instability is equally pronounced. The margins of a GA lesion are physiologically active, undergoing continuous cycles of photoreceptor loss, RPE thinning, and microcollapses of the outer retina. These transitions alter local reflectance, scattering, and backshadowing characteristics with considerable temporal variability. OCT images acquired during phases of heightened scatter or transient biomechanical distortion often exaggerate lesion boundaries, obscure nascent islands of preserved tissue, or misrepresent the slope and contour of the atrophic margin. Even the choroidal signal fluctuates as perfusion and oxygenation shift beneath the exposed outer retina.

Fixation instability is another hallmark of GA. Patients often adopt eccentric fixation patterns that drift and re-center unpredictably as the foveal region becomes dysfunctional. These micro-events generate motion and variable sampling angles that, when uncoordinated with image capture, lead to segmentation errors, inconsistent thickness profiles, and unreliable longitudinal measurements of atrophy progression.

AI-Gating provides a physiologically informed solution to these challenges by forecasting the intervals in which the GA-affected retina enters a transient state of stability, periods when autofluorescence noise diminishes, reflectance patterns smooth, motion subsides, and metabolic oscillations momentarily converge. By continuously interpreting the temporal behavior of reflectance coefficients, FAF fluctuation rates, motion vectors, and structural coherence metrics, the AI-Gating engine 210 identifies when the optical environment is most favorable for high-fidelity imaging.

In FAF imaging, this predictive timing isolates the brief moments in which oxidative flare is minimal and autofluorescence texture is least variable, enabling more accurate delineation of GA borders and a more reliable characterization of junctional zone activity. In OCT acquisition, gating to periods of structural quiescence improves visualization of the atrophic slope, preserves the fidelity of the ellipsoid zone and RPE boundaries, and stabilizes choroidal penetration depth. For progression analysis, this consistency is important: measurements of GA area, lesion enlargement rate, and transition-zone thickness become meaningfully reproducible only when driven by physiologically synchronized imaging.

In eyes with extensive GA, where optical instability is an intrinsic feature of the disease, AI-Gating transforms a fluctuating environment into one that can support high-precision diagnostics. By aligning image capture with endogenous moments of coherence and stability, the AI-Gated photomodulation system 202 produces clearer borders, more interpretable FAF maps, and more reliable OCT metrics for staging, monitoring, and therapeutic assessment. This physiologic synchronization restores the diagnostic reliability that GA pathology disrupts, enabling clinicians to discriminate true progression from transient artifact and to follow disease trajectory with unprecedented temporal precision.

TABLE 21

Optical and Physiologic Instability in Geographic Atrophy and the Stabilizing Role of AI-Gating

| Physiologic or Optical Instability in GA | Nature of Fluctuation | Impact on OCT/FAF Imaging | Stabilizing Role of AI-Gating |
|---|---|---|---|
| Autofluorescence variability from lipofuscin remnants | Oxidative micro-bursts and transient quiet periods | Borders of GA appear irregular or inflated depending on flare state | Gating predicts oxidative quieting and captures FAF when metabolic noise is minimal |
| Dynamic structural behavior at lesion margins | Cycles of microcollapse, thinning, and reflectance shifts | Unstable delineation of atrophic edges and misrepresentation of lesion geometry | Targets imaging to intervals of structural coherence for consistent boundary definition |
| Choroidal reflectance fluctuations | Perfusion and oxygenation oscillations beneath atrophic retina | Variable choroidal visibility and inconsistent depth profiles | Synchronizes OCT acquisition with perfusion-regularity intervals for stable choroidal signals |
| Fixation instability and eccentric viewing | Rapid, unpredictable microsaccades and drifting fixation loci | Motion artifacts, segmentation errors, and inconsistent thickness maps | Predicts motion-quiet windows and triggers capture during periods of relative fixation stability |

TABLE 21-continued

Optical and Physiologic Instability in Geographic Atrophy and the Stabilizing Role of AI-Gating

| Physiologic or Optical Instability in GA | Nature of Fluctuation | Impact on OCT/FAF Imaging | Stabilizing Role of AI-Gating |
|---|---|---|---|
| Scatter variation from outer retinal collapse | Changes in scattering angle as photoreceptors degenerate | Fluctuating image contrast and boundary uncertainty | Selects moments of reduced scatter to optimize OCT clarity |
| Metabolic instability at transition zones | Temporal oscillations in stressed but not fully atrophic tissue | FAF misinterpretation of junctional activity; OCT variability in EZ/RPE continuity | Captures images during metabolic plateaus for reproducible assessment of progression |

Table 21 captures the principal sources of physiologic and optical instability that complicate imaging in geographic atrophy. Autofluorescence patterns fluctuate with metabolic noise; structural boundaries at the atrophic margins shift from moment to moment; fixation becomes unstable; and choroidal visibility varies with underlying perfusion. These dynamic processes introduce inconsistency into both OCT and FAF imaging, making lesion borders and progression metrics difficult to interpret with confidence.

AI-Gating directly mitigates these challenges by forecasting the brief, recurring intervals in which each of these instabilities temporarily subsides. By aligning image capture to moments of oxidative quieting, structural coherence, motion stability, and perfusion regularity, the AI-Gated photomodulation system 202 produces more faithful representations of GA lesion geometry, transition-zone activity, and choroidal architecture. This physiologically synchronized timing significantly enhances the reproducibility and clinical utility of imaging in eyes affected by geographic atrophy.

11.4 AI-Gated Detection and Monitoring of Drug-Induced (Toxic) Maculopathy

Drug-induced maculopathy represents one of the most diagnostically subtle categories of retinal disease, in which early structural and metabolic abnormalities arise not as fixed findings but as transient, fluctuating signatures that appear and disappear across short physiologic intervals. Hydroxychloroquine, chloroquine, pentosan polysulfate, tamoxifen, phenothiazines, MEK inhibitors, serotonin-modulating agents, and retinoids all produce characteristic disturbances in photoreceptor integrity, RPE metabolism, autofluorescence behavior, choriocapillaris flow, and Raman biochemical signals.

Yet these pathologic signatures rarely remain stable long enough for conventional static imaging to capture them reliably. Instead, fixation variability, tear-film cycling, micro-motion, oxidative bursts, and microvascular pulsatility continuously modulate the visibility of these early toxic markers, making them easy to miss and difficult to monitor with confidence.

AI-Gating directly addresses this diagnostic limitation by introducing a physiologic monitoring subsystem 208 that predicts when toxic signatures are most likely to be physiologically expressed. By continuously analyzing reflectance coherence, tear-film uniformity, microsaccadic deceleration, autofluorescence variance, OCT boundary sharpness, spectral quieting in Raman signals, and perfusion regularity on OCTA, the AI-Gated photomodulation system 202 forecasts the brief windows in which the retina temporarily enters a state of motion quieting, metabolic plateau, oxidative stability, or vascular coherence. During these predicted intervals, the earliest manifestations of toxicity become more detectable, producing a momentary increase in contrast, stability, and interpretability that traditional systems fail to exploit.

These predictive windows are highly meaningful in hydroxychloroquine-associated toxicity, where early parafoveal photoreceptor stress manifests as subtle ellipsoid-zone (EZ) reflectance attenuation. Because EZ visibility fluctuates with micro-motion, tear-film quality, and reflectance noise, static OCT often misses this earliest change. AI-Gating identifies the moments in which reflectance coherence peaks and micro-movement subsides, allowing acquisition precisely when the EZ attenuation is most apparent, supporting detection before irreversible parafoveal loss occurs.

In pentosan polysulfate toxicity, the mottled autofluorescence patterns and choriocapillaris flow irregularities that characterize early disease fluctuate significantly with oxidative load and vascular micro-pulsatility. FAF images captured at arbitrary times may either exaggerate or mask pathology. By forecasting intervals of metabolic quieting and perfusion regularity, AI-Gating produces FAF and OCTA maps with substantially reduced noise and fewer false-negative examinations, enabling timelier drug discontinuation.

Tamoxifen toxicity introduces another layer of complexity: crystalline deposits and micro-vacuolar changes are easily obscured by fixation instability or subtle fluctuations in reflectance. AI-Gating selectively triggers imaging during motion-stable and reflectance-coherent intervals, producing high-contrast visualization of hyperreflective crystalline bodies and early microcystic changes that might otherwise be lost within physiologic noise.

Across all drug-induced maculopathies, the AI-Gated photomodulation system 202 interprets a diverse set of temporal biomarkers, such as Raman peak variance, autofluorescence micro-oscillations, OCT reflectivity harmonics, and choriocapillaris flow pulsatility, to identify when toxic signatures are at their most physiologically expressive. This transforms toxic maculopathy surveillance from a static process governed by device timing into a dynamic, patient-specific process governed by biological readiness.

As a result, longitudinal follow-up with AI-Gating becomes more reproducible, as each visit's data are captured in physiologically comparable states. Clinicians can detect early toxicity with greater sensitivity, assess reversibility after drug withdrawal with greater fidelity, and identify subtle but directional changes that signal impending progression.

AI-Gating may function as a standalone layer applied to existing imaging platforms or as part of an integrated multimodal system that unifies OCT, OCTA, FAF, Raman spectroscopy, hyperspectral imaging, or photomodulation under a single predictive timing supervisor. In every embodiment, the technology improves sensitivity, suppresses technician- and patient-dependent variability, and introduces a physiologically synchronized diagnostic paradigm that traditional imaging cannot achieve.

The disclosed AI-Gating architecture introduces a prediction-based control layer that identifies temporal biomarkers of physiologic stability, including fixation-quiet intervals, reflectance-coherence windows, metabolic-plateau phases, and perfusion.

TABLE 22

Biomarkers Associated with Toxic Maculopathy and Their Enhanced Detection Through AI-Gating.

| Biomarker/ Pathologic Feature | Modality | Biologic Basis in Toxicity | How AI-Gating Enhances Detection | Clinical Significance |
|---|---|---|---|---|
| Mitochondrial redox instability | NIR reflectance/ Raman | Oxidative stress impairs photoreceptor metabolism | Predicts metabolic-quiet intervals that stabilize Raman/NIR signals | Identifies early photoreceptor stress before OCT findings |
| Bisretinoids (A2E, A2F, toxic lipofuscin) | FAF/ Raman | Accumulate in HCQ and tamoxifen toxicity | Times FAF to low-variance phases, reducing oxidative noise | Detects RPE burden prior to pigment disruption |
| RPE autofluorescence granularity | FAF | Early RPE stress from drug deposition | Captures FAF during uniformity intervals | Sensitive marker for early HCQ/tamoxifen toxicity |
| Ellipsoid-zone attenuation | OCT | Photoreceptor outer-segment injury | Uses reflectance coherence peaks to better resolve EZ | Detects pre-atrophic parafoveal EZ disruption |
| Crystalline deposits | OCT/ Reflectance | Tamoxifen/phenothiazine deposition | Captures reflectance during micro-motion quiescence | Improves visibility of faint crystal bodies |
| Subclinical perfusion irregularity | OCTA | Toxicity disrupts choriocapillaris microflow | Times capture to perfusion-regularity intervals | Earlier detection of vascular compromise |
| Lipid oxidation signatures | Raman | Free-radical-mediated lipid peroxidation | Aligns Raman with spectral plateau phases | Reveals metabolic injury invisible to OCT |
| Amyloid-like conformational shifts | Raman | β-sheet aggregation induced by some agents | Gated acquisition improves weak amyloid-peak detection | May correlate with drusen-like or degenerative changes |

Table 22 shows the representative biomarkers of drug-induced maculopathy and the mechanisms by which AI-Gating improves their detectability through physiologic synchronization.

TABLE 23

Drug-Induced Maculopathy: Temporal Biomarkers and AI-Gated Advantages

| Drug Class/Agent | Mechanism of Retinal Toxicity | Key Structural/ Biochemical Findings | Temporal Biomarkers Relevant to AI-Gating | Primary AI-Gated Modality | Clinical Significance |
|---|---|---|---|---|---|
| Hydroxychloroquine/ Chloroquine | Lysosomal dysfunction; bisretinoid accumulation | Parafoveal EZ loss; perifoveal thinning; FAF changes | FAF volatility; EZ attenuation drift; Raman spectral quieting | OCT, FAF, Raman | Early detection before visual field defects |
| Sertraline/SSRIs | RPE and choroidal effects | Reversible cystoid changes | Reflectance instability; perfusion variability | OCT/ OCTA | Avoids false-positive edema |

TABLE 23-continued

Drug-Induced Maculopathy: Temporal Biomarkers and AI-Gated Advantages

| Drug Class/Agent | Mechanism of Retinal Toxicity | Key Structural/ Biochemical Findings | Temporal Biomarkers Relevant to AI-Gating | Primary AI-Gated Modality | Clinical Significance |
|---|---|---|---|---|---|
| Tamoxifen | Microtubule disruption; crystalline deposition | Crystals; cavitations; hyperreflective foci | HRF migration; lipid-protein spectral shifts | OCT + Raman | Differentiates from MacTel patterning |
| Pentosan polysulfate | RPE/ECM disruption | Parafoveal pigment changes; early macular atrophy | FAF heterogeneity oscillations; reflectance drift | FAF, OCT | Detects early toxicity for drug cessation |
| MEK inhibitors | Fluid-transport disruption | Serous detachment; EZ irregularity | Fluid-wave fluctuation patterns | OCT | Prevents misinterpretation of transient fluid |
| Isotretinoin | Disrupted photoreceptor turnover | Subtle outer-segment irregularity | Tear-film oscillation affecting reflectance | Reflectance + OCT | Improves detection despite surface instability |

Table 22 and Table 23 illustrate the central insight underlying the application of AI-Gating to toxic maculopathy: early toxic changes are not consistently visible, but instead emerge only during brief, physiologically favorable intervals. These windows correspond to metabolic quieting, autofluorescence uniformity, vascular coherence, or the momentary stabilization of photoreceptor reflectance.

By forecasting these intervals from temporal biomarkers, AI-Gating captures imaging and spectroscopic data at the precise moments when toxic signatures are most detectable. This physiologic synchronization improves sensitivity to early damage, reduces false-negative examinations, and ensures that longitudinal comparisons reflect true biologic change rather than unstable optical conditions.

11.5 AI-Gated Imaging in Inherited Retinal Dystrophies

Inherited retinal dystrophies create a uniquely unstable optical environment in which degenerating photoreceptors, dysfunctional RPE cells, and remodeling of retinal architecture produce highly variable signals across short physiologic intervals. Conditions such as retinitis pigmentosa, Stargardt disease, cone-rod dystrophy, and Best disease introduce oscillating reflectance patterns, shifting autofluorescence signatures, and fluctuating OCT boundary coherence. These instabilities arise from residual photoreceptor metabolic activity, mitochondrial stress cycles, variable lipofuscin loading, and micro-saccadic fixation instability, factors that can obscure early disease progression or exaggerate apparent structural change.

AI-Gating transforms this challenge by forecasting the brief intervals in which genetically stressed tissue enters transient periods of structural calm, metabolic quieting, or reflectance stability. During these windows, the ellipsoid zone becomes more sharply defined, RPE autofluorescence patterns stabilize into consistent textures, and OCT boundary segmentation improves markedly. In diseases like retinitis pigmentosa, AI-Gated acquisition captures the fleeting moments in which hyperreflective rings, ONL thickness profiles, and early EZ attenuation become most interpretable. In Stargardt disease, fluctuating fleck autofluorescence and RPE granularity settle momentarily into uniform patterns that better reveal subclinical expansion of atrophic zones.

Across the spectrum of IRDs, AI-Gating enables more precise documentation of progression by aligning each scan with comparable physiologic states, reducing false variability and allowing subtle but meaningful change to emerge with clarity.

TABLE 24

Inherited Dystrophies: Physiologic Instabilities and AI-Gated Imaging Advantages.

| Instability/ Biomarker | Pathophysiologic Basis in IRDs | Impact on Conventional Imaging | AI-Gated Enhancement Mechanism | Clinical Importance |
|---|---|---|---|---|
| Oscillating EZ reflectance | Photoreceptor metabolic stress and degeneration | Inconsistent visibility of EZ integrity | Captures OCT during reflectance-coherence peaks | Earlier detection of subtle EZ loss |
| Variable autofluorescence from lipofuscin | RPE dysfunction and bisretinoid accumulation | Unstable FAF patterns; poor reproducibility | Times FAF to uniform, low-variance intervals | Improved monitoring of RPE deterioration |
| Fixation drift and micro-saccadic instability | Loss of central cone function | Motion artifacts; segmentation errors | Gates imaging during microsaccadic deceleration | More stable foveal and perifoveal imaging |

TABLE 24-continued

Inherited Dystrophies: Physiologic Instabilities and AI-Gated Imaging Advantages.

| Instability/ Biomarker | Pathophysiologic Basis in IRDs | Impact on Conventional Imaging | AI-Gated Enhancement Mechanism | Clinical Importance |
|---|---|---|---|---|
| Hyperreflective foci migration | Degenerating photoreceptors and microglial activity | Apparent positional shifts between scans | Captures frames during structural quieting | Better characterization of HRF movement |
| Atrophic boundary variability | Choriocapillaris and RPE thinning | Irregular FAF/OCTA delineation | Identifies metabolic quieting intervals | More precise measurement of atrophy kinetics |

Table 24 is representative of physiologic and optical fluctuations in inherited retinal dystrophies and how AI-Gating improves diagnostic clarity by synchronizing imaging to periods of enhanced structural and metabolic stability.

Table 25 summarizes exemplary embodiments across major inherited retinal diseases, illustrating the biomarkers most relevant to each condition and the manner in which AI-Gating enhances diagnostic precision, longitudinal reliability, and treatment response monitoring.

TABLE 25

AI-Gated Embodiments for Inherited Retinal Degenerations

| IRD Condition | Key Biomarkers | Source of Temporal Instability | AI-Gating Enhancement | Resulting Diagnostic/ Monitoring Value |
|---|---|---|---|---|
| Retinitis Pigmentosa (RP) | Ellipsoid-zone (EZ) residual islands; parafoveal hyper-AF ring; outer-retinal thickness | Fixation drift, tear-film oscillation, reflectance variability in low-signal retina | Captures frames only during motion-quiet and reflectance-coherent intervals | Sharper EZ boundary detection; improved residual photoreceptor quantification; more reliable progression rates |
| Stargardt Disease (ABCA4-related) | Bisretinoid (A2E/A2F) accumulation; parafoveal AF granularity; fleck morphology | FAF and hyperspectral signals fluctuate with oxidative microbursts and metabolic instability | Aligns acquisition to autofluorescence stability and spectral-plateau phases | Clearer discrimination of fleck evolution; improved lipofuscin load tracking; earlier detection of parafoveal expansion |
| Cone-Rod Dystrophy | Central cone loss; macular EZ attenuation; foveal AF alteration | Sensitive to fixation instability, light-adaptation state, and reflectance cycling | Times OCT/FAF to fixation-stable and reflectance-coherent windows | Enhanced quantification of cone loss; reduced segmentation error; improved cross-visit comparison |
| Choroideremia | Choriocapillaris flow loss; RPE atrophy margins; preserved islets | OCTA flow varies with pulsatility and motion; reflectance fluctuates at atrophy borders | Triggers OCTA during perfusion-regularity and coherence intervals | Improved visualization of preserved choroidal islands; more consistent atrophy-expansion measurement |
| Bietti Crystalline Dystrophy | Crystalline deposits; choroidal thinning; lipid-oxidation signatures | Raman/hyperspectral signals vary with redox-linked metabolic transitions | Restricts biochemical acquisition to mitochondrial-quiet and spectral-plateau phases | Higher-fidelity biochemical profiling; potential differentiation of crystalline vs. non-crystalline changes |
| Usher Syndrome | RP-like degeneration with vestibular-induced fixation variability | Increased motion artifact due to balance-related instability | Motion-adaptive gating across eye-tracking streams | High-quality datasets despite fixation challenges; supports meaningful longitudinal monitoring |

TABLE 25-continued

| AI-Gated Embodiments for Inherited Retinal Degenerations | | | | |
|---|---|---|---|---|
| IRD Condition | Key Biomarkers | Source of Temporal Instability | AI-Gating Enhancement | Resulting Diagnostic/ Monitoring Value |
| Best Disease/ Vitelliform Disorders | Vitelliform material reflectance; AF pooling; subretinal deposits | FAF uniformity fluctuates; Raman lipid signatures vary with metabolic state | Aligns capture to transient AF uniformity and lipid-signal plateau | Improved detection of early collapse and pseudohypopyon transition; earlier destabilization recognition |
| Pattern Dystrophies | FAF texture signatures; RPE reflectance heterogeneity; subretinal deposits | Autofluorescence textural noise decreases intermittently | Capture during low-variability intervals | Improved distinction between benign patterns and early atrophy; enhanced diagnostic confidence |

Table 25 presents exemplary, non-exclusive embodiments of AI-Gating in inherited retinal degenerations. The examples are provided for illustration only and are not intended to limit the scope of the inventions, but to demonstrate how physiologic synchronization may enhance visualization and longitudinal assessment of temporally unstable biomarkers.

11.6 AI-Gated Imaging in Central Serous Chorioretinopathy (CSR)

Central serous chorioretinopathy is characterized by dynamic and rapid fluctuations in choroidal thickness, subretinal fluid height, RPE barrier integrity, and choroidal hyperpermeability. These fluctuations occur on timescales ranging from milliseconds to seconds, driven by pulsatile choroidal congestion, transient RPE pump variability, tear-film shifts, and motion instability associated with distorted central vision.

As a result, OCT and OCTA images captured at arbitrary moments may misrepresent the true magnitude of subretinal fluid, obscure early RPE microrips or "blowouts," and distort the appearance of choriocapillaris flow deficits. This physiologic volatility makes CSR particularly vulnerable to false progression signals and inconsistent follow-up imaging.

AI-Gating provides a substantial diagnostic advantage by forecasting the short-lived periods in which CSR-related fluctuations are temporarily quiet. During these brief intervals, subretinal fluid height stabilizes, choroidal pulsatility enters harmonic phases, and RPE reflectance coherence improves. OCT scans acquired during these windows reveal more accurate morphology of pigment epithelial detachments, enhanced visualization of RPE microrips, and clearer delineation of SRF boundaries.

In OCTA, AI-Gating reduces artifacts arising from pulsatile flow irregularities and motion-related disruption, enabling improved assessment of choriocapillaris perfusion and ischemic signatures associated with chronic CSR. By timing imaging to the physiologic moments in which structural and vascular noise is minimized, AI-Gating creates a more reliable foundation for diagnosing acute CSR, monitoring chronic or recurrent forms, and assessing response to mineralocorticoid antagonists or photodynamic therapy.

TABLE 26

| Central Serous Chorioretinopathy: Fluctuating Biomarkers and AI-Gated Precision. | | | | |
|---|---|---|---|---|
| Fluctuating Feature | Pathophysiologic Basis in CSR | Conventional Imaging Limitation | AI-Gated Improvement Mechanism | Clinical Impact |
| Subretinal fluid height oscillation | Pulsatile choroidal congestion; RPE pump variability | Variable SRF thickness measurements | Captures OCT during fluid-height stabilization | More accurate SRF quantification |
| Choroidal thickness pulsatility | Venous overload and hyperpermeability | Distorted choroidal profiles | Gates acquisition to vasodynamic harmonics | Improved analysis of choroidal thickening |
| RPE microrip visibility | Mechanical stress and serous detachment | Inconsistent or incomplete visualization | Times imaging to reflectance-coherent intervals | Enhanced detection of subtle RPE defects |
| Choriocapillaris flow irregularity | Hyperpermeability and ischemia | Pulsatility-induced OCTA artifacts | Gates during perfusion-regularity phases | Clearer delineation of flow deficits |
| Fixation instability due to central distortion | Retinal contour disruption | Motion blur; false flow voids | Limits capture to microsaccadic slow-down | Reduces false-positive ischemia |

Table 26 shows key fluctuating biomarkers in CSR and the mechanisms through which AI-Gating improves reliability of structural and vascular imaging by targeting physiologic stability intervals.

Table 26 summarizes the key physiologic and optical instabilities that characterize central serous chorioretinopathy and explains how AI-Gating enhances diagnostic reliability by synchronizing image acquisition to brief intervals of structural and vascular stability. By forecasting moments in which subretinal fluid height, choroidal pulsatility, RPE reflectance, and choriocapillaris flow temporarily quiet, AI-Gating enables clearer visualization of RPE microrips, more accurate quantification of fluid dynamics, and more consistent delineation of perfusion abnormalities across visits.

11.7 Tumors and Intraocular Neoplasia

Intraocular tumors, including uveal melanoma, lymphoma, metastases, retinoblastoma, hemangiomas, and a spectrum of benign or indeterminate lesions, exhibit complex interactions between biochemical composition, perfusion dynamics, structural deformation, and metabolic demand. These interactions create a constantly shifting optical environment in which Raman, OCT, hyperspectral, and other imaging modalities capture only fragments of the tumor's molecular and structural state at any given moment. Within this fluctuating landscape, even the most distinctive Raman features, melanin vibrational peaks, nucleic-acid-associated band shifts, lipid remodeling signatures, and oxidation-related conformational markers, may be inconsistently expressed from frame to frame.

The disclosed AI-Gating architecture directly addresses this limitation by analyzing real-time temporal biomarkers of optical and physiologic stability and permitting acquisition only when the tumor's spectral and structural signatures are momentarily coherent. Tumors generate such windows unpredictably, influenced by microvascular steadiness, suppression of tremor-related motion, tear-film stabilization, alignment consistency, and transient reductions in autofluorescence or silicone-oil interference. AI-Gating detects these brief periods, moments of spectral plateau, flow regularity, or reflectance quieting, and synchronizes Raman and imaging acquisition precisely to these intervals.

This temporal alignment dramatically improves the discriminability of Raman peaks associated with melanin, nucleic acids, carotenoids, proteins, and lipid membrane constituents. Subtle distinctions between benign nevi and melanoma, between primary uveal melanoma and metastatic lesions, or between lymphoma and inflammatory mimickers become more evident when acquisition occurs during peak coherence rather than during physiologic turbulence. Similarly, OCT and reflectance frames gated to motion-quiet intervals enhance visualization of tumor margins, subretinal fluid, choroidal deformation, and nodular or infiltrative patterns that otherwise appear blurred or noisy.

In lesions with highly variable metabolic activity, such as melanomas undergoing oxidative bursts, lymphomas with shifting cellular density, or hemangiomas displaying fluctuating perfusion, AI-Gating ensures that the spectral signatures analyzed by the AI-Gating engine 210 reflect reproducible biochemical states rather than transient fluctuations. This stabilizes the downstream classification pipeline, allowing the integrated AI-Enhanced Raman system to more confidently recognize malignancy-associated peaks, track spectral evolution over time, and align biochemical changes with therapeutic response or progression.

The advantages of AI-Gating are amplified in multimodal embodiments. When Raman data are fused with gated OCT, OCTA, reflectance, or hyperspectral imaging, the combined AI-Gated photomodulation system 202 obtains a synchronized structural-biochemical snapshot of the tumor during an optimally stable physiologic interval. This improves the ability to delineate tumor boundaries, identify early transformation within a nevus, characterize infiltrative lymphoma patterns, or detect subtle subclinical recurrence after therapy. The approach is equally valuable in silicone-oil-filled eyes, where AI-Gated acquisition during autofluorescence minima or spectral drift reductions enables diagnostically reliable Raman signatures that would otherwise be masked.

Across all tumor types, the integration of AI-Gating with AI-Assisted Raman spectroscopy provides a transformative layer of temporal intelligence. By targeting the physiologic moments in which tumor-associated biomarkers are most faithfully expressed, the AI-Gated photomodulation system 202 increases diagnostic sensitivity, improves lesion characterization, enhances longitudinal consistency, and supports earlier and more confident differentiation between benign, malignant, and inflammatory lesions. This consolidated framework aligns fully with the accepted patent disclosure and strengthens the conceptual foundation for AI-Gated tumor diagnostics.

TABLE 27

Tumor-Associated Biomarkers and the Impact of AI-Gating on Diagnostic Reliability

| Biomarker/ Feature | Modality | Biologic or Pathologic Basis | How AI-Gating Enhances Detection | Clinical Relevance |
|---|---|---|---|---|
| Melanin vibrational peaks (e.g., 1,380-1,580 $cm^{-1}$) | Raman | High melanin concentration in melanoma and some nevi | Targets acquisition to spectral-plateau moments when melanin peaks are maximally coherent | Differentiates melanoma from nevus and tracks biochemical shifts with progression |
| Nucleic acid and protein conformation markers | Raman | Reflect rapid proliferative activity and genomic instability | Reduces spectral noise during micro-motion and perfusion turbulence | Identifies malignant transformation and high-risk profiles |
| Lipid membrane remodeling signatures | Raman/ Hyperspectral | Tumor-driven membrane turnover and metabolic dysregulation | Aligns acquisition with reduced scattering intervals | Helps subtype tumors and monitor effects of therapy |
| Tumor margin irregularities, nodularity, or | OCT/ Reflectance | Structural deformation of adjacent tissue | Gated frames minimize tremor, blink-artifact, and | Improves boundary delineation and |

TABLE 27-continued

Tumor-Associated Biomarkers and the Impact of AI-Gating on Diagnostic Reliability

| Biomarker/ Feature | Modality | Biologic or Pathologic Basis | How AI-Gating Enhances Detection | Clinical Relevance |
|---|---|---|---|---|
| infiltration | | | tear-film variability | guides treatment decisions |
| Perfusion heterogeneity or flow voids | OCTA | Microvascular instability in melanoma, metastases, lymphoma | Captures OCTA when vascular pulsatility is in harmonic equilibrium | Enhances visualization of ischemic or vascular patterns important for diagnosis |
| Chromophore-specific Raman features (heme, carotenoids, porphyrins) | Raman | Tumor metabolism and vascular content | Gating during autofluorescence minima increases contrast | Identifies tumor subtype and metabolic behavior |
| Oxidative-stress or redox-state shifts | Raman | Reflect episodic metabolic surges for therapy response | Acquires spectra during redox-stability windows to reduce false variability | Enables earlier detection of progression or treatment response |
| Subretinal fluid or local detachment | OCT | Mechanical displacement from tumor growth | Motion-stable windows improve layer separation and contour clarity | Supports staging, surveillance, and decision-making regarding intervention |

Table 27 highlights the key structural, biochemical, and perfusion-related biomarkers associated with intraocular tumors and explains how AI-Gating improves their diagnostic visibility by restricting Raman, OCT, OCTA, and reflectance acquisition to brief physiologic intervals in which spectral signals stabilize, vascular pulsatility quiets, and motion artifacts diminish. By synchronizing capture to these optimal windows, AI-Gating enhances the clarity of tumor-specific signatures, sharpens boundary delineation, and improves the reliability of longitudinal assessment across benign, malignant, and indeterminate lesions.

11.8 Pediatric Retinal Disease

Pediatric retinal disease presents a uniquely difficult imaging environment, shaped not only by the underlying pathology but by the developmental characteristics of the visual system and the natural behavior of infants and children. Conditions such as retinopathy of prematurity (ROP), Coats disease, familial exudative vitreoretinopathy, and pediatric inherited dystrophies unfold within eyes that are in constant motion, never fully at rest even under cooperative conditions. Young children exhibit rapid fixation shifts, unpredictable saccades, high-amplitude drift, and blink cycles that lack the patterned regularity seen in adults. These factors create an optical landscape in which high-fidelity imaging is often possible only under anesthesia or physical restraint, approaches that carry risk, logistical burden, and inherent variability.

AI-Gating fundamentally alters this paradigm by introducing a physiologic timing mechanism that identifies the fleeting micro-intervals during which a child's eye becomes momentarily still, structurally coherent, or optically aligned. These motion-quiet windows, often lasting only a few milliseconds, are invisible to human observers and impossible for traditional "open-loop" imaging systems to exploit. By continuously interpreting eye-tracking vectors, SLO preview frames, reflectance harmonics, and minute shifts in corneal or retinal alignment, AI-Gating forecasts when the retinal architecture is most amenable to imaging and triggers acquisition during these transient periods of natural stability.

In ROP, where the retinal vasculature is rapidly evolving, and the distinction between plus disease and physiologic dilation may depend on capturing accurate vessel caliber, AI-Gated acquisition reduces the motion-related artifacts that often obscure vascular tortuosity or peripheral neovascular buds. In Coats disease, where exudation, telangiectasia, and aneurysmal changes produce heterogeneous reflectance and fluctuating structural patterns, AI-Gating enables clearer delineation of lesion borders by acquiring frames during brief periods in which scattering diminishes or fixation steadies momentarily.

For pediatric dystrophies, such as early-onset Stargardt disease or cone-rod dystrophy, the ability to synchronize imaging to moments of reflectance coherence allows earlier recognition of ellipsoid-zone irregularities, lipofuscin accumulation patterns, or outer retinal thinning that may otherwise remain hidden behind incessant motion.

By transforming chaotic pediatric ocular behavior into an exploitable source of physiologic information, AI-Gating allows clinicians to capture diagnostically meaningful images without sedation and without relying on operator reflexes or chance timing. The approach provides a safer, faster, and more consistent alternative to conventional pediatric imaging, reduces inter-exam variability, and enables earlier and more reliable detection of disease progression in a population where precision is often most needed.

TABLE 28

Pediatric Retinal Disease: Motion Instability and AI-Gated Imaging Improvement.

| Instability or Feature | Pathophysiologic/ Behavioral Basis | Impact on Conventional Imaging | AI-Gated Enhancement Mechanism | Clinical Importance |
|---|---|---|---|---|
| Constant fixation instability | Immature oculomotor control in infants and toddlers | Blur, segmentation failure, inconsistent vessel and foveal imaging | Predicts microsaccadic deceleration and triggers imaging during brief stillness | Enables high-quality OCT/OCTA without sedation |
| High-amplitude drift and rapid saccades | Developmental oculomotor variability | Distorted vascular maps and motion artifacts in ROP | Times OCTA capture to motion-quiet intervals | Improves detection of plus disease and peripheral neovascularization |
| Variable blink patterns and tear-film transience | Immature blink rhythm and surface instability | Scatter, reflectance irregularity, poor OCT layer delineation | Identifies post-blink coherence peaks | Enhances visualization of exudation and structural deformation |
| Rapid retinal structural change in exudative diseases | Coats disease, FEVR, pediatric leak syndromes | Unstable reflectance and boundary distortion | Gating during decreased edema scatter | Improves visualization of telangiectasia and exudative foci |
| Unpredictable head and body movement | Natural behavior in awake children | Large-scale misalignment, motion noise | SLO preview + tracking vectors predict moments of alignment | Reduces need for anesthesia or physical stabilization |
| Early dystrophic changes with low intrinsic signal | Pediatric inherited disorders | Subclinical EZ or RPE abnormalities easily obscured | Captures OCT/FAF during reflectance-coherent intervals | Enhances early detection of photoreceptor and RPE pathology |

Table 28 summarizes the predominant sources of physiologic and motion instability in pediatric retinal disease and explains how AI-Gating enhances diagnostic performance by synchronizing imaging to the brief natural intervals in which motion subsides, reflectance stabilizes, and structural boundaries become momentarily coherent. By exploiting these micro-windows of physiologic stillness, AI-Gating enables clearer, safer, and more reliable imaging in infants and children without the need for sedation.

11.9—Illustrative Systemic Disease Embodiments

Although conceived in the context of ophthalmic imaging, the AI-Gated photomodulation system 202 is naturally extensible to a wide array of systemic disorders that leave measurable signatures in the retina. The retina is a metabolically active, highly vascular, and neurologically integrated tissue whose optical behavior mirrors the physiologic rhythms of the body. As a result, systemic diseases, whether cardiometabolic, autoimmune, neurodegenerative, or mitochondrial, often manifest as subtle variations in retinal reflectance, perfusion regularity, autofluorescence texture, or Raman spectral composition. These signatures are real but frequently unstable: they drift with microvascular pulsatility, metabolic oscillation, fixation variability, and moment-to-moment changes in oxidative balance.

Such instability causes conventional imaging systems to sample the retina at physiologic moments that may not accurately reflect the underlying systemic condition. A frame captured during turbulent perfusion, elevated scatter, or oxidative flare may obscure early biomarker changes or exaggerate transient noise. Conversely, during brief intervals of physiologic coherence, the retina reveals a clearer representation of its structural, vascular, and biochemical state, intervals that traditional, ungated acquisition almost never captures reliably.

AI-Gating introduces a predictive layer that identifies these transient windows of coherence by analyzing the temporal behavior of perfusion dynamics, reflectance harmonics, autofluorescence variance, and Raman spectral patterns. During the milliseconds when vascular pulsatility harmonizes, metabolic activity stabilizes, or reflectance noise diminishes, the AI-Gated photomodulation system 202 triggers image or spectral acquisition. This physiologic synchronization improves clarity, reduces false variability, and produces retinal biomarkers that more faithfully represent the systemic physiology influencing them.

In neurodegenerative disorders such as Alzheimer's or Parkinson's disease, early retinal changes can be subtle and intermittent. AI-Gating times acquisition to periods in which oxidative noise is minimal or reflectance transitions are most stable, enhancing the visibility of amyloid-associated spectral plateaus or dopaminergic reflectance fluctuations. In cardiometabolic disease, where choroidal and retinal perfusion exhibit rhythmic irregularities, the system captures OCTA frames during phases of pulsatile regularity, improving the consistency of flow-void mapping and vascular density measurement.

For mitochondrial and other metabolic disorders, Raman acquisitions timed to metabolic-quiet intervals reduce spectral scatter and improve detection of redox-related vibrational modes. Autoimmune and inflammatory disorders benefit similarly: FAF and reflectance imaging captured during low-variance intervals improve the characterization of RPE hyper-autofluorescence or inflammatory scatter patterns. Even in renal disease, where microvascular dysregulation is reflected in flow-instability on OCTA, AI-Gating identifies the intervals in which microvascular flow becomes briefly coherent, enabling more reliable longitudinal analysis.

These embodiments do not claim systemic diagnosis through ocular imaging. Rather, they demonstrate that physiologic synchronization can meaningfully enhance the optical representation of ocular manifestations that correlate with broader systemic conditions. By improving clarity, reproducibility, and temporal comparability, AI-Gating strengthens the role of retinal imaging as a non-invasive window into systemic physiology.

AI-Gated photomodulation system 202 also implements closed-loop feedback 1006, and feeds that information back into the inference engine 224.

TABLE 29

Systemic Disease Embodiments and AI-Gated Enhancement.

| Systemic Disease | Retinal Biomarker | Modality | Role of AI-Gating |
|---|---|---|---|
| Alzheimer's Disease | Amyloid-associated Raman peaks; reflectance alterations | Raman/ Reflectance | Forecasts oxidative-quieting intervals to improve detection of weak amyloid-linked vibrational modes |
| Parkinson's Disease | Dopaminergic pathway-related reflectance transitions; contrast fluctuations | OCT/ Reflectance | Captures subtle reflectance transitions during motion-quiet micro-intervals for improved reproducibility |
| Diabetes Mellitus | Microaneurysm burden, capillary dropout, perfusion irregularity | OCTA | Times acquisition to pulsatile-regularity windows for more stable flow mapping |
| Cardiovascular Disease | Choroidal pulsatility, arterial/venous harmonic shifts | OCTA/ Reflectance | Synchronizes imaging with harmonic phases of pulsatile flow, reducing perfusion-noise artifacts |
| Mitochondrial Disorders | Redox-state oscillations; metabolic Raman signatures | Raman/NIR | Identifies metabolic plateau phases, improving spectral consistency and biomarker stability |
| Autoimmune & Inflammatory Disorders | RPE hyper-autofluorescence; inflammatory scatter | FAF/ Reflectance | Gated capture during low-variance FAF intervals enhances characterization of RPE texture and scatter |
| Renal Disease | Microvascular dysregulation and flow irregularity | OCTA | Predicts flow-coherence states to reduce variability in microvascular density analysis |

Table 29 highlights representative systemic disorders in which retinal biomarkers can be evaluated using standard ophthalmic modalities and shows how AI-Gating enhances these assessments by synchronizing acquisition to transient intervals of physiologic stability, such as metabolic quieting, perfusion regularity, or reflectance coherence. By capturing data during these optimal windows, AI-Gating improves the clarity, reproducibility, and longitudinal reliability of retinal signals that reflect broader systemic physiology, without asserting or implying ocular diagnosis of systemic disease.

Figure 7:
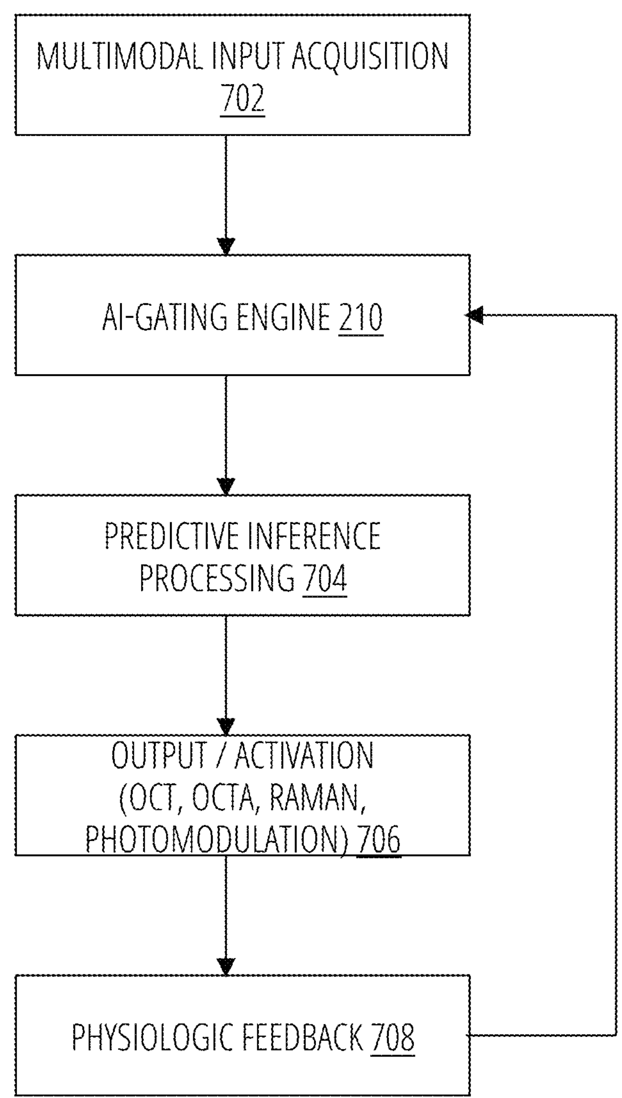
FIG. 7 illustrates a multimodal AI-Gating feedback loop.

FIG. 7 shows a multimodal AI-Gating feedback loop. After the multimodal input acquisition 702 receives data from one or more ophthalmic instruments, the data may be sent to the AI-Gating engine 210. The AI-Gating engine 210 may the perform predictive inference processing 704 and then initiate output/activation 706. The AI-Gated photomodulation system 202 then observes the physiologic feedback 708 and sends this feedback to the AI-Gating engine 210.

Figure 8:
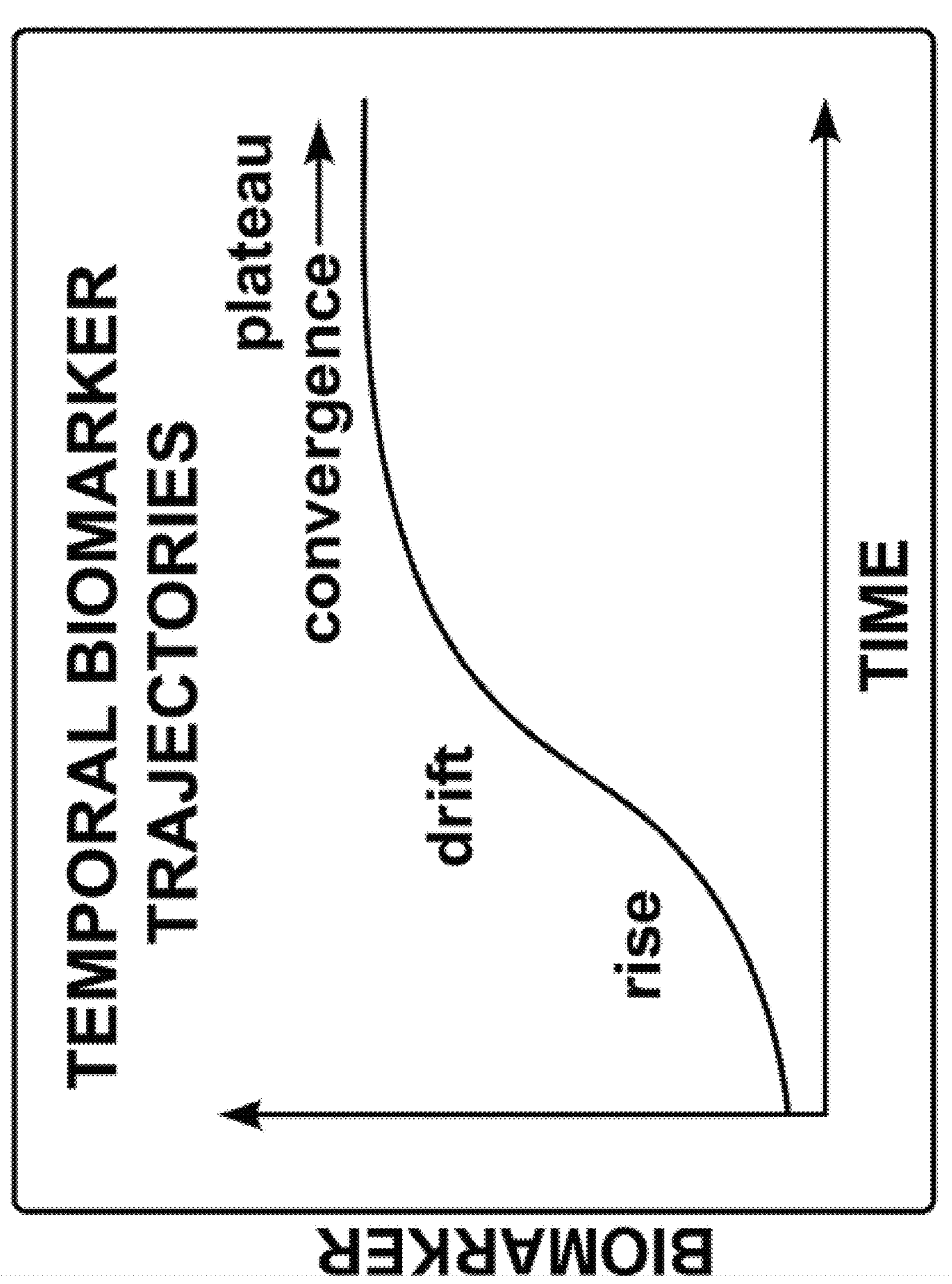
FIG. 8 shows the rise of biomarkers over time.

FIG. 8 shows the rise of biomarkers over time. As a physiological event occurs that triggers a biomarker, the biomarker level may first rise, and then drift before reaching a convergence plateau as time advances.

Figure 9:
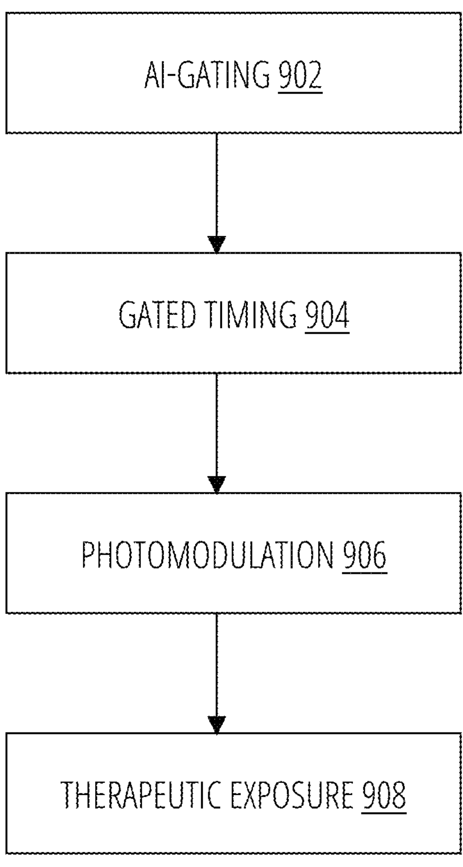
FIG. 9 shows the AI-Gated photomodulation timing sequence.

FIG. 9 illustrates the AI-Gated photomodulation timing sequence. Once the AI-Gating 902 sequence is completed, the gated timing 904 waits until the optimal moment to initiate photomodulation 906 for therapeutic exposure 908.

Figure 10:
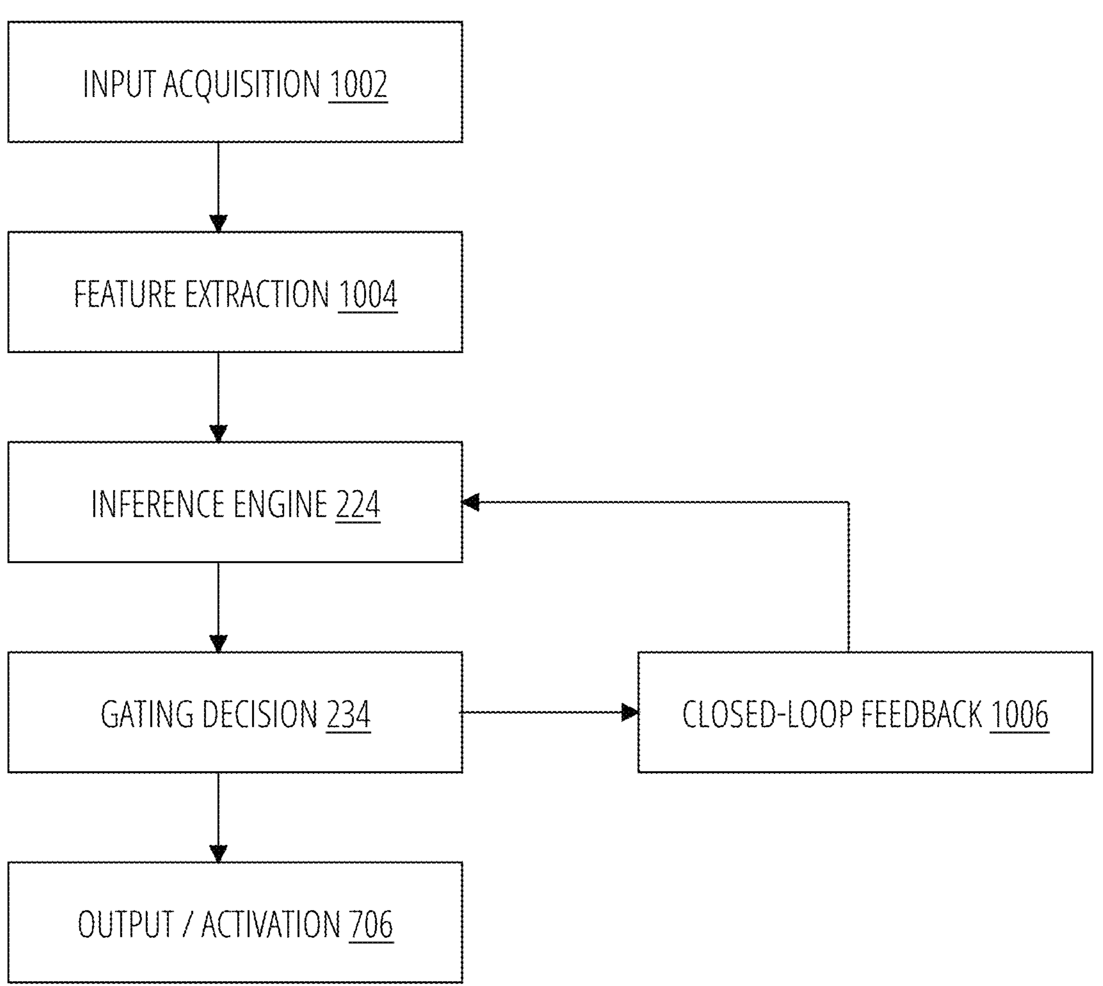
FIG. 10 illustrates a predictive AI-Gating engine.

FIG. 10 a predictive AI-Gating engine. First, input acquisition 1002 acquires the data from one or more ophthalmic instruments, and the features are extracted 1004. Then the inference engine 224 predicts when to make the gating decision with the gating logic 234. Once the gating decision is made, the system performs output/activation 706. The 12.0 Broad Application of the AI-Gating Predictive System Although many of the exemplary embodiments presented herein focus on retinal imaging for clarity, the disclosed AI-Gating architecture is not limited to the retina or to ophthalmic tissues. As used in this document, the term target tissue refers broadly to any biological structure capable of generating measurable optical, physiologic, or metabolic signals. This includes, without limitation, retinal tissue, subretinal layers, the retinal pigment epithelium, choroid, optic nerve head, ciliary body, trabecular meshwork, Schlemm's canal, cornea, conjunctiva, iris, and periocular vasculature, as well as additional tissues that may be evaluated using light-based or physiologic feedback.

The AI-Gated photomodulation system 202 is expressly designed as a modality-agnostic, predictive control framework capable of integrating with both current and future optical technologies. Its physiologic synchronization mechanisms function with standalone reflectance sensors, OCT and OCTA devices, fundus autofluorescence systems, Raman or hyperspectral spectrometers, and photonic therapeutic platforms. By abstracting the timing architecture from any specific hardware configuration, the AI-Gated photomodulation system 202 supports future embodiments involving additional tissues, emerging imaging modalities, new photonic sources, and expanded diagnostic or therapeutic functions.

The AI-Gated photomodulation system 202 could also be used in veterinary applications.

12.1 Closing Summary

The AI-Gating architecture disclosed in this application introduces a physiologic dimension to optical diagnostics and light-based therapy. Instead of acquiring data at arbitrary or device-driven intervals, the AI-Gated photomodulation system 202 identifies and forecasts future moments of structural, vascular, metabolic, or biochemical stability, intervals in which biological tissue is most receptive to imaging or photonic engagement.

By converting temporal physiologic behavior into a predictive control variable, the AI-Gated photomodulation system 202 transforms imaging and photomodulation from passive observation into actively synchronized events. Whether deployed in a compact standalone device or in a multimodal platform incorporating OCT, OCTA, FAF, Raman spectroscopy, hyperspectral imaging, or photobiomodulation, the system enhances signal fidelity, improves longitudinal reproducibility, reduces operator-dependent variability, and increases the biologic meaningfulness of each acquisition. This predictive synchronization paradigm establishes a foundational platform for next-generation ophthalmic and multisystem optical technologies.

12.2 Embodiments Statement

The embodiments, descriptions, and examples set forth above are intended to illustrate the principles, scope, and operational versatility of the AI-Gated photomodulation system 202 and are not provided as limitations. A person of ordinary skill in the art will readily understand that modifications, substitutions, and refinements may be made to the structure, algorithms, sensing strategies, photonic delivery mechanisms, and integration pathways without departing from the spirit of the inventions as defined in the claims. The physiologically synchronized predictive timing architecture disclosed herein is expressly intended to encompass all such variations, including future embodiments involving alternative tissues, newly developed imaging or spectroscopic modalities, therapeutic platforms, distributed or cloud-connected implementations, or enhanced computational models. All such modifications and extensions are considered to fall within the scope of the following claims.

Those skilled in the art will appreciate that the exemplary embodiments and descriptions thereof are merely illustrative of the inventions as a whole. Any dimensions used herein are for example, and any dimension may be modified without changing the scope of the claims. While the principles of the inventions have been made clear in the exemplary embodiments, it will be obvious to those skilled in the art that modifications of the structure, arrangement, proportions, elements, and materials may be utilized in the practice of the inventions, which are particularly adapted to specific environments and operative requirements without departing from the principles of the inventions.

LISTING OF DRAWING ELEMENTS

102 Raman spectrometer
104 OCT
106 OCT angiography
108 fundus imaging system
110 hyperspectral imaging
112 photomodulation platform
114 NIR reflectance imaging
116 scanning laser ophthalmoscopy
118 fundus autofluorescence
120 interferometric sensing
202 AI-Gated photomodulation system
204 illumination component
206 diagnostic acquisition component
208 physiologic monitoring subsystem
210 AI-Gating engine
212 normalize
214 noise detection
216 motion estimation
218 evaluate texture patterns
220 feature isolation
222 OCT preprocessing
224 inference engine
226 multimodal fusion
228 predictive engine
230 AI processing layer
232 photonic control
234 gating logic
236 actuation layer
302 predicted physiologic interval
304 AI-Gating logic
306 actuate photonic output
308 apply AI-Gated imaging or photomodulation output
310 output parameters
402 raw optical input (continuous stream)
404 preprocessing and signal stabilization
406 feature extraction
408 temporal modeling
410 pattern identification
412 predictive forecasting
414 gating decision
416 actuation event
418 closed-loop feedback integration
502 input
504 controller
506 plant
508 input
510 controller
512 feedback
514 measurement
516 open-loop
518 closed-loop
602 identify an upcoming physiologic stability window
604 synchronized trigger signal is generated
606 parallel actuation of multiple modalities
608 OCT acquisition initiated
610 OCTA capture triggered
612 Raman spectral sampling initiated
614 hyperspectral/SLO/NIR capture
616 multimodal data is collected from same physiologic state
618 unified dataset output
620 integrated into a predictive model
702 multimodal input acquisition
704 predictive inference processing
706 output/activation
708 physiologic feedback
902 AI-Gating
904 gated timing
906 photomodulation
908 therapeutic exposure
1002 input acquisition
1004 features are extracted
1006 closed-loop feedback

The invention claimed is:

1. A system for AI-Gating photonic interaction with ocular tissue, comprising:

at least one optical modality that acquires real-time input signals from the ocular tissue;

one or more processors that receive the real-time input signals and store the real-time input signals as historical input signals;

a predictive model executed by the one or more processors that forecasts a future interval of physiologic stability of the ocular tissue based on temporal patterns in the real-time input signals and the historical input signals, where the physiologic stability exhibits transient plateau behavior; and an AI-Gating engine executed by the one or more processors that generates a gating signal that regulates acquisition only during the future interval, wherein the gating signal optimizes operation of the at least one optical modality.

2. The system of claim 1, wherein the AI-Gating engine is an external supervisory controller connected to the at least one optical modality through a digital trigger line.

3. The system of claim 1, wherein the real-time input signals and the historical input signals include reflectance signals.

4. The system of claim 1, wherein the predictive model analyzes temporal patterns to identify a stability interval defined by reflectance coherence plateau behavior.

5. The system of claim 1, wherein the AI-Gating engine suppresses acquisition during predicted instability intervals.

6. The system of claim 1, wherein post-acquisition outcomes update the predictive model over time.

7. The system of claim 1, wherein the gating signal controls delivery of photomodulation energy.

8. The system of claim 1, wherein prediction is based on stabilization of autofluorescence intensity.

9. The system of claim 1, wherein at least one modality is directly gated and at least one modality is passively synchronized.

10. The system of claim 1, wherein the AI-Gating engine receives preview data without full-resolution imaging transfer.

11. The system of claim 1, wherein the ocular tissue includes a retina.

12. The system of claim 1, wherein the AI-Gating engine is also configured to generate a second gating signal that regulates photonic output.

13. A system for AI-Gating control of photonic delivery, comprising:

at least one optical modality that acquires real-time input signals from ocular tissue;

one or more processors that receive the real-time input signals and store the real-time input signals as historical input signals;

a predictive model executed by the one or more processors to forecast a future interval of physiologic stability of the ocular tissue based on temporal patterns in the real-time input signals and the historical input signals, where the physiologic stability exhibits transient plateau behavior; and an AI-Gating engine executed by the one or more processors that generates a gating signal that regulates photonic output only during the future interval, wherein the gating signal optimizes biologic receptivity or safety of the photonic delivery.

14. The system of claim 13, wherein the real-time input signals include fixation stability.

15. The system of claim 13, further comprising two or more optical modalities, wherein the AI-Gating engine synchronizes activation of the two or more optical modalities within the future interval.

16. The system of claim 15, wherein the two or more optical modalities include at least two of optical coherence tomography, optical coherence tomography angiography, fundus autofluorescence, hyperspectral imaging, near-infrared reflectance, or Raman spectroscopy.

17. The system of claim 13, wherein the photonic delivery includes pulsed light output.

18. The system of claim 13, wherein the predictive model analyzes temporal patterns to identify a stability interval defined by metabolic quieting.

19. The system of claim 13, wherein the AI-Gating engine is also configured to generate a second gating signal that regulates acquisition.

20. A method for operating an ophthalmic imaging system, comprising:

receiving real-time optical signals from ocular tissue;

analyzing the real-time optical signals together with historical data to predict a future temporal interval of physiologic stability wherein forecasting is based on physiologic signals exhibiting transient plateau behavior;

generating a gating signal based on the future temporal interval; and regulating delivery only during the future temporal interval to improve effective diagnostic performance.

21. The method of claim 20, where the regulating includes delaying imaging acquisition.

22. The method of claim 20, wherein the regulating includes modulating imaging acquisition.

23. The method of claim 20, wherein the gating signal coordinates multimodal acquisition within a shared stability window.

24. The method of claim 20, wherein closed-loop refinement occurs across multiple clinical sessions.

25. The method of claim 20, wherein a proportion of diagnostically usable frames is increased by restricting acquisition to the future temporal interval.

26. The method of claim 20, wherein passive synchronization aligns ungated modalities to a timing of a gated modality.

27. The method of claim 20, wherein the ophthalmic imaging system is applied for diagnosis and monitoring of a disease and physiologic condition characterized by time-dependent variability in ophthalmic biomarkers, including optical, metabolic, vascular, inflammatory, neurodegenerative, and biomechanical biomarkers, the ophthalmic imaging system configured to detect inflammatory, metabolic, vascular, neurodegenerative, toxic, degenerative, and neoplastic conditions, including diabetes, glaucoma, keratoconus, macular degeneration, geographic atrophy, central serous chorioretinopathy, uveitis, optic neuropathy, retinal vascular disease, inherited retinal disease, retinal dystrophy, ocular tumors, intraocular neoplasia, toxic maculopathy, mitochondrial disorders, Alzheimer's disease, and Parkinson's disease.

28. A non-transitory computer-readable medium storing instructions that, when executed by one or more processors, cause the instructions to:

receive at least one of real-time ocular optical inputs and real-time ocular physiologic inputs;

forecast a future interval of stability using a predictive model, where the stability exhibits transient plateau behavior; and issue, through an AI-Gating engine, a gating signal that controls photonic activation only during the future interval.

29. The instructions of claim 28, wherein the photonic activation is permitted only during predicted metabolic receptivity.

* * * * *